US007951827B2

(12) United States Patent
Tidwell et al.

(10) Patent No.: US 7,951,827 B2
(45) Date of Patent: May 31, 2011

(54) SYNTHESIS AND ANTIPROTOZOAL ACTIVITY OF DICATIONIC 3,5-DIPHENYLISOXAZOLES

(75) Inventors: Richard R. Tidwell, Pittsboro, NC (US); Svetlana M. Bakunova, Chapel Hill, NC (US); Stanislav Bakunov, Chapel Hill, NC (US); Donald A. Patrick, Apex, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 11/415,982

(22) Filed: May 2, 2006

(65) Prior Publication Data

US 2006/0264487 A1    Nov. 23, 2006

Related U.S. Application Data

(60) Provisional application No. 60/677,978, filed on May 5, 2005.

(51) Int. Cl.
*A61K 31/42* (2006.01)
*C07D 261/06* (2006.01)
*C07D 413/02* (2006.01)

(52) U.S. Cl. ........................................ 514/378; 548/247

(58) Field of Classification Search .................. None
See application file for complete search history.

(56) References Cited

U.S. PATENT DOCUMENTS

| 5,628,984 | A | 5/1997 | Boucher, Jr. | |
| 6,706,754 | B2 | 3/2004 | Werbovetz et al. | |
| 2007/0021483 | A1* | 1/2007 | Chalifour et al. | 514/394 |
| 2007/0088067 | A1* | 4/2007 | Tidwell et al. | 514/378 |

FOREIGN PATENT DOCUMENTS

| WO | WO 96/40138 | 12/1996 |
| WO | WO02/36588 | 5/2002 |
| WO | WO03/103598 A2 | 12/2003 |
| WO | WO 2005/025565 A1 | 3/2005 |
| WO | WO2005/033065 A | 4/2005 |

OTHER PUBLICATIONS

Patrick et al., "Synthesis and in vitro antiprotozoal activities of dicationic 3,5-diphenylisoxazoles", J. Med. Chem. 2007, 50, 2468-2485.*
Partial European Search Report corresponding to European Patent Application No. 06009279.8 dated Aug. 1, 2006.
Dann et al. *Trypanocide diamidine mit drei isolierten ringsystemen Justus Liebigs Annalen der Chemie.* Verlag Chimie HMBH. Weinheim, DE, 1975, pp. 160-194 [Abstract in English].
Office Communication corresponding to an EP Application No. 06009279.8-2117 dated Feb. 15, 2007.
Bell et al. Structure-Activity Relationships of Analogs of Pentamidine Against *Plasmodium falciparum* and *Leishmania mexicana amazonensis. Antimicrobial Agents and Chemotherapy*, vol. 34, No. 7, (1990), pp. 1381-1386.
Bell et al. Structure-Activity Relationships of Pentamidine Analogs against *Giardia lamblia* and Correlation of Antigiardial Activity with DNA-Binding Affinity. *Antimicrobial Agents and Chemotherapy*, vol. 35, No. 6, (1991), pp. 1099-1107.
Blagburn et al. Inhibition of *Cryptosporidium parvum* in Neonatal Hsd:(ICR)BR Swiss Mice by Polyether Ionophores and Aromatic Amidines. *Antimicrobial Agents and Chemotherapy*, vol. 35, No. 7, (1991), pp. 1520-1523.
Boykin et al. 2,5-Bis[4-(N-alkylamidino)phenyl]furans as Anti-*Pneumocystis carinii* Agents. *Journal of Medicinal Chemistry*, vol. 41, (1998), pp. 124-129.
Boykin et al. Dicationic Diarylfurans and Anti-*Pneumocystis carinii* Agents. *Journal of Medicinal Chemistry*, vol. 38, (1995), pp. 912-916.
Das et al. Synthesis and Antiprotozoal Activity of 2,5-Bis(4-guanylphenyl)furans. *Journal of Medicinal Chemistry*, vol. 20, No. 4, (1977), pp. 531-536.
Del Poeta et al. In Vitro Antifungal Activities of a Series of Dication-Substituted Cabazoles, Furans, and Benzimidazoles. *Antimicrobial Agents and Chemotherapy*, vol. 42, No. 10, (1998), pp. 2503-2510.
Del Poeta et al. In-vitro activity of dicationic aromatic compounds and fluconazole against *Cryptococcus neoformans* and *Candida.* ssp. *Journal of Antimicrobial Chemotherapy*, vol. 44, (1999), pp. 223-228.
Del Poeta et al. Structure-in Vitro Activity Relationships of Pentamidine Analogues and Dication-Substituted Bis-Benzimidazoles as New Antifungal Agents. *Antimicrobial Agents and Chemotherapy*, vol. 42, No. 10, (1998), pp. 2495-2502.
Francesconi et al. 2,4-Diphenyl Furan Diamidines as Novel Anti-*Pneumocystis carinii* Pneumonia Agents. *Journal of Medicinal Chemistry*, vol. 42, (1999), pp. 2260-2265.
Ismail et al. Synthesis and Antiprotozoal Activity of Aza-Analogues of Furamidine. *Journal of Medicinal Chemistry*, vol. 46, No. 22, (2003), pp. 4761-4769.
Kumar et al. Palladium Catalyzed Cross-Coupling Reactions for the Synthesis of 2.5-disubstitutedfurans. *Hetercyclic Communications*, vol. 5, (1999), pp. 301-304.
Lindsay et al. Activity of Pentamidine and Pentamidine Analogs against *Toxoplasma gondii* in Cell Cultures. *Antimicrobial Agents and Chemotherapy*, vol. 35, No. 9, (1991), pp. 1914-1916. Ling et al. Models for Intramolecular Exchange in Organic π-Conjugated Open-Shell Systems: 3-Nitrophenyl and 4-Nitrophenyl Units Connected by 2,5-Furandiyl, 2,5-Thiophenediyl, and 2,5-Pyffolediyl Nonaltemant Exchange Linkers. *Journal of American Chemical Society*, vol. 116, (1994), pp. 8784-8792.
Shearer et al. S-2-Naphthylmethyl Thioacetimidate Hydrobromide: A New Odorless Reagent for the Mild Synthesis of Substituted Acetamidines. *Tetrahedron Letters*, vol. 38, (1997), pp. 179-182.
Stephens et al. Diguanidino and "Reversed" Diamindino 2,5-Diarylfurans asn Antimicrobial Agents. *Journal of Medicinal Chemistry*, vol. 44, (2001), pp. 1741-1748.
Thompson et al. A General Synthesis of 5-Arylnicotinates. *Journal of Organic Chemistry*, vol. 49, (1984), pp. 5237-5243.

(Continued)

*Primary Examiner* — Sun Jae Y Loewe
(74) *Attorney, Agent, or Firm* — Jenkins, Wilson, Taylor & Hunt, P.A.

(57) ABSTRACT

Novel dicationic 3,5-diphenylisoxazole compounds are described. Synthetic routes to these novel compounds are provided. Several of the compounds displayed in vitro activity versus *Trypanosoma brucei brucei* and *Plasmodium falciparum* comparable to that of furamidine. A majority of the novel compounds also were less toxic to VERO cells than furamidine.

29 Claims, No Drawings

OTHER PUBLICATIONS

Trent et al. Targeting the Minor Groove of DNA: Crystal Structures of Two Complexes Between Furan Derivatives of Berenil and the DNA Dodecamer d(CGCGAATTCGCG)$_2$. *Journal of Medicinal Chemistry*, vol. 39, No. 23, (1996), pp. 4554-4562.

Anbazhagan et al. Synthesis of metabolites of the prodrug 2, 5-bis(4-O-Methoxyamidinophenyl) furan. *Heterocycles*, vol. 60, No. 5, (2003), pp. 1133-1145.

Baumstark et al. A carbon-13 Nmr Assignment study of 3,5-diarylisoxazoles. *Journal of Heterocylic Chemistry*, vol. 17, (1980), pp. 1719-1721.

Bergeron et al. Total synthesis of (±)-15-deoxyspergualin. *Journal of Organic Chemistry*, vol. 52, (1987), pp. 1700-1703.

Chrisope et al. Substituent effects in heterocyclic systems by carbon-13 nuclear magnetic resonance. Isoxazoles. *Journal of Heterocyclic Chemistry*, vol. 18, No. 4, (1981), pp. 795-798.

Friedman et al. Dimethylformamide as a useful solvent in preparing nitriles from aryl halides and cuprous cyanide; improved isolation techniques. *Journal of Organic Chemistry*, vol. 26, (1961), pp. 2522-2524.

Ismail et al. Synthesis and antiprotozoal activity of aza-analogues of furamidine. *Journal of Medicinal Chemistry*, vol. 46, (2003), pp. 4761-4769.

Maduskuie et al. Rational design and synthesis of novel, potent Bis-phenylamidine carboxylate factor Xa inhibitors. *Journal of Medicinal Chemistry*, vol. 41, (1998), pp. 53-62.

Miyatake et al. New poly(arylene ether)s with pendant phosphonic acid groups. *Journal of Polymer Science Part A: Polymer Chemistry*, vol. 39, No. 21, (2001), pp. 3770-3779.

Moriya et al. Dehydrochlorination of hydroximic acid chlorides by the use of organotin compounds: an application for synthesis of isoxazolines and isoxazoles. *Journal of the Chemical Society, Chemical Communications*, (1991), pp. 17-18.

Moriya et al. Generation of nitrile oxides via O-tributylstannyl aldoximes; application to the synthesis of isoxazolines and isoxazoles. *Journal of the Chemical Society, Perkin Transactions 1*, (1994), pp. 413-417.

Popat et al. Synthesis and biological activity of 3-aryl-5-(3'-bromo/chlorophenyl) isoxazoles. *Journal of Indian Chemical Society*, vol. 80, (2003), pp. 707-708.

Rutan et al. On the preparation of aryl nitriles using tosyl cyanide. *Journal of Organic Chemistry*, vol. 60, (1995), pp. 2948-2950.

Suman et al. Synthesis and antifungal acrivity of 1,3-bis(4-methyl/4-bromo/3-nitrophenyl) propan-1, 3-diones and their 2-[(4-bromo/4-chloro/2-nitro/2-ethoxy/2, 4-dichlorophenyl)azo] analogs. *Indian Journal of Chemistry*, vol. 34B, (1995), pp. 743-746.

Sunshine et al. Preparation of linear m-polyphenyls from mono- and dichalcones. *Journal of Organic Chemistry*, vol. 28, No. 10, (1963), pp. 2517-2522.

Thomsen et al. Synthesis of simple quinoline alkaloids. A novel quinazoline synthesis. *Acta Chemica Scandinavica*, (B), (1998), pp. 319-313.

Tschaen et al. An improved procedure for aromatic cyanation. *Synthetic Communications*, vol. 24, No. 6, (1994), pp. 887-890.

Communication pursuant to Article 94(3) EPC corresponding to European Patent Application No. 06 009 279.8-2117 dated Jul. 9, 2008.

Ashley et al., "A Chemotherapeutic Comparison of the Trypanocidal Action of Some Aromatic Diamidines," J. Chem. Soc. pp. 103-106 (1942).

Das et al., "Synthesis and Antitrypanosomal Activity of Some Bis(4-guanylphenyl) Five- and Six-Membered Ring Heterocycles," Journal of Medicinal Chemistry. vol. 23 pp. 578-581 (1980).

Office Communication corresponding to European Patent Application No. 06 009 279.8-2117 dated Jul. 1, 2009.

Tidwell, R.R., and Boykin D.W., "Dicationic DNA Minor Groove Binders as Antimicrobial Agents", in Small Molecule DNA + RNA Binders: From Synthesis to Nucleic Acid Complexes, vol. 2 (M. Demeunynck, C. Bailly and W.D., Wilson, ed., Wiley-VCH, New York) pp. 414-460 (2003).

Abe et al., "Large scale synthessi of N-benzyl-4-formylpiperidine through partial reduction of esters using aluminum hydride reagents modified with pyrrolidine," Tetrahedron. vol. 57 pp. 2701-2710 (2001).

Baltz et al., "Cultivation in a semi-defined medium of animal infective forms of *Trypanosoma brucei, T. equiperdum, T. evansi, T. rhodesiense* and *T. gambiense*," The EMBO Journal. vol. 4, No. 5 pp. 1273-1277 (1985).

Blackburn et al., "From Peptide to Non-Peptide. 3. Atropisomeric GPIIbIIIa Antagonists Containing the 3,4-Dihydro-1*H*-1,4-benzodiazepine-2,5-dione Nucleus," J. Med. Chem. vol. 40, No. 5 pp. 717-729 (1997).

Bleicher et al., "A Practial and Efficient Synthesis of the Selective Neuronal Acetylcholine-Gated Ion Channel Agonist (*S*)-(—)-5-Ethynyl-3-(1-methyl-2-pyrrolidinyl)pyridine Maleate (SIB-1508Y)," J. Org. Chem. vol. 63 pp. 1109-1118 (1998).

Boykin et al. "Anti-*Pneumocystis carinii* pneumonia activity of dicationic diaryl methylpyrimidines," Eur. J. Med. Chem. vol. 32 pp. 965 and 967-972 (1997).

Dirk, S.M., and Tour, J.M., "Synthesis of nitrile-terminated potential molecular electronic devices," Tetrahedron. vol. 59, No. 3 pp. 287-293 (2003).

Dulog et al., "Synthesis and Electrochemical Properties of 4-Phenyl-1-buten-3-yne-1,1,2-tricarbonitriles and Tricyanoacrylates," Liebigs Ann. Chem. vol. 9 pp. 1663-1671 (1995).

Gilbert et al., "Design and SAR of Novel Potassium Channel Openers Targeted for Urge Urinary Incontinence. 2. Selective and Potent Benzylamino Cyclobutenediones," J. Med. Chem. vol. 43 pp. 1203-1214 (2000).

Hamilton et al., "Regiocontrolled synthesis of the macrocyclic polyamine alkaloid (±)-lunarine, a time-dependent inhibitor of tyrpanothione reductase," J. Chem. Soc. Perkin Trans. 1 pp. 1115-1123 (2002).

Hill et al., "Synthesis of 2,3,5-Trihydroxyphenylprop-1-ene and its 4-Chloro-, 6-Chloro-, and 4,6-Dichloro-Derivatives," J. Chem. Soc. Perkin Trans. 1 pp. 2209-2215 (1987).

Hino et al., "Nonsteroidal Antiinflammatory Agents. III. [1)] Synthesis of the Metabolites of 10,11-Dihydro-8,α-dimethyl-11-oxodibenz-[*b,f*]oxepin-2-acetic Acid (Bermoprofen)," Chem. Pharm. Bull. vol. 36, No. 9 pp. 3462-3467 (1988).

Laali et al., "Substituent Control of Intramolecular Hydrogen Bonding in Formyl-Protonated *o*-Anisaldehydes: A Stable Ion and Semiempirical MO Investigation," J. Org. Chem. vol. 58 pp. 1385-1392 (1993).

Liu et al., "A Particularly Convenient Preparation of Benzohydroximinoyl Chlorides (Nitrile Oxide Precursors)," J. Org. Chem. vol. 45 pp. 3916-3918 (1980).

Liu et al., "An Efficient Method for the Preparation of Benzylic Bromides," Synthesis. vol. 14 pp. 2078-2080 (2001).

Luliński, P., and Skulski, L., "Iodination of Both Deactivated and Activated Arenes with Sodium Periodate or Sodium Iodate as the Oxidants," Bull. Chem. Soc. Jpn. vol. 73, No. 4 pp. 951-956 (2000).

Mallory et al., "Phenacenes: a family of graphite ribbons. Part 3: Iterative strategies for the synthesis of large phenacenes," Tetrahedron. vol. 57 pp. 3715-3724 (2001).

Patrick et al., "Synthesis and anti-*Pneumocystis carinii* pneumonia activity of novel dicationic dibenzothiophenes and orally active prodrugs," Eur. J. Med. Chem. vol. 34 pp. 575-583 (1999).

Quan et al., Design and Synthesis of Isoxazoline Derivatives as Factor Xa Inhibitors. J. Med. Chem. vol. 42, No. 15 pp. 2752-2759 (1999).

Räz et al., "The Alamar Blue assay to determine drug sensitivity of African trypanosomes (*T.b. rhodesiense* and *T.b. gambiense*) in vitro," Acta Tropica. vol. 68 pp. 139-147 (1997).

Reiner et al., "Non-Covalent Thrombin Inhibitors Featuring P3-Heterocycles with P1-Monocyclic Arginine Surrogates," Bioorganic & Medicinal Chemistry Letters. vol. 12 pp. 1203-1208 (2002).

Riesgo et al., "Introduction of Benzo[*h*]quinoline and 1,10-Phenanthroline Subunits by Friedländer Methodology," J. Org. Chem. vol. 61 pp. 3017-3022 (1996).

Roesch, K.R., and Larock, R.C., "Synthesis of Isoindolo[2,1-*a*]indoles by the Palladium-Catalyzed Annulation of Internal Acetylenes," J. Org. Chem. vol. 66 pp. 412-420 (2001).

Schultz et al., "(Vinylaryloxy)acetic Acids. A New Class of Diuretic Agents. 3.[2,3] [(2-Nitro-1-alkenyl)aryloxy]acetic Acids," Journal of Medicinal Chemistry. vol. 19, No. 6 pp. 783-787 (1976).

Simpson et al., "o-Amino-ketones of the Acetophenone and Benzophenone Types," J. Chem. Soc. pp. 646-657 (1945).

Sobrio et al., "Radiosynthesis of [$^{18}$F]Lu29-024: A Potential PET Ligand for Brain Imaging of the Serotonergic 5-$HT_2$ Receptor," Bioorganic & Medicinal Chemistry. vol. 8 pp. 2511-2518 (2000).

Sperandeo, N.R., and Brun, R., "Synthesis and Biological Evaluation of Pyrazolylnaphthoquinones as New Potential Antiprotozoal and Cytotoxic Agents," ChemBioChem. vol. 4 pp. 69-72 (2003).

Spychala et al., "Synthesis of dicationic diaryltriazines nucleic acid binding agents," Eur. J. Med. Chem. vol. 29, pp. 363-367 (1994).

Tidwell et al., "Analogues of 1,5-Bis(4-amidinophenoxy)pentane (Pentamidine) in the Treatment of Experimental *Pneumocystis carinii* Pneumonia," Journal of Medicinal Chemistry. vol. 33, No. 4 pp. 1252-1257 (1990).

* cited by examiner

SYNTHESIS AND ANTIPROTOZOAL ACTIVITY OF DICATIONIC 3,5-DIPHENYLISOXAZOLES

CROSS REFERENCE TO RELATED APPLICATIONS

This application claims the benefit of and priority to U.S. Provisional Patent Application Ser. No. 60/677,978, filed May 5, 2005, the disclosure of which is incorporated herein by reference in its entirety.

TECHNICAL FIELD

The presently disclosed subject matter relates to methods for combating microbial infections with novel dicationic 3,5-diphenylisoxazole compounds, processes for synthesizing novel dicationic 3,5-diphenylisoxazole compounds, and the novel dicationic 3,5-diphenylisoxazole compounds themselves.

ABBREVIATIONS

| | |
|---|---|
| δ = | chemical shift |
| Ac = | acetyl |
| AcO = | acetoxyl |
| AcOH = | acetic acid |
| $Ac_2O$ = | acetic anhydride |
| Am = | amidine |
| AmOH = | amidoxime |
| Aq. = | aqueous |
| Ar = | argon |
| Bu = | butyl |
| ° C. = | degrees Celsius |
| calcd = | calculated |
| cm = | centimeters |
| conc. = | concentrated |
| $Cs_2CO_3$ = | cesium carbonate |
| dec = | decomposition point |
| DIBAL = | diisobutylaluminium hydride |
| DMF = | dimethylformamide |
| DMSO = | dimethylsulfoxide |
| $D_2O$ = | deuterium oxide |
| ESI = | electrospray ionization |
| EtOAc = | ethyl acetate |
| EtOH = | ethanol |
| g = | grams |
| h = | hours |
| HAT = | human African trypanosomiasis |
| HCl = | hydrogen chloride or hydrochloric acid |
| HPLC = | high-pressure liquid chromatography |
| Hz = | hertz |
| ip = | intraperitoneal |
| kg = | kilograms |
| KO-t-Bu = | potassium tert-butoxide |
| L. d. = | *Leishmania donovani* |
| M = | molar |
| Me = | methyl |
| MeO = | methoxyl |
| MHz = | megahertz |
| mL = | milliliters |
| mm = | millimeters |
| mM = | millimolar |
| m.p. = | melting point |
| MS = | mass spectroscopy |
| MTBE = | methyl tert-butyl ether |
| $Na_2CO_3$ = | sodium carbonate |
| $Na_2SO_4$ = | sodium sulfate |
| NBS = | N-bromosuccinimide |
| $NH_2OH \cdot HCl$ = | hydroxylamine hydrochloride |
| NMR = | nuclear magnetic resonance |
| p = | para |
| Pd-C = | 10% palladium on carbon |
| $Pd_2Cl_2(PPh_3)_2$ = | bis(triphenylphosphine)palladium dichloride |
| $Pd(PPh_3)_4$ = | tetrakis(triphenylphosphine)palladiun |
| P. f. = | *Plasmodium falciparum* |
| P. *falciparum* = | *Plasmodium falciparum* |
| po = | oral |
| psi = | pounds per square inch |
| spp. = | species |
| T. *brucei brucei* = | *Trypanosoma brucei brucei* |
| T. b. *gambiense* = | *Trypanosoma brucei gambiense* |
| T. b. r. = | *Trypanosoma brucei rhodesiense* |
| T. *cruzi* = | *Trypanosoma cruzi* |
| THF = | tetrahydrofuran |
| TLC = | thin-layer chromatography |
| TMS = | trimethylsilyl |
| TMSA = | (trimethylsilyl)acetylene |
| $t_R$ = | retention time |
| UV = | ultraviolet |

BACKGROUND

The antimicrobial activity of aromatic diamidines was first reported in the 1930's. See Tidwell, R. R. and Boykin, D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), 416-460. Since that time, dicationic molecules have received considerable attention as potential new therapeutic agents. Despite these efforts, pentamidine, first reported in 1942, see Ashley, J. N. et al., *J. Chem. Soc.*, 103-106, (1942), is the only compound from this class of molecules for which there has been significant human use. Pentamidine is currently used against primary stage human African trypanosomiasis (HAT), antimony-resistant leishmaniasis and also as a secondary drug for AIDS-related *P. carinii* pneumonia (PCP). See Tidwell, R. R. and Boykin. D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), 416-460. Pentamidine, however, must be administered parenterally, and causes potentially severe side effects. Further, drug resistance among parasites is emerging. Thus, there continues to be a need for improvement in the art for additional compounds having desirable antimicrobial activity, whether against the representative pathogens referenced above or against other pathogens.

SUMMARY

In some embodiments, the presently disclosed subject matter provides compounds of Formula (I):

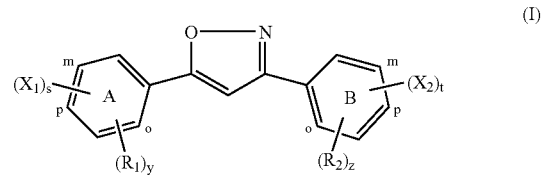

(I)

wherein:

$R_1$ and $R_2$ are each independently selected from the group consisting of H, alkyl, substituted alkyl, aryl, substituted aryl, halo, nitro, hydroxyl, alkoxyl, aryloxyl, and aralkyloxyl;

s and t are each independently an integer from 0 to 1, wherein at least one of s and t is 1;

y and z are each independently an integer from 0 to 3;

$X_1$ and $X_2$ are each selected from the group consisting of:

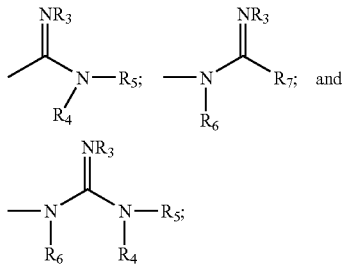

wherein:

each $R_3$ is independently selected from the group consisting of H, hydroxyl, acyloxyl, and alkoxyl;

each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_5$ together represent a $C_2$ to $C_{10}$ alkyl, $C_2$ to $C_{10}$ hydroxyalkyl, or $C_2$ to $C_{10}$ alkylene; or $R_3$ and $R_5$ together are:

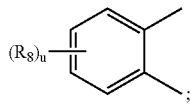

wherein u is an integer from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof;

subject to the proviso that the compound of Formula (I) is not 3,5-Bis(4-amidinophenyl)isoxazole.

In some embodiments, s, t, y, and z are each 1; $X_1$ and $X_2$ are attached at the m and/or p carbons of ring A and ring B; $R_1$ and $R_2$ are attached at the o carbon of ring A and ring B, respectively; and the compound of Formula (I) has a structure selected from the group consisting of:

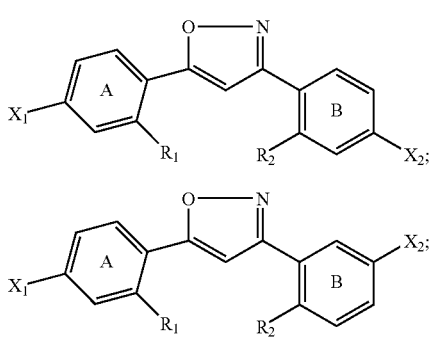

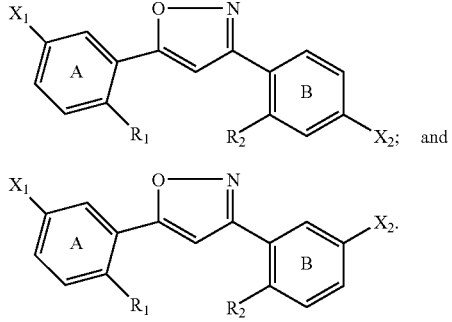

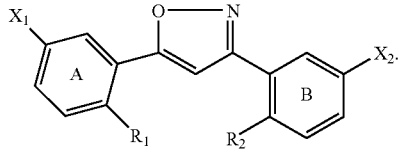

In some embodiments, the presently disclosed subject matter provides pharmaceutical formulations comprising a compound of Formula (I).

In some embodiments, the presently disclosed subject matter provides methods for preparing compounds of Formula (I).

In some embodiments, the presently disclosed subject matter provides the use of an active compound as described hereinabove, i.e., a compound of Formula (I), for the preparation of a medicament for treating a microbial infection.

It is accordingly an object of the presently disclosed subject matter to provide methods and compositions for treating microbial infections such as, but not limited to, those caused by *Trypanosoma* species (spp.), including, but not limited to, *Trypanosoma brucei rhodesiense, Trypanosoma brucei gambiense, Trypanosoma brucei brucei*, and *Trypanosoma cruzi*, and *Plasmodium falciparum* in a subject in need thereof. It is another object of the presently disclosed subject matter to provide a process for synthesizing compounds for treating microbial infections such as, but not limited to, those caused by *Trypanosoma* spp., including, but not limited to, *Trypanosoma brucei rhodesiense, Trypanosoma brucei gambiense, Trypanosoma brucei brucei*, and *Trypanosoma cruzi*, and *Plasmodium falciparum* infections.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. DEFINITIONS

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

As used herein, the term "chalcone" refers to a molecule that includes the following general formula:

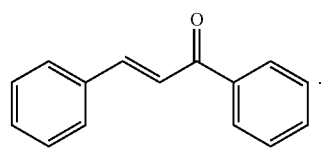

A structure represented generally by the formula:

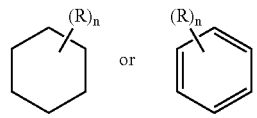

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

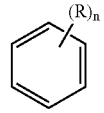

wherein n is an integer from 0 to 2, comprises compound groups including, but not limited to:

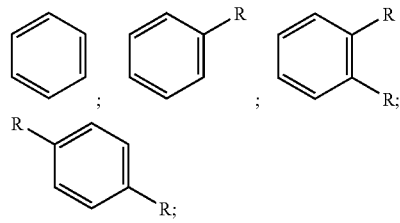

and the like.

The structure:

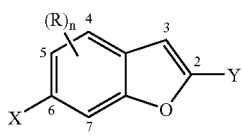

wherein n is one (1) comprises compound groups including:

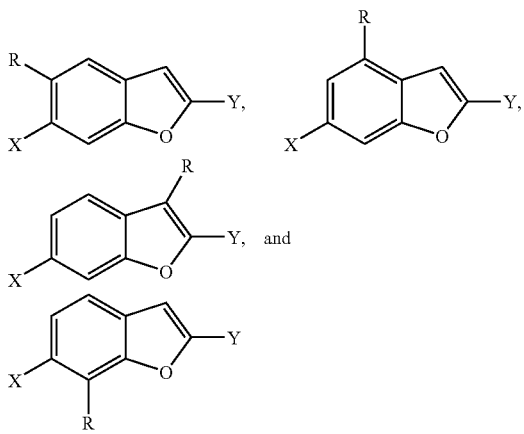

wherein the one (1) R substituent can be attached at any carbon on the benzofuran parent structure not occupied by another designated substituent, as in this case carbon 6 is substituted by X and carbon 2 is substituted by Y.

A dashed line representing a bond in a cyclic ring structure indicates that the bond can be either present or absent in the ring. That is a dashed line representing a bond in a cyclic ring structure indicates that the ring structure is selected from the group consisting of a saturated ring structure, a partially saturated ring structure, and an unsaturated ring structure.

In some embodiments, the compounds described by the presently disclosed subject matter contain a linking group. As used herein, the term "linking group" comprises a chemical moiety, such as a furanyl, phenylene, thienyl, and pyrrolyl radical, which is bonded to two or more other chemical moieties, in particular aryl groups, to form a stable structure.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" or "alkoxyalkyl" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —$NH_2$ group.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R", "R'", "X," "Y," "Y'", "A," "A'", "B," "L," or "Z" group will generally have the structure that is recognized in the art as corresponding to a group having that name, unless specified otherwise herein. For the purposes of illustration, certain representative "R," "X," "Y", and "A" groups as set forth above are defined below. These definitions are intended to supplement and illustrate, not preclude, the definitions that would be apparent to one of ordinary skill in the art upon review of the present disclosure.

The term "reflux" and grammatical derivations thereof refer to boiling a liquid, such as a solvent, in a container, such as a reaction flask, with which a condenser is associated, thereby facilitating continuous boiling without loss of liquid, due to the condensation of vapors on the interior walls of the condenser.

The term "aprotic solvent" refers to a solvent molecule, which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

The term "protic solvent" refers to a solvent molecule, which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The term "acid anhydride" refers to an anhydride of an organic acid and includes, but is not limited to acetic anhydride (($CH_3C=O)_2O$ or $Ac_2O$) and benzoic anhydride (($C_6H_5C=O)_2O$).

II. NOVEL COMPOUNDS

The presently disclosed subject matter describes in some embodiments the synthesis of a series of dicationic diarylisoxazoles and their anti-microbial activity, including but not limited to anti-microbial activity against those caused by *Trypanosoma* spp. and *Plasmodium falciparum*. As used herein, the term *Trypanosoma* spp. encompasses microbes classified under the genus *Trypanosoma*, including, but not limited to, *Trypanosoma brucei rhodesiense, Trypanosoma brucei gambiense, Trypanosoma brucei brucei*, and *Trypanosoma cruzi*.

II.A. Compounds of Formula (I)

Described herein are novel diarylisoxazole compounds of Formula (I):

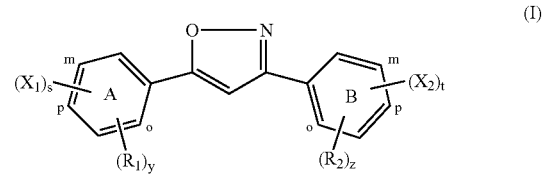

wherein:

$R_1$ and $R_2$ are each independently selected from the group consisting of H, alkyl, substituted alkyl, aryl, substituted aryl, halo, nitro, hydroxyl, alkoxyl, aryloxyl, and aralkyloxyl;

s and t are each independently an integer from 0 to 1, wherein at least one of s and t is 1;

y and z are each independently an integer from 0 to 3;

$X_1$ and $X_2$ are each selected from the group consisting of:

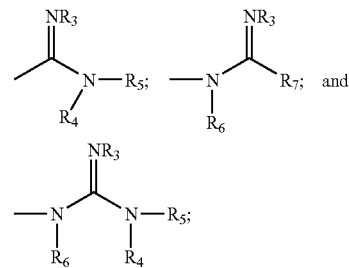

wherein:

each $R_3$ is independently selected from the group consisting of H, hydroxyl, acyloxyl, and alkoxyl;

each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_5$ together represent a $C_2$ to $C_{10}$ alkyl, $C_2$ to $C_{10}$ hydroxyalkyl, or $C_2$ to $C_{10}$ alkylene; or $R_3$ and $R_5$ together are:

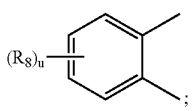

wherein u is an integer from 1 to 4, and $R_8$ is H or —CONHR$_9$NR$_{10}$R$_{11}$, wherein $R_9$ is alkyl, and $R_{10}$ and $R_{11}$, are each independently selected from the group consisting of H and alkyl;

or a pharmaceutically acceptable salt thereof;

subject to the proviso that the compound of Formula (I) is not 3,5-Bis(4-amidinophenyl)isoxazole.

In some embodiments, $X_1$ and $X_2$ are each:

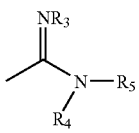

and $R_3$, $R_4$, and $R_5$ are each H. In some embodiments, $R_5$ is isopropyl. In some embodiments, $R_3$ is hydroxyl. In some embodiments, $R_3$ is acyloxyl. In some embodiments, $R_3$ and $R_5$ together are $C_2$ alkyl and $R_4$ is H, such that $X_1$ and $X_2$ are each:

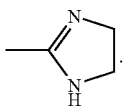

In some embodiments, $R_1$ and $R_2$ are each independently selected from the group consisting of H, chloro, nitro, and methoxy.

In some embodiments, s and t are each 1. In some embodiments, $X_1$ is attached to ring A through a direct bond to carbon m of ring A. In some embodiments, $X_1$ is attached to ring A through a direct bond to carbon p of ring A. In some embodiments, $X_2$ is attached to ring B through a direct bond to carbon m of ring B. In some embodiments, $X_2$ is attached to ring B through a direct bond to carbon p of ring B. Thus, when s and t are each 1, different combinations of the attachment of $X_1$ and $X_2$ to ring A and ring B, respectively, give rise to at least four regioisomeric analogs of Formula (I) which are referred to herein as Formulas (Ia-Id).

Accordingly, in some embodiments of compounds of Formula (I), s, t, y, and z are each 1; the $X_1$ and $X_2$ groups are attached at the p carbons of ring A and ring B; $R_1$ and $R_2$ are attached at the o carbon of ring A and ring B, respectively, and the compound of Formula (I) has the following structure:

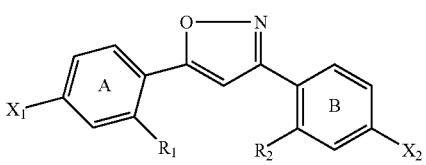

(Ia)

wherein:

$R_1$ and $R_2$ are each independently selected from the group consisting of H, alkyl, substituted alkyl, aryl, substituted aryl, halo, nitro, hydroxyl, alkoxyl, aryloxyl, and aralkyloxyl;

$X_1$ and $X_2$ are each:

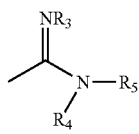

wherein:

each $R_3$ is independently selected from the group consisting of H, hydroxyl, acyloxyl, and alkoxyl;

each $R_4$ and $R_5$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_5$ together represent a $C_2$ to $C_{10}$ alkyl, $C_2$ to $C_{10}$ hydroxyalkyl, or $C_2$ to $C_{10}$ alkylene; or $R_3$ and $R_5$ together are:

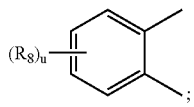

wherein u is an integer from 1 to 4, and $R_8$ is H or —CONHR$_9$NR$_{10}$R$_{11}$, wherein $R_9$ is alkyl, and $R_{10}$ and $R_{11}$ are each independently selected from the group consisting of H and alkyl;

or a pharmaceutically acceptable salt thereof;

subject to the proviso that the compound of Formula (Ia) is not 3,5-Bis(4-amidinophenyl)isoxazole.

In some embodiments, $R_3$, $R_4$, and $R_5$ are each H and at least one of $R_1$ and $R_2$ is selected from the group consisting of nitro, halo, alkyl, and alkoxyl.

In some embodiments of compounds of Formula (I), s, t, y, and z are each 1; $X_1$ is attached to carbon p of ring A and $X_2$ is attached to carbon m of ring B; $R_1$ and $R_2$ are attached at the o carbon of ring A and ring B, respectively, and the compound of Formula (I) has the following structure:

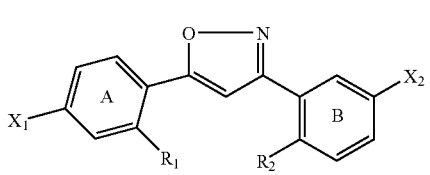

(Ib)

wherein:

$R_1$ and $R_2$ are each independently selected from the group consisting of H, alkyl, substituted alkyl, aryl, substituted aryl, halo, nitro, hydroxyl, alkoxyl, aryloxyl, and aralkyloxyl;

$X_1$ and $X_2$ are each:

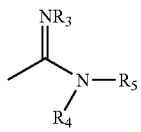

wherein:
  each $R_3$ is independently selected from the group consisting of H, hydroxyl, acyloxyl, and alkoxyl;
  each $R_4$ and $R_5$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_3$ and $R_5$ together represent a $C_2$ to $C_{10}$ alkyl, $C_2$ to $C_{10}$ hydroxyalkyl, or $C_2$ to $C_{10}$ alkylene; or
  $R_3$ and $R_5$ together are:

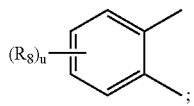

wherein u is an integer from 1 to 4, and $R_8$ is H or —CONHR$_9$NR$_{10}$R$_{11}$, wherein $R_9$ is alkyl, and $R_{10}$ and $R_{11}$ are each independently selected from the group consisting of H and alkyl;
or a pharmaceutically acceptable salt thereof.

In some embodiments of compounds of Formula (I), s, t, y, and z are each one; $X_1$ is attached to carbon m of ring A and $X_2$ is attached to carbon p of ring B; $R_1$ and $R_2$ are attached at the o carbon of ring A and ring B, respectively, and the compound of Formula (I) has the following structure:

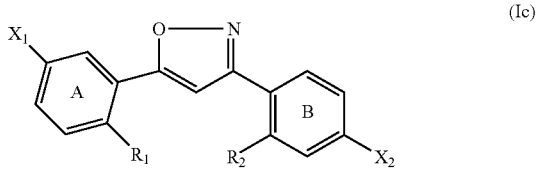

(Ic)

wherein:
$R_1$ and $R_2$ are each independently selected from the group consisting of H, alkyl, substituted alkyl, aryl, substituted aryl, halo, nitro, hydroxyl, alkoxyl, aryloxyl, and aralkyloxyl;
$X_1$ and $X_2$ are each:

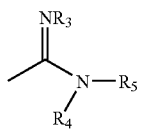

wherein:
  each $R_3$ is independently selected from the group consisting of H, hydroxyl, acyloxyl, and alkoxyl;
  each $R_4$ and $R_5$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_3$ and $R_5$ together represent a $C_2$ to $C_{10}$ alkyl, $C_2$ to $C_{10}$ hydroxyalkyl, or $C_2$ to $C_{10}$ alkylene; or
  $R_3$ and $R_5$ together are:

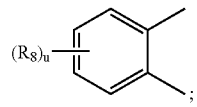

wherein u is an integer from 1 to 4, and $R_8$ is H or —CONHR$_9$NR$_{10}$R$_{11}$, wherein $R_9$ is alkyl, and $R_{10}$ and $R_{11}$ are each independently selected from the group consisting of H and alkyl;
or a pharmaceutically acceptable salt thereof.

In some embodiments of compounds of Formula (I), s, t, y, and z are each one, $X_1$ is attached to carbon m of ring A and $X_2$ is attached to carbon m of ring B; $R_1$ and $R_2$ are attached at the o carbon of ring A and ring B, respectively, and the compound of Formula (I) has the following structure:

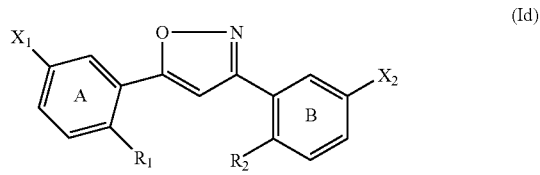

(Id)

wherein:
$R_1$ and $R_2$ are each independently selected from the group consisting of H, alkyl, substituted alkyl, aryl, substituted aryl, halo, nitro, hydroxyl, alkoxyl, aryloxyl, and aralkyloxyl;
$X_1$ and $X_2$ are each:

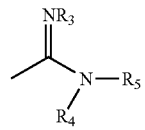

wherein:
  each $R_3$ is independently selected from the group consisting of H, hydroxyl, acyloxyl, and alkoxyl;
  each $R_4$ and $R_5$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_3$ and $R_5$ together represent a $C_2$ to $C_{10}$ alkyl, $C_2$ to $C_{10}$ hydroxyalkyl, or $C_2$ to $C_{10}$ alkylene; or $R_3$ and $R_5$ together are:

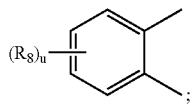

wherein u is an integer from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

In some embodiments, the compound of Formula (I) is selected from the group consisting of:

5-(4-Amidinophenyl)-3-phenylisoxazole;
3-(4-Amidinophenyl)-5-phenylisoxazole;
3,5-Bis[4-(N-isopropyl)amidinophenyl]isoxazole;
3,5-Bis[4-(2-imidazolinyl)phenyl]isoxazole;
5-(4-Amidino-2-nitrophenyl)-3-(4-amidinophenyl)isoxazole;
5-(4-Amidino-2-chlorophenyl)-3-(4-amidinophenyl)isoxazole;
5-(4-Amidino-2-methoxyphenyl)-3-(4-amidinophenyl)isoxazole;
3-(4-Amidino-2-nitrophenyl)-5-(4-amidinophenyl)isoxazole;
3-(4-Amidino-2-chlorophenyl)-5-(4-amidinophenyl)isoxazole;
3-(4-Amidino-2-methoxyphenyl)-5-(4-amidinophenyl)isoxazole;
3,5-Bis(4-amidino-2-methoxyphenyl)isoxazole;
3-(3-Amidinophenyl)-5-(4-amidinophenyl)isoxazole;
3-[3-(N-Isopropyl)amidinophenyl]-5-[4-(N-isopropyl)amidinophenyl]-isoxazole;
3-[3-(2-imidazolinyl)phenyl]-5-[4-(2-imidazolinyl)phenyl]isoxazole;
5-(4-Amidino-2-nitrophenyl)-3-(3-amidinophenyl)isoxazole;
5-(4-Amidino-2-chlorophenyl)-3-(3-amidinophenyl)isoxazole;
5-(4-Amidino-2-methoxyphenyl)-3-(3-amidinophenyl)isoxazole;
3-(5-Amidino-2-nitrophenyl)-5-(4-amidinophenyl)isoxazole;
3-(5-Amidino-2-chlorophenyl)-5-(4-amidinophenyl)isoxazole;
3-(5-Amidino-2-methoxyphenyl)-5-(4-amidinophenyl)isoxazole;
3-(4-Amidinophenyl)-5-(3-amidinophenyl)isoxazole;
3-[4-(N-Isopropyl)amidinophenyl]-5-[3-(N-isopropyl)amidinophenyl]-isoxazole;
3-[4-(2-Imidazolinyl)phenyl]-5-[3-(2-imidazolinyl)phenyl]isoxazole;
5-(5-Amidino-2-chlorophenyl)-3-(4-amidinophenyl)isoxazole;
5-(5-Amidino-2-methoxyphenyl)-3-(4-amidinophenyl)isoxazole;
3-(4-Amidino-2-nitrophenyl)-5-(3-amidinophenyl)isoxazole;
3-(4-Amidino-2-chlorophenyl)-5-(3-amidinophenyl)isoxazole;
3-(4-Amidino-2-methoxyphenyl)-5-(3-amidinophenyl)isoxazole;
5-(5-Amidino-2-methoxyphenyl)-3-(4-amidino-2-nitrophenyl)-isoxazole;
3-(4-Amidino-2-methoxyphenyl)-5-(5-amidino-2-methoxyphenyl)-isoxazole;
3,5-Bis(3-amidinophenyl)isoxazole;
3,5-Bis[3-(N-isopropyl)amidinophenyl]isoxazole;
3,5-Bis[3-(2-imidazolinyl)phenyl]isoxazole;
5-(5-Amidino-2-nitrophenyl)-3-(3-amidinophenyl)isoxazole;
5-(5-Amidino-2-chlorophenyl)-3-(3-amidinophenyl)isoxazole;
5-(5-Amidino-2-methoxyphenyl)-3-(3-amidinophenyl)isoxazole;
3-(5-Amidino-2-nitrophenyl)-5-(3-amidinophenyl)isoxazole;
3-(5-Amidino-2-chlorophenyl)-5-(3-amidinophenyl)isoxazole;
3-(5-Amidino-2-methoxyphenyl)-5-(3-amidinophenyl)isoxazole;
3,5-Bis(5-amidino-2-methoxyphenyl)isoxazole;
3,5-Bis[5-(N-isopropyl)amidino-2-methoxyphenyl]isoxazole;
3,5-Bis[5-(2-imidazolinyl)-2-methoxyphenyl]isoxazole;
3,5-Bis[4-(N-hydroxy)amidino-2-methoxyphenyl]isoxazole; and
3,5-Bis[4-(N-acetoxy)amidino-2-methoxyphenyl]isoxazole;

or a pharmaceutically acceptable salt thereof.

In some embodiments, the compound of Formula (I) comprises a pharmaceutically acceptable salt. In some embodiments, the pharmaceutically acceptable salt comprises a hydrochloride salt. In some embodiments, the pharmaceutically acceptable salt comprises an acetate salt.

II.B. Prodrugs

In representative embodiments, compounds disclosed herein are prodrugs. A prodrug means a compound that, upon administration to a recipient, is capable of providing (directly or indirectly) a compound of the presently disclosed subject matter or an inhibitorily active metabolite or residue thereof. Prodrugs can increase the bioavailability of the compounds of the presently disclosed subject matter when such compounds are administered to a subject (e.g., by allowing an orally administered compound to be more readily absorbed into the blood) or can enhance delivery of the parent compound to a biological compartment (e.g., the brain or lymphatic system) relative to a metabolite species, for example. Some of the compounds (e.g., 54 and 55) disclosed herein are prodrugs.

II.C. Pharmaceutically Acceptable Salts

Additionally, the active compounds as described herein can be administered as a pharmaceutically acceptable salt. Such pharmaceutically acceptable salts include the gluconate, lactate, acetate, tartarate, citrate, phosphate, borate, nitrate, sulfate, maleate, and hydrochloride salts. The salts of the compounds described herein can be prepared, for example, by reacting the base compound with the desired acid in solution. After the reaction is complete, the salts are crystallized from solution by the addition of an appropriate amount of solvent in which the salt is insoluble. In some embodiments, as described in more detail herein below, the hydrochloride salt of an amidoxime compound is made by passing hydrogen chloride gas into an ethanolic solution of the free base. In some embodiments, as described in more detail herein below, the acetate salt of the presently disclosed diamidine compounds and/or the corresponding N-methoxy analogues are made directly from the appropriate N-hydroxy analogue. Accordingly, in some embodiments, the pharmaceutically acceptable salt is a hydrochloride salt. In some embodiments, the pharmaceutically acceptable salt is an acetate salt.

III. PHARMACEUTICAL FORMULATIONS

The compounds of Formula (I), the pharmaceutically acceptable salts thereof, prodrugs corresponding to compounds of Formula (I), and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral, intravenous, or aerosol administration as discussed in greater detail below. Also, the presently disclosed subject matter provides such active compounds that have been lyophilized and that can be reconstituted to form pharmaceutically acceptable formulations for administration, for example, as by intravenous or intramuscular injection.

The therapeutically effective dosage of any specific active compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Treatment of a subject with lower doses and/or doses given less frequently can be used prophylactically to prevent or reduce the incidence of recurrence, e.g., a return of symptoms or relapse, of the infection or to prevent an infection in a subject who has never had an infection but is at risk of infection due to an increased likelihood of contact with a microbial agent that can cause an infection. Increased likelihood for contact with a microbial agent can come from the subject being present in geographical locations where the microbial agent is known to be prevalent.

In accordance with the present methods, pharmaceutically active compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a compound of Formula (I) described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula (I) or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formula (I), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

IV. METHODS FOR TREATING MICROBIAL INFECTIONS

Subjects with microbial infections can be treated by methods described herein. Such infections can be caused by a variety of microbes, including fungi, algae, protozoa, bacteria, and viruses. Exemplary microbial infections that can be treated by the method of the presently disclosed subject matter include, but are not limited to, infections caused by *Trypanosoma* spp. (e.g., *Trypanosoma brucei rhodesiense, Trypanosoma brucei gambiense, Trypanosoma brucei brucei*, and *Trypanosoma cruzi*), *Plasmodium* spp. (e.g., *Plasmodium falciparum*), *Mycobacterium tuberculosis, Pneumocytsis carnii, Giardia lamblia, Cryptosporidium parvum, Cryptococcus neoformans, Candida albicans, Candida tropicalis, Salmonella typhimurium, Leishmania donovani*, and *Leishmania mexicana amazonensis*. As used herein the terms *Trypanosoma* spp. and *Plasmodium* spp. encompass microbes classified under the genera *Trypanosoma* and *Plasmodium*, respectively. The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition.

The methods for treating microbial infections comprise administering to a subject in need of treatment thereof an active compound as described herein. These active compounds, as set forth above, include compounds of Formula (I), their corresponding prodrugs, and pharmaceutically acceptable salts of the compounds and prodrugs.

With regard to the presently described method embodiments, compounds of Formula (I) are defined as having a structure as follows:

(I)

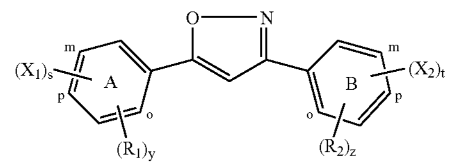

wherein:

$R_1$ and $R_2$ are each independently selected from the group consisting of H, alkyl, substituted alkyl, aryl, substituted aryl, halo, nitro, hydroxyl, alkoxyl, aryloxyl, and aralkyloxyl;

s and t are each independently an integer from 0 to 1, wherein at least one of s and t is 1;

y and z are each independently an integer from 0 to 3;

$X_1$ and $X_2$ are each selected from the group consisting of:

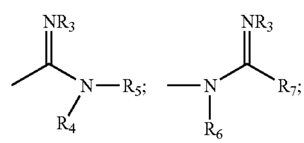

and 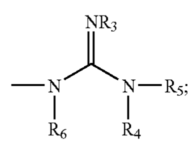 wherein:

each $R_3$ is independently selected from the group consisting of H, hydroxyl, acyloxyl, and alkoxyl;

each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_5$ together represent a $C_2$ to $C_{10}$ alkyl, $C_2$ to $C_{10}$ hydroxyalkyl, or $C_2$ to $C_{10}$ alkylene; or $R_3$ and $R_5$ together are:

wherein u is an integer from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof;

subject to the proviso that the compound of Formula (I) is not 3,5-Bis(4-amidinophenyl)isoxazole.

In some embodiments, $X_1$ and $X_2$ are each:

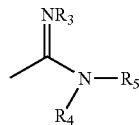

and $R_3$, $R_4$, and $R_5$ are each H. In some embodiments, $R_5$ is isopropyl. In some embodiments, $R_3$ is hydroxyl. In some embodiments, $R_3$ is acyloxyl. In some embodiments, $R_3$ and $R_5$ together are $C_2$ alkyl and $R_4$ is H, such that $X_1$ and $X_2$ are each:

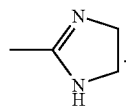

In some embodiments, s, t, y, and z are each 1, and the compound of Formula (I) has a regioisomeric structure selected from the group consisting of:

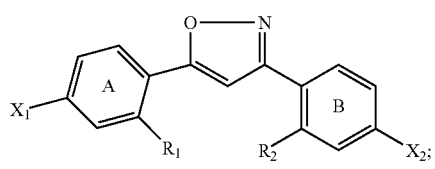

(Ia)

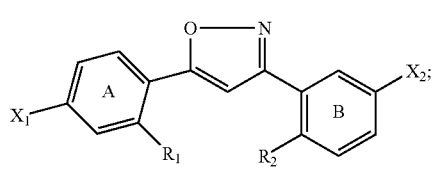

(Ib)

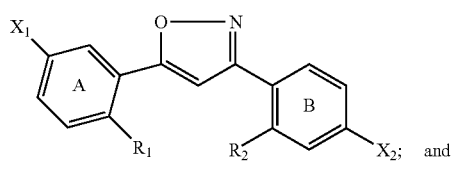

(Ic)

and

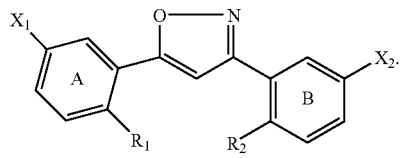

(Id)

In some embodiments, the compound of Formula I is administered in the form of a pharmaceutically acceptable salt. In some embodiments, the pharmaceutically acceptable salt comprises a hydrochloride salt. In some embodiments, the pharmaceutically acceptable salt comprises an acetate salt.

In some embodiments, the microbial infection comprises an infection caused by a *Trypanosoma* spp., including, but not limited to, *Trypanosoma brucei rhodesiense, Trypanosoma brucei gambiense, Trypanosoma brucei brucei*, and *Trypanosoma cruzi*. In some embodiments, the microbial infection comprises a *Plasmodium falciparum* infection.

In some embodiments, the compound of Formula (I) is administered to a subject with an existing microbial infection. In some embodiments, the compound of Formula (I) is administered prophylactically to prevent a microbial infection or to prevent the recurrence of a microbial infection. Thus, in some embodiments, the compound of Formula (I) is administered prophylactically to prevent or reduce the incidence of one of: (a) a microbial infection in a subject at risk of infection; (b) a recurrence of the microbial infection; and (c) combinations thereof.

The subject treated in the presently disclosed subject matter in its many embodiments is desirably a human subject, although it is to be understood the methods described herein are effective with respect to all vertebrate species, which are intended to be included in the term "subject." The methods described herein are particularly useful in the treatment and/or prevention of infectious diseases in warm-blooded vertebrates. Thus, the methods can be used as treatment for mammals and birds.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

V. GENERAL PROCESSES FOR THE SYNTHESIS OF DICATIONIC 3,5-DIPHENYLISOXAZOLES

The synthetic procedures provided herein below comprise representative embodiments of novel methods for preparing the presently disclosed compounds. The methods are outlined in Schemes 1-5 presented herein below and representative, non-limiting details are described in the Examples.

The amidines of the presently disclosed subject matter can be prepared from the corresponding nitriles. Described herein are two general methods for the preparation of the nitrile precursors of the presently disclosed amidines. The first method comprises a Claisen-Schmidt condensation (see Scheme 1 below). The second general method (see Scheme 2 below) comprises the cycloaddition of cyanophenylacetylenes and benzaldehyde chlorooximes.

In some embodiments, the presently disclosed subject matter provides a method for preparing a compound of Formula (I) and pharmaceutically acceptable salts thereof, the method comprising:
(a) condensing an aryl aldehyde and an aryl ketone together in a first polar solvent to form a chalcone;
(b) contacting the chalcone with a halogen in a first aprotic solvent to form a dihalochalcone;
(c) contacting the dihalochalcone with hydroxylamine hydrochloride and a base in a first protic solvent to form a diarylisoxazole;
(d) contacting the diarylisoxazole with a strong acid and an alcohol for a period of time, followed by an amine and an alcohol to form a compound of Formula (I), wherein the compound of Formula (I) is a diamidine.

In some embodiments, the method comprises:
(a) contacting the diarylisoxazole in a second aprotic solvent with one of:
    (i) cuprous cyanide to form a di-cyanide;
    (ii) zinc cyanide and tetrakis(triphenylphosphine)palladium to form a di-cyanide; and
    (iii) an alkyl lithium, followed by tosyl cyanide to form a dicyanide; and
(b) contacting the di-cyanide with a strong acid and an alcohol, followed by an amine and an alcohol to form a compound of Formula (I), wherein the compound of Formula (I) is a diamidine.

In some embodiments, the aryl aldehyde comprises a 3-bromobenzaldehyde. In some embodiments, the aryl aldehyde comprises a 4-bromobenzaldehyde. In some embodiments, the aryl aldehyde comprises a 3-cyanobenzaldehyde. In some embodiments, the aryl aldehyde comprises a 4-cyanobenzaldehyde.

In some embodiments, the aryl ketone comprises a 3'-bromoacetophenone. In some embodiments, the aryl ketone comprises a 4'-bromoacetophenone. In some embodiments, the aryl ketone comprises a 3'-cyanoacetophenone. In some embodiments, the aryl ketone comprises a 4'-cyanoacetophenone.

In some embodiments, the strong acid comprises hydrochloric acid.

In some embodiments, the halogen comprises bromine.

In some embodiments, the base comprises sodium hydroxide.

In some embodiments, the amine comprises ammonia. In some embodiments, the amine comprises isopropylamine. In some embodiments, the amine comprises ethylene diamine. In some embodiments, the amine comprises ammonium carbonate.

In some embodiments, the first polar solvent is selected from the group consisting of an alkyl alcohol and acetonitrile.

In some embodiments, the first aprotic solvent comprises chloroform.

In some embodiments, the first protic solvent comprises an alkyl alcohol. In some embodiments, the alkyl alcohol is selected from the group consisting of ethanol and methanol.

In some embodiments, the second aprotic solvent is dimethylformamide.

In some embodiments, the alcohol comprises ethanol.

In some embodiments, the alkyl lithium comprises t-butyl lithium.

In some embodiments, the presently disclosed subject matter provides a method for preparing a compound of Formula (I) and pharmaceutically acceptable salts thereof, the method comprising:
(a) contacting a phenylacetylene and a benzaldehyde chlorooxime in a first aprotic solvent in the presence of one of bis(tributyltin)oxide and triethylamine to form a diphenylisoxazole;
(b) contacting the diphenylisoxazole with one of:
    (i) a strong acid and an alcohol for a period of time, followed by an amine and an alcohol for a period of time to form a compound of Formula (I), wherein the compound of Formula (I) is a diamidine;
    (ii) hydroxylamine hydrochloride and a base to form a compound of Formula (I), wherein the compound of Formula (I) is a di-amidoxime;
    (iii) cuprous cyanide in a second aprotic solvent to form a dicyanide, followed by a strong acid and an alcohol for a period of time, followed by an amine and an alcohol for a period of time to form a compound of Formula (I), wherein the compound of Formula (I) is a diamidine;
    (iv) zinc cyanide and tetrakis(triphenylphosphine)palladium in a second aprotic solvent to form a di-cyanide, followed by a strong acid and an alcohol for a period of time, followed by an amine and an alcohol for a period of time to form a compound of Formula (I), wherein the compound of Formula (I) is a diamidine;
    (v) an alkyl lithium, followed by tosyl cyanide in a second aprotic solvent to form a di-cyanide, followed by a strong acid and an alcohol for a period of time, followed by an amine and an alcohol for a period of time to form a compound of Formula (I), wherein the compound of Formula (I) is a diamidine;

In some embodiments, the method further comprises:
(a) contacting the di-amidoxime with acetic anhydride and acetic acid to form a compound of Formula (I) wherein the compound of Formula (I) is a di-N-acetoxyamidine; and
(b) contacting the di-N-acetoxyamidine with 10% palladium-on-carbon, acetic acid and an alcohol to form a compound of Formula (I), wherein the compound of Formula (I) is a diamidine.

In some embodiments, the phenylacetylene comprises a 3-ethynylbenzonitrile. In some embodiments, the phenylacetylene comprises a 4-ethynylbenzonitrile.

In some embodiments, the chlorooxime comprises a chlorooxime prepared from a 3-cyanobenzaldehyde. In some embodiments, the chlorooxime comprises a chlorooxime prepared from a 4-cyanobenzaldehyde. In some embodiments, the chlorooxime comprises a chlorooxime prepared from a 3-bromobenzaldehyde.

In some embodiments, the strong acid comprises hydrochloric acid.

In some embodiments, the alcohol comprises ethanol.

In some embodiments, the first aprotic solvent comprises dichloromethane. In some embodiments, the first aprotic solvent comprises benzene. In some embodiments, the first aprotic solvent comprises chloroform.

In some embodiments, the second aprotic solvent comprises DMF.

In some embodiments, the amine comprises ammonia. In some embodiments, the amine comprises isopropylamine. In some embodiments, the amine comprises ethylene diamine.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Methods and Materials for Examples 1-3

Uncorrected melting points were measured on a Thomas-Hoover Capillary melting point apparatus (Thomas Scientific, Swedesboro, N.J., United States of America). $^1$H NMR spectra were recorded on a Varian Gemini 2000 (300 MHz) or a Varian 390 (90 MHz) spectrometer (Varian, Inc., Palo Alto, Calif., United States of America). Spectra were recorded at 300 MHz and in DMSO-$d_6$ (with 0.05% TMS) unless stated otherwise. Anhydrous EtOH was distilled over Mg/I$_2$ immediately prior to use. Other anhydrous solvents were purchased from Aldrich Chemical Co., Inc. Milwaukee, Wis., United States of America, in Sure/Seal™ (Aldrich Chemical Co., Inc.) containers and were used without further purification. Reaction mixtures were monitored by TLC on silica gel or by reverse-phase HPLC.

Organic layers of extraction mixtures were neutralized as necessary with acidic or basic washes, washed with saturated NaCl solution and dried over Na$_2$SO$_4$ or MgSO$_4$ before being evaporated under reduced pressure. Gravity and flash column chromatography were performed using Davisil grade 633, type 60A silica gel (200-425 mesh). Analytical HPLC chromatograms were recorded on a Hewlett-Packard 1090 Series II chromatograph (Hewlett-Packard Co., Palo Alto, Calif., United States of America) using a Zorbax® Rx C8 column (4.6×75 mm, 3.5 µm) (Agilent Technologies, Inc., Palo Alto, Calif., United States of America) and UV photodiode array detection at 230 nm, 254 nm, 265 nm, 290 nm, and 320 nm. Wavelengths reported are those at which the strongest signals of the major products were observed. Mobile phases consisted of mixtures of CH$_3$CN (0-75%) in water containing formic acid (80 mM), ammonium formate (20 mM) and triethylamine (15 mM). Flow rates were maintained at 1.5 mL/min at a column temperature of 40° C. In Method A, the concentration of CH$_3$CN was increased linearly from 0-22.5% over 6 min, then from 22.5-56.25% over 4 min, then maintained for 1 min. In Method B, the concentration of CH$_3$CN was increased linearly from 22.5-75% over 10 min, then maintained for 2 min.

Preparative reverse phase HPLC was performed on Varian ProStar Chromatography Workstation configured with two PS-215 pumps fitted with 50 mL pumpheads (Varian, Inc., Palo Alto, Calif., United States of America), a Dynamax Microsorb C18 (60 Å) column (41.4×25 cm, 8 µm), PS-320 variable wavelength UV-Vis detector, and a PS-701 fraction collector. Mobile phases consisted of mixtures of CH$_3$CN (0-75%) in water containing formic acid (40 mM) and ammonium formate (10 mM). Flow rates were maintained at 40 mL/min. Detector wavelengths and mobile phase gradients were optimized for the individual compounds. Select fractions were analyzed for purity using a Zorbax® Rx C8 column (4.6×75 mm, 3.5 µm) and the latter mobile phases on an Agilent Technologies 1100 chromatograph (Agilent Technologies, Inc., Palo Alto, Calif., United States of America). Pooled purified fractions were evaporated under reduced pressure, reconstituted in water, and lyophilized on a VirTis BenchTop 2K lyophilizer (VirTis, Gardiner, N.Y., United States of America). Low-resolution electrospray ionization (ESI) mass spectra were recorded on an Agilent Technologies 1100 Series LC/MSD Trap spectrometer (Agilent Technologies, Inc., Palo Alto, Calif., United States of America). Elemental analyses were performed by Atlantic Microlab, Norcross, Ga., United States of America, and, unless stated otherwise, were within ±0.4% of calculated values.

Example 1

General Methods for Converting Nitriles to Diamidines and Diamidine Hydrochlorides 3,5-Bis(4-amidinophenyl)isoxazole (3) and a series of novel analogs 1-2 and 4-43 were prepared as shown in Schemes 1-4 below. Compounds 1 and 2 are mono para-amidino analogs of 3. Alteration of the position (meta or para) and nature of the amidino group and the introduction of substituents on either aromatic ring, gave rise to four groups of regioisomeric analogs (3-12, 13-21, 22-31, and 32-43).

Compounds 1-43 were prepared from the corresponding nitrites. Monoamidines 1 and 2 and dicationic compounds 3-11, 13-43 were prepared by modified Pinner syntheses (Schemes 1 and 2). See Tidwell. R. R., et al., *J. Med. Chem.,* 33(4), 1252-1257 (1990); Patrick. D. A. et al., *Eur. J. Med. Chem.,* 34, 575-583 (1999). Following treatment of the nitrites with ethanolic HCl, the imidate intermediates were treated with ammonia, isopropylamine, or ethylenediamine to give the respective amidine, (N-isopropyl)amidine and imidazoline target compounds. The attempted preparation of diamidine 12 under similar conditions was unsuccessful, presumably due to the extremely low solubility of dinitrile 53f in the reaction medium. Alternatively, 53f was treated with hydroxylamine to give amidoxime 54. This intermediate underwent O-acetylation to 55, followed by catalytic hydrogenation in acetic acid/ethanol to give diamidine 12. See Anbazhagan, M. et al., *Heterocycles,* 60(5), 1133-1145 (2003). All compounds 1-43 were isolated as their hydrochloride salts.

The nitrile precursors of monoamidines 1 and 2 were prepared as reported. See Chrisope. D. R., et al., *J. Heterocylic Chem.,* 18(4), 795-798 (1981); Baumstark, A. L., et al., *J. Heterocylic Chem.,* 17, 1719-1721 (1980). Nitrile precursors of dicationic compounds 3-43 were prepared by two general methods as described in Examples 2 and 3 immediately herein below.

Example 2
Claisen-Schmidt Route to Dicationic Isoxazoles
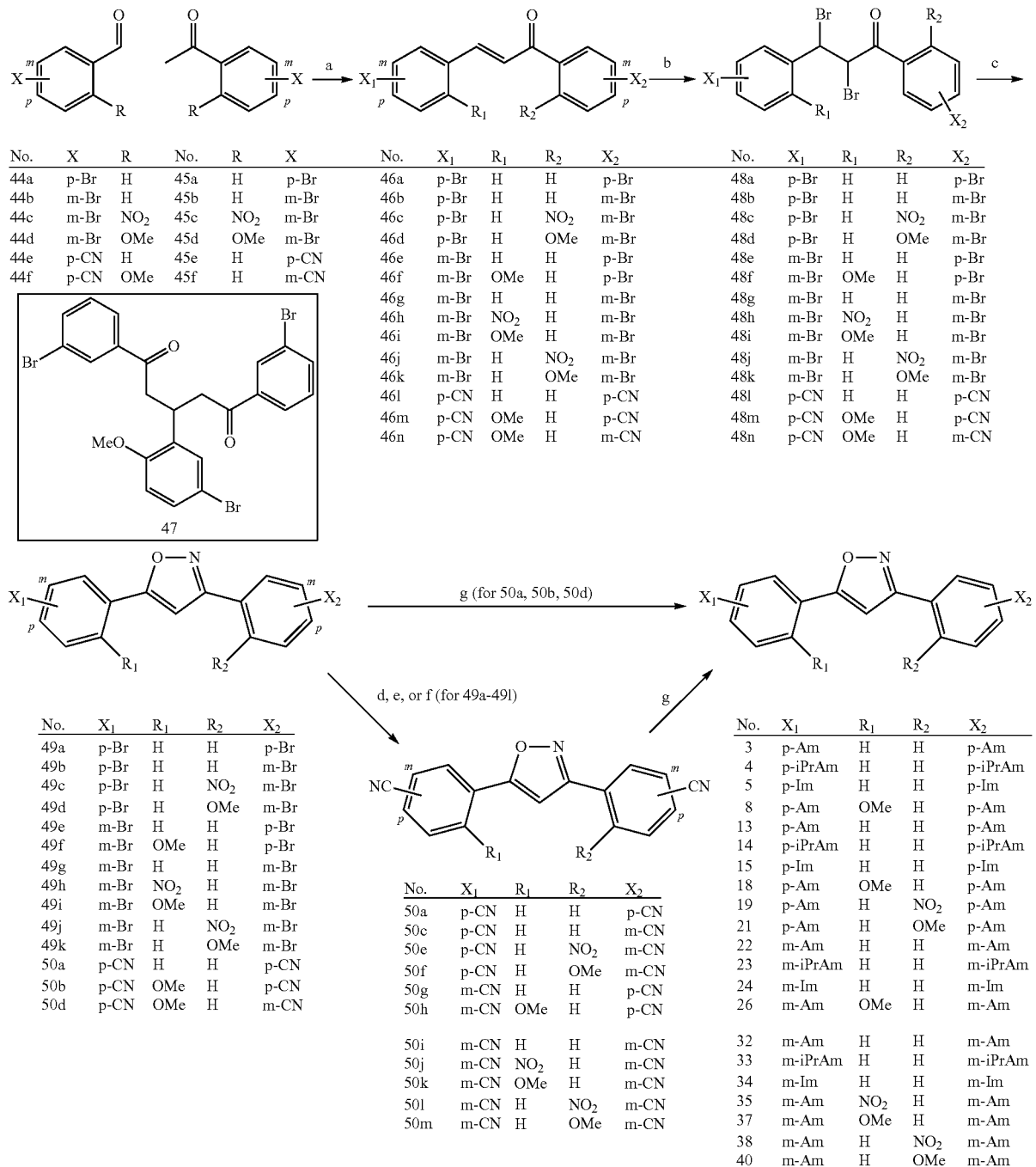
Scheme 1
Reagents and conditions:
a aq. NaOH, EtOH or MeOH or CH₃CN:
b Br₂, CHCl₃;
c NH₂OH·HCl, aq. NaOH, EtOH or MeOH;
d CuCN, DMF;
e Zn(CN)₂, Pd(PPh₃)₄, DMF;
f t-BuLi, THF, then tosyl cyanide, THF;
g EtOH, dry HCl, 1,4-dioxane, then appropriate amine, EtOH.

The first method comprises a Claisen-Schmidt condensation. Referring now to Scheme 1 immediately hereinabove, many of the necessary starting materials, benzaldehydes 44a, b,d,e and acetophenones 45a,b,d,e, were commercially available. The preparation of aldehyde 44f (Scheme 4) is described herein below. Aldehyde 44c and ketone 45c were prepared by nitration of 44b and 45b, respectively. See Sobrio. F. et al., *Bioorg. Med. Chem.*, 8, 2511-2518 (2000); Simpson, J. C. E. et al., *J. Chem. Soc.*, 646-657 (1945). Methoxyketone 45d was prepared from of the corresponding phenol. See Hamilton, C. J. et al., *J. Chem. Soc., Perkin Trans.*, 1, 1115-1123 (2002). Condensations between benzaldehydes 44 and acetophenones 45 gave dibromochalcones 46a-k and dicyanochalcones 46l-n, of which 46a,g,l had been reported previously. See Mivatake. K., et al., *J. Polym. Sci., Part A, Polym. Chem.*, 39(21), 3770-3779 (2001); Sunshine, N. B., et al., *J. Org. Chem.*, 28(10), 2517-2522 (1963); and Maduski, T. P., Jr. et al., *J. Med. Chem.*, 41(1), 53-62 (1998). The outcome of the Claisen-Schmidt reaction is sensitive to the nature and position of substituents on the starting materials, particularly the aldehydes. Chalcones 46a-d were prepared from aldehyde 44a and the appropriate ketone in ethanol at ambient temperature. In other cases, the use of different solvents or lower reaction temperatures resulted in greater yields or the avoidance of side-reactions. For example, a reaction between methoxyaldehyde 44d and ketone 45b in ethanol gave a 1:9 mixture (by HPLC) of chalcone 46i and compound 47 (a 1,4-addition product of 45b and 46i). The substitution of acetonitrile for ethanol as solvent resulted in the selective formation of chalcone 46i.

Bromination of chalcone 46a gave α,β-dibromoketone 48a as reported. See Suman, et al., *Indian J. Chem., Section B*, 34B, 8, 743-746 (1995). Similar treatment of compounds 46b-n gave ketones 48b-n in good yields in all cases except for analog 48i. Ethanolic solutions or suspensions of intermediates 48 were treated with hydroxylamine hydrochloride, followed by sodium hydroxide to effect the ring closures to dibromoisoxazoles 49a-k and dicyanoisoxazoles 50a-d. See Baumstark, A. L. et al., *J. Heterocylic Chem.*, 17, 1719-1721 (1980). (Preparations of compounds 49a,e and 50a by similar or different procedures have been reported previously.) See Dann, O., et al., *Liebigs Ann. Chem.*, 160-194 (1975); Popat, K. H. et al., *J. Indian Chem. Soc.*, 80(7), 707-708 (2003). Increased yields were obtained by allowing refluxing reaction mixtures to cool to ambient temperature immediately after the addition of the base or by performing the entire reactions at lower temperatures.

The dibromoisoxazoles 49a-k were converted to their dicyano analogs 50a,c,e-n. Treatment of 49a with copper(I) cyanide in refluxing DMF gave dinitrile 50a as reported. See Dann. O. et al., *Liebigs Ann. Chem.*, 160-194 (1975). Similar methodology was used to prepare analogs 50c,f-j,l,m. Different reaction conditions were required in other cases. Dibromonitroisoxazole 49c was reacted with zinc cyanide and tetrakis(triphenylphosphine)palladium(0) in DMF to give dinitrile 50e. See Tschaen, D. M. et al., *Synth. Commun.*, 24(6), 887-890 (1994). Dibromomethoxyisoxazole 49i was treated with tert-butyllithium in THF followed by tosyl cyanide to give dintrile 50k. See Kimberly. J. R. et al., *J. Org. Chem.*, 60(9), 2948-2950 (1995).

Example 3

Acetylene-Chlorooxime Coupling Route to Dicationic Isoxazoles

Scheme 2

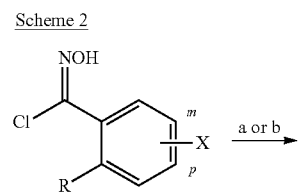

| No. | X | R | No. | R | X |
|-----|------|-----|------|-----|------|
| 51a | p-CN | H | 52a | H | p-CN |
| 51b | p-CN | NO₂ | 52b | NO₂ | p-CN |
| 51c | p-CN | Cl | 52c | Cl | p-CN |
| 51d | p-CN | OMe | 52d | OMe | p-CN |
| 51e | m-CN | H | 52e | H | m-CN |
| 51f | m-CN | Cl | 52f | Cl | m-Br |
| 51g | m-CN | OMe | 52g | Cl | m-CN |
|     |      |     | 52h | OMe | m-CN |

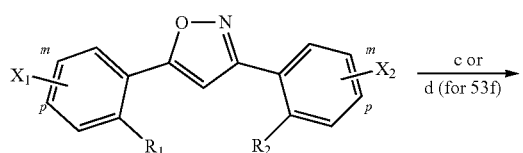

| No. | X₁ | R₁ | R₂ | X₂ |
|-----|------|------|------|------|
| 53a | p-CN | NO₂ | H | p-CN |
| 53b | p-CN | Cl | H | p-CN |
| 53c | p-CN | H | NO₂ | p-CN |
| 53d | p-CN | H | Cl | p-CN |
| 53e | p-CN | H | OMe | p-CN |
| 53f | p-CN | OMe | OMe | p-CN |
| 53g | p-CN | NO₂ | H | m-CN |
| 53h | p-CN | Cl | H | m-CN |
| 53i | p-CN | H | Cl | m-Br |
| 53j | p-CN | H | Cl | m-CN |
| 53k | m-CN | Cl | H | p-CN |
| 53l | m-CN | H | NO₂ | p-CN |
| 53m | m-CN | H | Cl | p-CN |
| 53n | m-CN | H | OMe | p-CN |
| 53o | m-CN | OMe | NO₂ | p-CN |
| 53p | m-CN | OMe | OMe | p-CN |
| 53q | m-CN | Cl | H | m-CN |
| 53r | m-CN | H | Cl | m-CN |
| 53s | m-CN | OMe | OMe | m-CN |
| 50a | p-CN | H | H | p-CN |
| 50b | p-CN | OMe | H | p-CN |
| 50g | p-CN | OMe | H | p-CN |
| 50k | m-CN | OMe | H | m-CN |

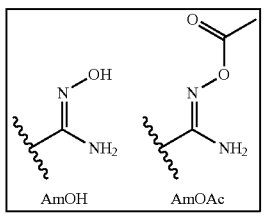

| No. | X₁ | R₁ | R₂ | X₂ |
|---|---|---|---|---|
| 6 | p-Am | NO₂ | H | p-Am |
| 7 | p-Am | Cl | H | p-Am |
| 9 | p-Am | H | NO₂ | p-Am |
| 10 | p-Am | H | Cl | p-Am |
| 11 | p-Am | H | OMe | p-Am |
| f ⎧ 54 | p-AmOH | OMe | OMe | p-AmOH |
| g ⎨ 55 | p-AmOAc | OMe | OMe | p-AmOAc |
| ⎩ 12 | p-Am | OMe | OMe | p-Am |
| 16 | p-Am | NO₂ | H | m-Am |
| 17 | p-Am | Cl | H | m-Am |
| 20 | p-Am | H | Cl | m-Am |
| 25 | m-Am | Cl | H | p-Am |
| 27 | m-Am | H | NO₂ | p-Am |
| 28 | m-Am | H | Cl | p-Am |
| 29 | m-Am | H | OMe | p-Am |
| 30 | m-Am | OMe | NO₂ | p-Am |
| 31 | m-Am | OMe | OMe | p-Am |
| 36 | m-Am | Cl | H | m-Am |
| 39 | m-Am | H | Cl | m-Am |
| 41 | m-Am | OMe | OMe | m-Am |
| 42 | m-iPrAm | OMe | OMe | m-iPrAm |
| 43 | m-Im | OMe | OMe | m-Im |

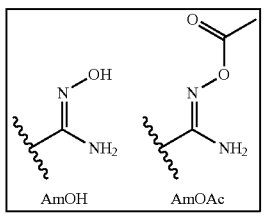

Reagents and conditions:
a (Bu₃Sn)₂O, CH₂Cl₂ or C₆H₆;
b Et₃N, CHCl₃;
c EtOH, dry HCl, 1,4-dioxane, then appropriate amine, EtOH;
d NH₂OH·HCl, t-BuOK, DMSO;
e CuCN, DMF,
f Ac₂O, Ac₂OH;
g H₂, 10% Pd/C, AcOH, EtOH.

A second general method is depicted in Scheme 2 immediately hereinabove and comprises the cycloaddition of cyanophenylacetylenes 51 and benzaldehyde chlorooximes 52 in the presence of bis(tributyltin)oxide, see Moriya. O. et al., *J. Chem. Soc., Perkin Trans.*, 1, 413417 (1994); Moriya. O. et al., *J. Chem. Soc., Chem. Commun.*, 17-18 (1991), or triethylamine, see Thomsen, I. et al., *Acta Chem. Scand. (B)*, 319-313 (1988), in nonpolar solvents to give isoxazole dinitriles 53a-h,k-s and bromonitrile 53i. The latter was treated with copper(I) cyanide to give dinitrile 53j. See Friedman, L. et al., *J. Org. Chem.*, 26, 2522-2524 (1961). This method also afforded alternate routes to dinitriles 50a,b,g,k prepared by the first method as provided in Scheme 1. The phenylacetylene synthons 51a-g were prepared as shown in Scheme 3 below. Starting materials 60a,e,g were commercially available. Nitration of 60a gave 60b. See Borsche, W. L. et al., *Chem. Ber.*, 49, 2222-2243 (1916). The latter was reduced to aniline 56, see Blanksma, J. J. et al., *Recl. Trav. Chim. Pays-Bas*, 66, 365-373 (1947), which underwent diazotization followed by treatment with copper(I) chloride to give chlorobenzene 60c. Triflate 60d was prepared by treatment of 4-bromo-3-hydroxybenzonitrile with triflic anhydride. The preparation of aryl iodide 60f began with the known transformation of aldehyde 57 to iodo derivative 58. See Lulinski, P., et al., *Bull. Chem. Soc. Jpn.*, 73(4), 951-956 (2000). Treatment of 58 with hydroxylamine hydrochloride gave aldoxime 59, which was dehydrated to give nitrile 60f using acetic anhydride. The aryl halides or triflates 60a-g were treated with (trimethylsilyl)acetylene, see Roesch, K. R. et al., *J. Org. Chem.*, 66, 412-420 (2001), or with 2-methyl-3-butyn-2-ol, see Bleicher, L. S., et al., *J. Org. Chem.*, 63, 1109-1118 (1998), to give intermediates 61a-f or 62a-f, respectively, of which 61a,d and 62a have been reported previously. See Dirk, S. M., et al., *Tetrahedron*, 59(3), 287-293 (2003); Bleicher, L. S. et al., *J. Org. Chem.*, 63, 1109-1118 (1998). The acetylenes 51 (of which 51a,e were known previously), see Blackburn, B. K., et al., *J. Med. Chem.*, 40(5), 717-729 (1997); Dulog. L., et al., *Liebigs Ann. Chem.*, 9, 1663-1671 (1995), were obtained by the treatment of intermediates 61 or 62 with cesium carbonate in acetonitrile or sodium hydride in toluene, respectively. See Bleicher, L. S., et al., *J. Org. Chem.*, 63, 1109-1118 (1998). The use of cesium carbonate in acetonitrile was introduced for the deprotection of intermediates 61 after the treatment of compound 61b with potassium carbonate in methanol, see Blackburn, B. K. et al., *J. Med. Chem.*, 40(5), 717-729 (1997), failed to give product 51b. The pathway using 2-methyl-3-butyn-2-ol provided more economical preparations of all phenylacetylenes 51 except nitro analog 51b.

Scheme 3

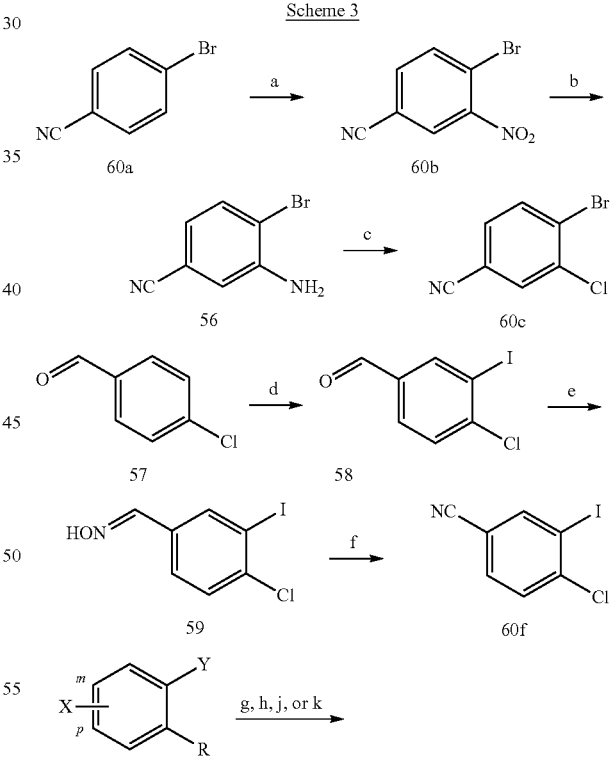

| No. | X | R | Y |
|---|---|---|---|
| 60a | p-CN | H | Br |
| 60b | p-CN | NO₂ | Br |
| 60c | p-CN | Cl | Br |
| 60d | p-CN | OMe | OTf |
| 60e | m-CN | H | Br |
| 60f | m-CN | Cl | I |
| 60g | m-CN | OMe | Br |

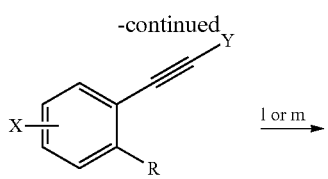

| No. | X | R | Y |
|---|---|---|---|
| 61a | p-CN | H | TMS |
| 61b | p-CN | NO₂ | TMS |
| 61c | p-CN | Cl | TMS |
| 61d | m-CN | H | TMS |
| 61e | m-CN | Cl | TMS |
| 61f | m-CN | OMe | TMS |
| 62a | p-CN | H | C(OH)Me₂ |
| 62b | p-CN | Cl | C(OH)Me₂ |
| 62c | p-CN | OMe | C(OH)Me₂ |
| 62d | m-CN | H | C(OH)Me₂ |
| 62e | m-CN | Cl | C(OH)Me₂ |
| 62f | m-CN | OMe | C(OH)Me₂ |

| No. | X | R |
|---|---|---|
| 51a | p-CN | H |
| 51b | p-CN | NO₂ |
| 51c | p-CN | Cl |
| 51d | p-CN | OMe |
| 51e | m-CN | H |
| 51f | m-CN | Cl |
| 51g | m-CN | OMe |

Reagents and conditions:
a fuming HNO₃, H₂SO₄;
b Fe, AcOH, EtOH;
c NaNO₂, aq. HCl, then CuCl;
d NaIO₄, I₂, AcOH, Ac₂O, H₂SO₄;
e NH₂OH·HCl, Py, EtOH
f Ac₂O;
g TMSA, Pd₂Cl₂ (PPh₃)₂, CuI, Et₃N;
h TMSA, PPh₃, Pd(PPh₃)₄, CuI, piperidine;
j 2-methyl-3 butyn-2-ol, Pd₂Cl₂(PPh₃)₂, CuI, Et₃N;
k 2-methyl-3-butyn-2-ol, 10% Pd/C, PPh₃, CuI, aq. K₂CO₃/DME;
l Cs₂CO₃, aq. CH₃CN or MeOH; (m) NaH, toluene.

The synthesis of benzaldehyde chlorooxime synthons 52 is depicted in Scheme 4, below. Of the eight aldehydes 44e-f and 74a-f, only 44e and 74d were commercially available. The preparation of aldehyde 44f began with the known three-step transformation of 4-methyl-3-nitrobenzonitrile 63 to methoxy compound 64. See Reiner. J. E., et al., *Bioorg. Med. Chem. Lett.*, 12, 1203-1208 (2002). α-Bromination of 64 using one equivalent of N-bromosuccinimide gave little selectivity between the mono- and dibromo adducts, but the analogous reaction using 2.5 equivalents gave dibromide 65 almost exclusively. Silver nitrate oxidation of dibromide 65 gave aldehyde 44f. See Hill, R. A. et al., *J. Chem. Soc., Perkin Trans.*, 1, 2209-2215 (1987). The reaction of the o-nitrotoluene 63 with N,N-dimethylformamide dimethyl acetal in DMF gave the enamine 66, which underwent oxidative cleavage using sodium periodate in THF, see Riesgo. E. C., et al., *J. Org. Chem.*, 61, 3017-3022 (1996), to give aldehyde 74a via a more facile preparation than previously reported. See Dann, O., et al., *Liebigs Ann. Chem.*, 3, 409-425 (1984). Aldehyde 74b also has been prepared previously. See Schultz, E. M., et al., *J. Med. Chem.*, 19(6), 783-787 (1976). A more expedient preparation of 74b began with chlorotoluene 67 undergoing α-bromination to 68, see Gilbert, A. M. et al., *J. Med. Chem.*, 43, 1203-1214 (2000), by a modification of the original procedure. See Liu, P. et al., *Synthesis*, 14, 2078-2080 (2001). The reaction of 68 with 2-nitropropane and sodium ethoxide in ethanol gave 74b. See Mallory. F. M. et al., *Tetrahedron*, 57, 3715-3724 (2001). Commercially available aldehyde 69 and aldehyde 71, see Hino, K. et al., *Chem. Pharm. Bull.*, 36(6), 3462-3467 (1988), which had been prepared via a Sandmeyer reaction from commercially available 70, were converted to methyl esters 72 and 73, respectively. The esters were converted to aldehydes 74c and 74e, respectively, using Red-Al® (sodium bis(2-methoxyethoxy)aluminium hydride) (Aldrich Chemical Co., Inc., Milwaukee, Wis., United States of America), pyrrolidine, and potassium tert-butoxide in methyl tert-butyl ether. See Abe. T. et al., *Tetrahedron*, 57, 2701-2710 (2001). Cyanoaldehyde 74f was prepared by debromocyanation of 44d. See Laali, K. K., et al., *J. Org. Chem.*, 58, 1385-1392 (1993). Aldehydes 44e-44f and 74a-74f were converted to oxime derivatives 75a-h (of which 75a,e were known previously), see Quan, M. L. et al., *J. Med. Chem.*, 42(15), 2752-2759 (1999), using hydroxylamine hydrochloride in either water/ethanol or pyridine/ethanol. The oximes were treated with N-chlorosuccinimide in DMF to give chlorooximes 52a-h, following the procedure reported for 52e. See Liu. K.-C. et al., *J. Org. Chem.*, 45, 3916-3918 (1980). The chlorooximes 52 were reacted with acetylenes 51 without further purification.

Scheme 4

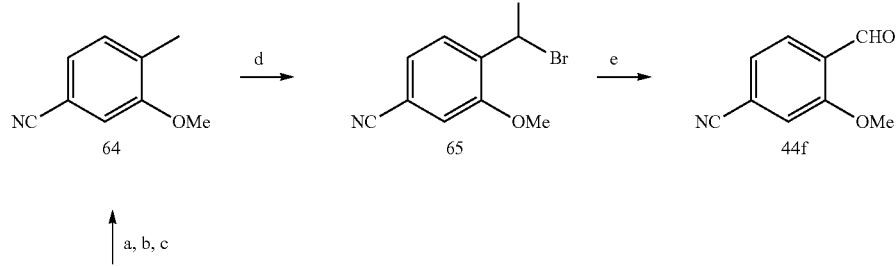

-continued

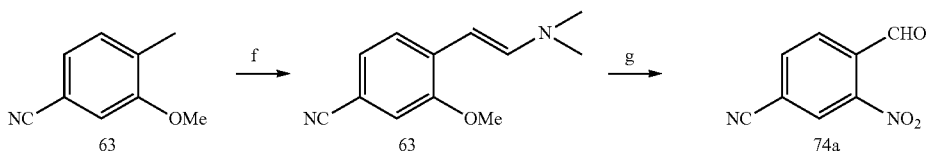

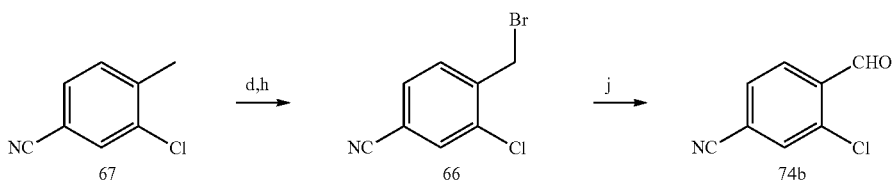

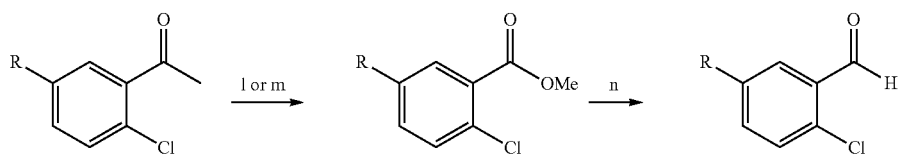

| No. | R |
|---|---|
| 69 | Br |
| 70 | NH₂ |
| 71 | CN |

| No. | R |
|---|---|
| 72 | Br |
| 73 | CH |

| No. | R |
|---|---|
| 74c | Br |
| 74e | CN |

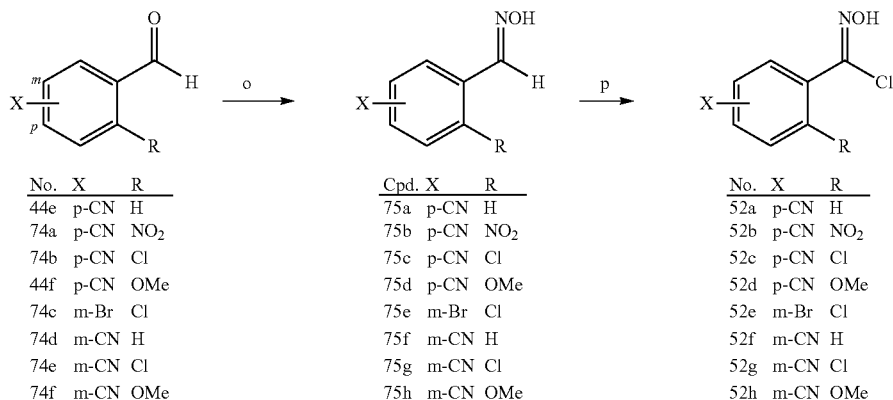

| No. | X | R |
|---|---|---|
| 44e | p-CN | H |
| 74a | p-CN | NO₂ |
| 74b | p-CN | Cl |
| 44f | p-CN | OMe |
| 74c | m-Br | Cl |
| 74d | m-CN | H |
| 74e | m-CN | Cl |
| 74f | m-CN | OMe |

| Cpd. | X | R |
|---|---|---|
| 75a | p-CN | H |
| 75b | p-CN | NO₂ |
| 75c | p-CN | Cl |
| 75d | p-CN | OMe |
| 75e | m-Br | Cl |
| 75f | m-CN | H |
| 75g | m-CN | Cl |
| 75h | m-CN | OMe |

| No. | X | R |
|---|---|---|
| 52a | p-CN | H |
| 52b | p-CN | NO₂ |
| 52c | p-CN | Cl |
| 52d | p-CN | OMe |
| 52e | m-Br | Cl |
| 52f | m-CN | H |
| 52g | m-CN | Cl |
| 52h | m-CN | OMe |

Reagents and conditons:
a H₂, 10% Pd/C, EtOH;
b NaNO₂, aq. H₂SO₄;
c CH₃I, NaH, DMF;
d NBS, benzoyl peroxide, CCl₄;
e AgNO₃, aq. EtOH; (f) DMFDMA, DMF;
g NaIO₄; aq. THF;
h diethyl phosphite, (i-Pr)₂NEt, THF:
j 2-nitropropane, NaOEt, EtOH;
k NaNO₂, aq. HCl, then CuCN, KCN;
l MeOH, H₂SO₄;
m DCC, DMAP, MeOH, CH₂Cl₂;
n Red-Al®, t-BuOK, pyrrolidine, MTBE;
o NH₂OH·HCl, H₂O/EtOH or Py/EtOH
p NCS, DMF.

Example 4

Synthesis of Representative Guanidines and "Reversed" Amidines

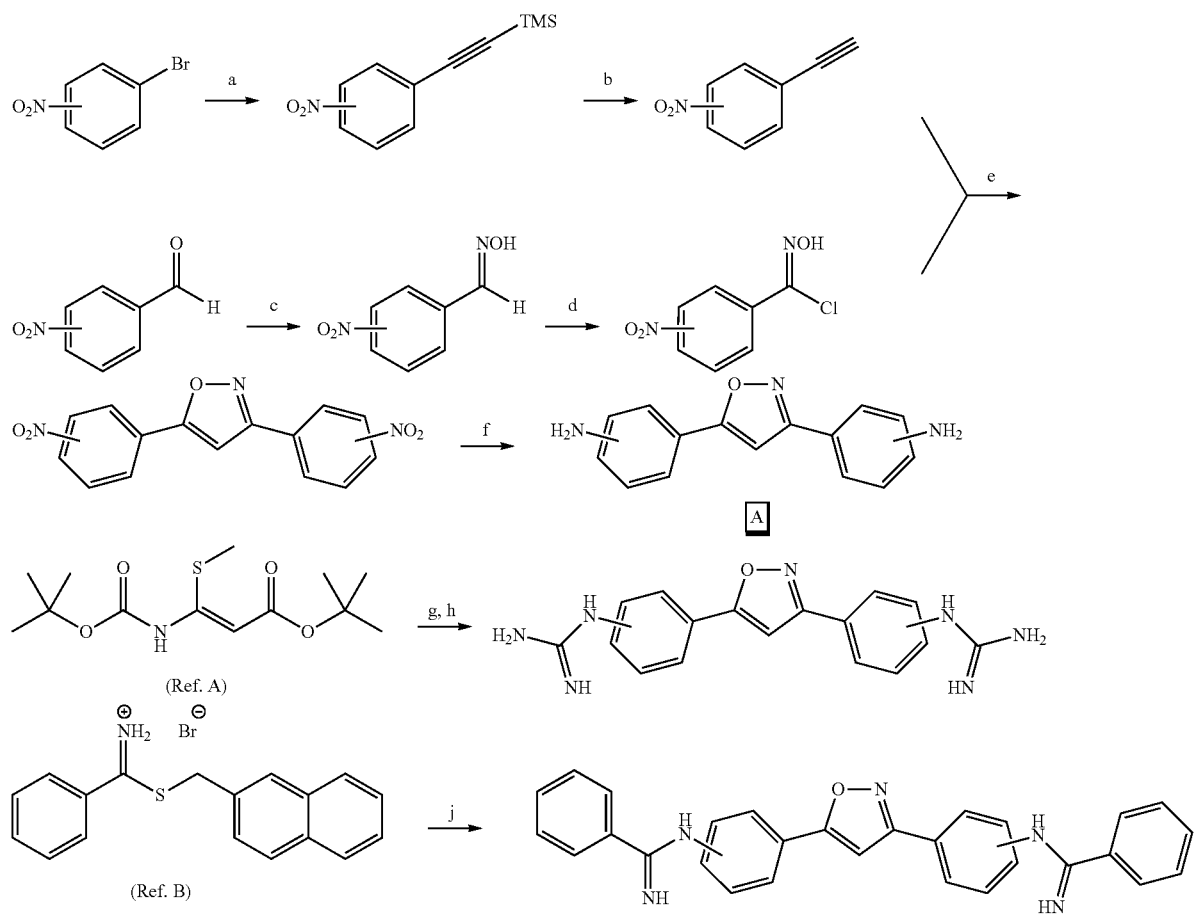

Scheme 5

Reagents and conditions:
a TMSA, Pd₂Cl(PPh₃)₂, CuI, Et₃N;
b Cs₂CO₃, aq. CH₃CN;
c NH₂OH·HCl, H₂O/EtOH;
d NCS, DMF;
e (Bu₃Sn)₂O, CH₂Cl;
f H₂, 10% Pd/C, EtOH;
g compound A, TEA, Hg(Cl)₂, DMF;
h HCl, EtOH/CH₂Cl₂;
j compound A, CH₃CN, EtOH.

Ref. A: Bergeron. R. J. et al., *J. Org. Chem.*, 52(9) 1700-1703 (1987).
Ref. B: Stephens. C. E. et al., *J. Med. Chem.*, 44(11), 1741-1748 (2001).

Synthetic Methods and Supporting Analytical Data

General Procedure for Amidines 1-11 and 13-43. The nitrile was added to a mixture of anhydrous EtOH and 1,4-dioxane that had been saturated with hydrogen chloride at 0° C. in a dry 3-neck flask equipped with a gas inlet tube, a thermometer, and a drying tube, and cooled in an ice-salt bath. The reaction mixture was then sealed, slowly warmed to ambient temperature, and stirred until the nitrile was no longer detectable. The reaction mixture was diluted with ether. The crude imidate was filtered off under inert gas and dried under high vacuum over KOH. The imidate (or an aliquot thereof) was then reacted immediately with the appropriate ammonia or the appropriate amine in EtOH. The reaction mixture was diluted with ether, and the crude amidine was filtered off. Compounds 3-9, 11, 13-18, 20-21, 23-24, 27, 29, 31, 33, 35-46, 38, and 42-43 were purified by preparative HPLC and were converted to their dihydrochloride salts using aqueous or ethanol HCl. Other compounds were purified directly using similar, or other solvents as stated.

5-(4-Amidinophenyl)-3-phenylisoxazole hydrochloride (1) was prepared from 5-(4-cyanophenyl)-3-phenylisoxazole, see Chrisope, D. R. et al., *J. Heterocylic Chem.*, 18(4), 795-798 (1981), (1.70 g, 6.90 mmol) following the general method in benzene, to give a solid (0.82 g, 40%): mp 262-

265° C.; ¹H NMR (90 MHz) δ 9.63 (br s, 2H), 9.50 (br s, 2H), 8.08 (m, 6H), 7.82 (s, 1H), 7.60 (m, 3H). Anal. ($C_{16}H_{13}N_3O·HCl·0.2H_2O$) C, H, N.

3-(4-Amidinophenyl)-5-phenylisoxazole (2) was prepared as immediately above from 3-(4-cyanophenyl)-5-phenylisoxazole, see Chrisope. D. R. et al., *J. Heterocylic Chem.*, 18(4), 795-798 (1981), (2.10 g, 8.50 mmol) to give a solid (0.87 g, 34%): mp 287-292° C.; ¹H NMR (90 MHz) δ 9.60 (br s, 3H), 8.13 (m, 6H), 7.94 (s, 1H), 7.60 (m, 3H). Anal. ($C_{16}H_{13}N_3O·HCl·0.2H_2O$) C, H, N.

3,5-Bis(4-amidinophenyl)isoxazole dihydrochloride (3) was prepared from nitrile 50a (1.48 g, 5.47 mmol), EtOH (5 mL) and 1,4-dioxane (60 mL). See Dann. O., et al., *Liebigs Ann. Chem.*, 160-194 (1975). The crude imidate (2.31 g, 97%) was filtered off and stirred overnight in EtOH/NH₃ (50 mL) to give a white solid (0.84 g, 41%): mp>350° C. (dec., lit.), see Dann, O., et al., *Liebigs Ann. Chem.*, 160-194 (1975); ¹H NMR δ 9.55 (br s, 3H), 9.28 (br s, 3H), 8.17 (d, J=8.7 Hz, 4H), 8.05 (d, J=8.1 Hz, 2H), 8.04 (d, J=8.7 Hz, 2H), 8.04 (s, 1H); MS m/z 306 (MH⁺ of free base); HPLC (Method A) $t_R$ 3.96 min (100 area % at 265 nm). Anal. ($C_{17}H_{15}N_5O·2HCl$) C, H, N, Cl.

3,5-Bis[4-(N-isopropyl)amidinophenyl]isoxazole dihydrochloride (4) was prepared from nitrile 50a (2.18 g, 8.05 mmol). An aliquot of the crude imidate (1.20 g, 2.78 mmol) was reacted with isopropylamine (2.2 mL, 26 mmol) in EtOH (25 mL) overnight to give a white powder (0.51 g, 40%): mp 304-307° C.; ¹H NMR δ 9.78 (m, 2H), 9.62 (br s, 2H), 9.28 (br s, 2H), 8.16 (d, J=8.3 Hz, 4H), 8.04 (s, 1H), 7.96 (d, J=8.6 Hz, 2H), 7.94 (d, J=8.5 Hz, 2H), 4.12 (m, 2H), 1.30 (d J=6.5 Hz, 2H); MS m/z 390 (MH⁺ of free base); HPLC (Method A) $t_R$ 6.06 min (100 area % at 265 nm). Anal. ($C_{23}H_{27}N_5O·2HCl·2.75H_2O$) C, H, N, Cl.

3,5-Bis[4-(2-imidazolinyl)phenyl]isoxazole dihydrochloride (5). An aliquot of the imidate above (1.25 g, 2.86 mmol), was stirred overnight in a mixture of ethylenediamine (3 mL, 45 mmol) and EtOH (25 mL) to give a cream colored solid: (0.66 g, 54%): mp>350° C. (dec.); ¹H NMR δ 7.97 (d, J=8.5 Hz, 2H), 7.96 (d, J=8.7 Hz, 2H), 7.85 (d, J=8.7 Hz, 4H), 7.25 (s, 1H), 4.01 (s, 8H); MS m/z 358 (MH⁺ of free base); HPLC (Method A) $t_R$ 4.96 min (100 area % at 290 nm). Anal. ($C_{21}H_{19}N_5O·2HCl·0.3H_2O$) C, H, N, Cl.

5-(4-Amidino-2-nitrophenyl)-3-(4-amidinophenyl)isoxazole dihydrochloride (6) was prepared from nitrile 53a (1.57 g, 4.96 mmol) to give a white solid: (0.67 g, 32%): mp>350° C. (dec.); ¹H NMR δ 9.78 (br s, 2H), 9.60 (br s 4H), 9.37 (br s, 2H), 8.63 (s, 1H), 8.37 (d, J=8.2 Hz, 1H) 8.26 (d, J=8.1 Hz, 1H), 8.20 (d, J=8.4 Hz, 2H), 8.05 (d, J=8.0 Hz, 2H), 7.95 (s, 1H); MS m/z 351 (MH⁺ of free base); HPLC (Method A) $t_R$ 3.96 min (100 area % at 254 nm). Anal. ($C_{17}H_{14}N_6O_3·2HCl·0.5H_2O$) C, H, N, Cl.

5-(4-Amidino-2-chlorophenyl)-3-(4-amidinophenyl)isoxazole dihydrochloride (7) was prepared from nitrile 53b (1.53 g, 5.01 mmol) to give a white solid: (0.78 g, 38%): mp>350° C. (dec.); ¹H NMR δ 9.71 (br s, 2H), 9.60 (br s, 2H), 9.49 (br s, 2H), 9.38 (br s, 2H), 8.25 (m, 4H); 8.04 (m, 3H), 7.94 (s, 1H); MS m/z 340 (MH⁺ of free base); HPLC (Method A) $t_R$ 4.43 min (100 area % at 265 nm). Anal. ($C_{17}H_{14}ClN_5O·2HCl·0.4H_2O$) C, H, N, Cl.

5-(4-Amidino-2-methoxyphenyl)-3-(4-amidinophenyl)isoxazole dihydrochloride (8) was prepared from nitrile 50b (0.55 g, 1.84 g). The crude imidate was then reacted with ammonium carbonate (2.20 g, 22.90 mmol) in EtOH (30 mL) overnight to give a pale yellow solid (0.27 g, 36%): mp 336-337° C.; ¹H NMR δ9.40 (br s, 7H), 8.25 (d, J=8.2 Hz, 2H), 8.14 (d, J=8.0 Hz, 1H), 8.02 (d, J=8.5 Hz, 2H), 7.76 (d, 7.75 (d, J=0.7 Hz, 1H), 7.61 (dd, J=7.6 and 1.0 Hz, 1H), 4.14 (s. 3H), MS m/z 336 (MH⁺ of free base); HPLC (Method A) $t_R$ 4.64 min (100 area % at 265 nm). Anal. ($C_{18}H_{17}N_5O_2·2HCl·1.5H_2O$) C, H, N, Cl.

3-(4-Amidino-2-nitrophenyl)-5-(4-amidinophenyl)isoxazole dihydrochloride (9) was prepared from nitrile 53c (1.00 g, 3.17 g) to give a white solid (0.32 g, 24%): mp 350° C. (dec.); ¹H NMR δ 9.55 (br s, 7H), 8.62 (d, J=1.8 Hz, 1H), 8.33 (dd, J=8.1 and 1.9 Hz, 1H), 8.19 (d, J=8.7 Hz, 2H), 8.15 (d, J=8.1 Hz, 1H), 8.05 (d, J=8.7 Hz, 2H), 7.79 (s, 1H); MS m/z 351 (MH⁺ of free base); HPLC (Method A) $t_R$ 3.77 min (100 area % at 265 nm). Anal. ($C_{17}H_1N_6O_3·2HCl·0.5H_2O$) C, H, N, Cl.

3-(4-Amidino-2-chlorophenyl)-5-(4-amidinophenyl)isoxazole dihydrochloride (10) was prepared from nitrile 53d (1.00 g, 3.28 mmol). The crude product was dissolved in isopropyl alcohol, and the solution was diluted with ether to give a white power (0.55 g, 41%): mp 350° C. (dec.); ¹H NMR δ 9.71 (br s, 2H), 9.62 (br s, 2H), 9.49 (br s, 2H), 9.40 (br s, 2H), 8.24 (d, J=8.5 Hz, 2H), 8.21 (s, 1H), 8.06 (d, J=8.9 Hz, 2H), 8.03 (d, J=8.4 Hz, 1H), 7.98 (d, J=8.4 Hz, 1H), 7.85 (s, 1H); MS m/z 340 (MH⁺ of free base); HPLC (Method A) $t_R$ 4.29 min (100 area % at 265 nm). Anal. ($C_{17}H_{14}ClN_5O·2HCl·H_2O$) C, H, N, Cl.

3-(4-Amidino-2-methoxyphenyl)-5-(4-amidinophenyl)isoxazole dihydrochloride (11) was prepared by nitrile 53e (0.94 g, 3.16 mmol) to give a white solid (0.35 g, 28%): mp 335-337° C. (dec.); ¹H NMR δ 9.48 (br s, 8H), 8.22 (d, J=8.5 Hz, 2H), 8.04 (d, J=8.4 Hz, 2H), 8.03 (d, J=8.0 Hz, 1H), 7.76 (s. 1H). 7.73 (br s, 1H), 7.58 (dd, J=8.1 and 1.3 Hz, 1H), 4.06 (s, 3H); MS m/z 336 (MH⁺ of free base); HPLC (Method A) $t_R$ 4.25 min (100 area % at 290 nm). Anal. ($C_{18}H_{17}N_5O_2·2HCl·1.1H_2O$) C, H, N, Cl.

3,5-Bis(4-amidino-2-methoxyphenyl)isoxazole dihydrochloride (12). A mixture of N-acetoxy intermediate 55 (1.11 g, 2.31 mmol) and 10% Pd/C (0.60 g, 0.56 mmol) in ACOH and EtOH (100 mL of each) was hydrogenated at 60 psi for 2.5 h. The reaction mixture was filtered through Celite, and the filtrate was evaporated to dryness. An aliquot of the crude product (0.20 g) was suspended in EtOH (50 mL) was treated with EtOH/HCl (2 mL). A yellow solid was filtered off (0.13 g, 73% from the aliquot, 13% overall): mp>350° C. (dec.); ¹H NMR δ 9.64 (brs, 2H), 9.62 (brs, 2H), 9.34 (brs, 4H), 8.14 (d, J=8.1 Hz, 1H), 8.02 (d, J=8.0 Hz, 1H), 7.74 (s, 1H), 7.71 (s, 1H), 7.62 (d, J=8.4 Hz, 1H), 7.57 (d, J=8.1 Hz, 1H), 7.56 (s, 1H), 4.12 (s, 3H), 4.05 (s, 3H); MS m/z 366 (MH⁺ of free base); HPLC (Method A) $t_R$ 5.02 min (100 area % at 265 nm). Anal. ($C_{19}H_{19}N_5O_{30}·2HCl·1.2H_2O$) C, H, N, Cl.

3-(3-Amidinophenyl)-5-(4-amidinophenyl)isoxazole dihydrochloride (13) was prepared from nitrile 50c (2.62 g, 9.66 mmol). An aliquot (2.27 g, wet) of the imidate was treated with EtOH/NH₃ to give an off-white solid (0.19 g, 10%): mp 212-215° C. (dec.); ¹H NMR δ 9.52 (br s, 4H), 8.48 (m, 1H), 8.28 (d, J=8.1 Hz, 1H), 8.16 (d, J=8.7 Hz, 2H), 8.08 (s, 1H), 8.07 (d, J=8.7 Hz, 2H), 8.02 (d, J=8.0 Hz, 1H), 7.83 (t, J=7.8 Hz, 1H); MS m/z 306 (MH⁺ of free base); HPLC (Method A) $t_R$ 3.99 min (100 area % at 290 nm). Anal. ($C_{17}H_{15}N_5O·2HCl·H_2O$) C, H, N, Cl.

3-[3-(N-Isopropyl)amidinophenyl]-5-[4-(N-isopropyl)amidinophenyl]-isoxazole dihydrochloride (14) was prepared by treatment of an aliquot (2.16 g, wet) of the above imidate with isopropylamine to give a pale yellow crystals (0.85 g, 37%): mp>350° C.; ¹H NMR δ 9.75 (br s, 6H), 8.37 (s, 1H), 8.25 (d, J=7.8 Hz, 1H), 8.13 (d, J=8.4 Hz, 2H), 8.13 (s, 1H), 7.98 (d, J=8.5 Hz, 2H), 7.94 (d, J=8.0 Hz, 1H), 7.80 (t, J=7.8 Hz, 1H), 4.19 (m, 2H), 1.32 (d, J=6.2 Hz, 1H), 1.31 (d, J=6.1 Hz, 1H); MS m/z 390 (MH⁺ of free base); HPLC (Method A) $t_R$ 5.92 min (99.0 area % at 265 nm). Anal. ($C_{23}H_{27}N_5O·2HCl·H_2O$) C, H, N, Cl.

3-[3-(2-Imidazolinyl)phenyl]-5-[4-(2-imidazolinyl)phenyl]isoxazole dihydrochloride (15) was prepared by prepared by treatment of an aliquot (1.80 g, wet) of the imidate used in the preparation of 13 with ethylenediamine to give a yellow solid (0.80 g, 45%). mp 248-251° C. (dec.); $^1$H NMR δ 8.85 (m, 1H), 8.27 (m, 4H), 8.15 (m, 3H), 7.86 (t, J=8.0 Hz, 1H), 4.05 (s, 1H), 4.03 (s, 1H); MS m/z 358 (MH$^+$ of free base); HPLC (Method A) $t_R$ 4.96 min (100 area % at 290 nm). Anal. ($C_{21}H_{19}N_5O.2HCl.1.5H_2O$) C, H, N, Cl.

5-(4-Amidino-2-nitrophenyl)-3-(3-amidinophenyl)isoxazole dihydrochloride (16) was prepared from nitrile 53g (0.50 g, 1.58 mmol) to give a white solid (0.14 g, 21%): mp 225-225° C.; $^1$H NMR δ 9.84 (br s, 2H), 9.64 (br s, 2H), 9.59 (br s, 2H), 9.37 (br s, 2H), 8.63 (d, J=1.8 Hz, 1H); 8.46 (m, 1H), 8.36 (dd, J=8.1 and 1.8 Hz, 1H), 8.30 (dm, J=8.1 Hz, 1H), 8.24 (d, J=8.1 Hz, 1H), 8.02 (dm, J=8.0 Hz, 1H), 7.92 (s, 1H), 7.84 (t, J=7.8 Hz, 1H); MS m/z 351 (MH$^+$ of free base); HPLC (Method A) $t_R$ 4.11 min (100 area % at 230 nm). Anal. ($C_{17}H_1N_6O_3.2HCl.1.2H_2O$) C, H, N, Cl.

5-(4-Amidino-2-chlorophenyl)-3-(3-amidinophenyl)isoxazole dihydrochloride (17) was prepared from nitrile 53h to give a white solid (0.16 g, 23%): mp 242-245° C.; $^1$H NMR δ 9.72 (br s, 2H), 9.67 (br s, 2H), 9.49 (br s, 2H), 9.40 (br s, 2H), 8.54 (m, 1H), 8.36 (dm, J=8.0 Hz, 1H), 8.25 (d, J=8.0 Hz, 1H), 8.24 (d, J=8.0 Hz, 1H), 8.06 (s, 1H), 8.04 (m, 1H), 8.02 (m, 1H), 7.83 (t, J=7.9 Hz, 1H); MS m/z 340 (MH$^+$ of free base); HPLC (Method A) $t_R$ 4.52 min (100 area % at 230 nm). Anal. ($C_{17}H_{14}ClN_5O.2HCl.0.2H_2O$) C, H, N, Cl.

5-(4-Amidino-2-methoxyphenyl)-3-(3-amidinophenyl)isoxazole dihydrochloride (18) was prepared from nitrile 50d (0.67 g, 2.47 mmol) to give a white solid (0.12 g, 14%): mp 241-246° C.; $^1$H NMR δ 9.67 (br s, 4H), 9.37 (br s, 4H), 8.50 (s, 1H), 8.34 (d, J=8.0 Hz, 1H), 8.15 (d, J=8.2 Hz, 1H), 8.01 (d, J=7.8 Hz, 1H), 7.83 (s, 1H), 7.82 (t, J=7.9 Hz, 1H), 7.76 (d, J=1.8 Hz, 1H), 7.62 (dd, J=8.2 and 1.8 Hz, 1H), 4.16 (s, 3H); MS m/z 336 (MH$^+$ of free base); HPLC (Method A) $t_R$ 3.92 min (100 area % at 230 nm). Anal. ($C_{18}H_{17}N_5O.2HCl.1.3H_2O$) C, H, N, Cl.

3-(5-Amidino-2-nitrophenyl)-5-(4-amidinophenyl)isoxazole dihydrochloride (19) was prepared from nitrile 50e (1.18 g, 3.73 mmol) to give a white solid (0.15 g, 12%): mp 238-240° C.; $^1$H NMR δ 9.85 (br s, 1H), 9.60 (br s, 3H), 9.35 (br s, 1H), 8.43 (d, J=1.9 Hz, 1H), 8.37 (d, J=8.4 Hz, 1H), 8.25 (dd, J=8.5 and 2.0 Hz, 1H), 8.15 (d, J=8.6 Hz, 2H), 8.06 (d, J=8.7 Hz, 2H), 7.88 (s, 1H); MS m/z 351 (MH$^+$ of free base); HPLC (Method A) $t_R$ 4.05 min (100 area % at 265 nm). Anal. ($C_{17}H_1N_6O_2.2HCl.1.45H_2O$) C, H, N, Cl.

3-(5-Amidino-2-chlorophenyl)-5-(4-amidinophenyl)isoxazole dihydrochloride (20) was prepared from nitrile 53j (0.41 g, 1.35 mmol) to give a white solid (0.18 g, 33%): mp 348° C.; $^1$H NMR δ 9.68 (brs, 2H), 9.61 (brs, 2H), 9.40 (br s, 4H), 8.28 (br s, 1H), 8.21 (d, J=8.5 Hz, 2H), 8.06 (d, J=8.2 Hz, 2H), 8.05 (dd, J=8.5 and 1.9 Hz, 1H), 7.99 (d, J=8.5 Hz, 1H), 7.89 (s, 1H); MS m/z 40 (MH$^+$ of free base); HPLC (Method A) $t_R$ 4.55 min (100 area % at 265 nm). Anal. ($C_{17}H_{14}ClN_5O.2HCl.0.7H_2O$) C, H, N, Cl.

3-(5-Amidino-2-methoxyphenyl)-5-(4-amidinophenyl)isoxazole dihydrochloride (21) was prepared from nitrile 50f (0.90 g, 2.99 mmol) to give a white solid (0.25 g, 22%): mp 272-275° C.; $^1$H NMR δ 9.40 (br s, 7H), 8.34 (d, J=2.6 Hz, 1H), 8.21 (d, J=8.7 Hz, 2H), 8.08 (dd, J=8.9 and 2.6 Hz, 1H), 8.05 (d, J=8.1 Hz, 2H), 7.77 (s, 1H), 7.49 (d, J=9.1 Hz, 1H), 4.05 (s, 3H); MS m/z 336 (MH$^+$ of free base); HPLC (Method A) $t_R$ 4.31 min (100 area % at 290 nm). Anal. ($C_{18}H_{17}N_5O_2.2HCl.0.8H_2O$) C, H, N, Cl.

3-(4-Amidinophenyl)-5-(3-amidinophenyl)isoxazole dihydrochloride (22) was prepared from nitrile 50g (1.25 g, 4.61 mmol) to give a white solid (1.02 g, 58%): mp 336-338° C.; $^1$H NMR δ 9.53 (br s, 8H), 8.48 (br s, 1H), 8.26 (d, J=7.7 Hz, 1H), 8.15 (d, J=8.8 Hz, 2H), 8.05 (d, J=8.8 Hz, 2H), 8.03 (d, J=7.7 Hz, 1H), 8.01 (s, 1H), 7.85 (dd, J=7.7 and 7.7 Hz, 1H); HPLC (Method A) $t_R$ 4.09 min (100 area % at 265 nm). Anal. ($C_{17}H_{15}N_5O.2HCl.2.3H_2O$) C, H, N, Cl.

3-[4-(N-Isopropyl)amidinophenyl]-5-[3-(N-isopropyl)amidinophenyl]-isoxazole dihydrochloride (23) was prepared from nitrile 50g (0.35 g, 1.28 mmol) to give a white solid (0.22 g, 38%): mp 340-343° C. dec; $^1$H NMR δ 9.90 (d, J=8.4 Hz, 1H), 9.82 (d, J=7.9 Hz, 1H), 9.73 (brs, 1H), 9.66 (brs, 1H), 9.41 (brs, 1H), 9.35 (brs, 1H), 8.35 (brs, 1H), 8.25 (d, J=7.8 Hz, 1H), 8.14 (d, J=7.9 Hz, 2H), 8.03 (s, 1H), 7.95 (d, J=7.9 Hz, 2H), 7.92 (d, J=7.8 Hz, 1H), 7.82 (dd, J=7.8 and 7.8 Hz, 1H), 4.15 (m, 2H), 1.31 (d, J=6.6 Hz, 6H), 1.30 (d, J=6.6 Hz, 6H); HPLC (Method A) $t_R$ 5.97 min (100 area % at 254 nm). Anal. ($C_{23}H_{27}N_5O.2HCl.1.2H_2O$) C, H, N, Cl.

3-[4-(2-Imidazolinyl)phenyl]-5-[3-(2-imidazolinyl)phenyl]isoxazole dihydrochloride (24) was prepared from nitrile 48g (0.35 g, 1.28 mmol) to give a white solid (0.39 g, 70.%): mp 315-317° C. dec; $^1$H NMR δ 10.92 (br s, 4H), 8.75 (brs, 1H), 8.30 (d, J=7.7 Hz, 1H), 8.21 (s, 4H), 8.17 (d, J=7.7 Hz, 1H), 7.99 (brs, 2H), 7.91 (dd, J=7.7 and 7.7 Hz, 1H), 4.06 (m, 8H); HPLC (Method A) $t_R$ 5.01 min (100 area % at 265 nm). Anal. ($C_{21}H_{19}N_5O.2HCl.2H_2O$) C, H, N, Cl.

5-(5-Amidino-2-chlorophenyl)-3-(4-amidinophenyl)isoxazole dihydrochloride (25) was prepared from nitrile 53k (0.72 g, 2.36 mmol) to give a white solid (0.48 g, 50%): mp 356-358° C. dec; $^1$H NMR δ 9.75 (br s, 2H), 9.63 (br s, 2H), 9.49 (br s, 2H), 9.41 (br s, 2H), 8.49 (br s, 1H), 8.25 (m, 2H), 8.10-7.95 (m, 5H); HPLC (Method A) $t_R$ 4.67 min (100 area % at 254 nm). Anal. ($C_{17}H_{14}ClN_5O.2HCl.1H_2O$) C, H, N, Cl.

5-(5-Amidino-2-methoxyphenyl)-3-(4-amidinophenyl)isoxazole dihydrochloride (26) was prepared from nitrile 50h (0.85 g, 2.82 mmol) to give a white solid (0.85 g, 74%): mp 240-242° C.; $^1$H NMR δ 9.46 (br s, 8H), 8.46 (d, J=2.2 Hz, 1H), 8.24 (d, J=8.8 Hz, 2H), 8.07 (dd, J=8.8 and 2.2 Hz, 1H), 8.04 (d, J=8.8 Hz, 2H), 7.73 (s, 1H), 7.52 (d, J=8.8 Hz, 1H), 4.14 (s, 3H); HPLC (Method A) $t_R$ 4.50 min (100 area % at 265 nm). Anal. ($C_{18}H_{17}N_5O_2.2HCl.3.1H_2O$) C, H, N, Cl.

3-(4-Amidino-2-nitrophenyl)-5-(3-amidinophenyl)isoxazole dihydrochloride (27) was prepared from nitrile 53l (0.78 g, 2.47 mmol) to give a white solid (0.26 g, 25%): mp 236° C. dec; $^1$H NMR δ 10.0-9.20 (br s, 8H), 8.63 (s, 1H), 8.48 (s, 1H), 8.35 (d, J=8.2 Hz, 1H), 8.28 (d, J=7.7 Hz, 1H), 8.14 (d, J=8.2 Hz, 1H), 8.02 (d, J=7.7 Hz, 1H), 7.85 (dd, J=8.2 and 8.2 Hz, 1H), 7.73 (s, 1H); HPLC (Method A) $t_R$ 3.92 min (100 area % at 254 nm). Anal. ($C_{17}H_{14}N_6O_3.2HCl.0.8H_2O$) C, H, N, Cl.

3-(4-Amidino-2-chlorophenyl)-5-(3-amidinophenyl)isoxazole dihydrochloride (28) was prepared from nitrile 53m (0.77 g, 2.47 mmol) to give a white solid (0.34 g, 33%): mp 210° C. dec; $^1$H NMR δ 9.58 (br s, 8H), 8.54 (s, 1H), 8.32 (d, J=7.7 Hz, 1H), 8.21 (s, 1H), 8.03 (d, J=7.7 Hz, 1H), 8.02 (d, J=8.2 Hz, 1H), 7.99 (d, J=8.2 Hz, 1H), 7.85 (dd, J=8.2 and 8.2 Hz, 1H), 7.80 (s, 1H); HPLC (Method A) $t_R$ 4.41 min (100 area % at 254 nm). Anal. ($C_{17}H_{14}ClN_5O.2HCl.1.1H_2O$) C, H, N, Cl.

3-(4-Amidino-2-methoxyphenyl)-5-(3-amidinophenyl)isoxazole dihydrochloride (29) was prepared from nitrile 53n (1.00 g, 3.32 mmol) to give a white solid (0.29 g, 22%): mp 288° C. dec; $^1$H NMR δ 9.69 (br s, 4H), 9.43 (br s, 4H), 8.52 (s, 1H), 8.30 (d, J=7.7 Hz, 1H), 8.03 (d, J=8.2 Hz, 1H), 8.00 (d, J=7.7 Hz, 1H), 7.82 (dd, J=7.7 and 7.7 Hz, 1H), 7.74 (s, 2H), 7.59 (d, J=8.2 Hz, 1H), 4.08 (s, 3H); HPLC (Method A) $t_R$ 4.42 min (100 area % at 265 nm). Anal. ($C_{18}H_{17}N_5O_2.2HCl.1H_2O$) C, H, N, Cl.

5-(5-Amidino-2-methoxyphenyl)-3-(4-amidino-2-nitrophenyl)isoxazole dihydrochloride (30) was prepared from nitrile 53o (0.70 g, 2.03 mmol) to give a white solid (0.10 g, 11%): mp 260° C. dec; $^1$H NMR δ 9.70-9.20 (br s, 8H), 8.62 (s, 1H), 8.48 (d, J=1.6 Hz, 1H), 8.34 (d, J=8.2 Hz, 1H), 8.19 (d, J=8.2 Hz, 1H), 8.10 (dd, J=8.8 and 1.6 Hz, 1H), 7.52 (d, J=8.8 Hz, 1H), 7.48 (s, 1H), 4.10 (s, 3H); HPLC (Method A) $t_R$ 4.51 min (100 area % at 254 nm). Anal. ($C_{18}H_{16}N_6O_4$.2HCl.0.8$H_2$O) C, H, N, Cl.

3-(4-Amidino-2-methoxyphenyl)-5-(5-amidino-2-methoxyphenyl)isoxazole dihydrochloride (31) was prepared from nitrile 53p (0.78 g, 2.35 mmol) to give a white solid (0.36 g, 35%): mp 330° C. dec; $^1$H NMR δ 9.63 (br s, 2H), 9.48 (br s, 2H), 9.34 (br s, 2H), 9.18 (br s, 2H), 8.44 (d, J=2.2 Hz, 1H), 8.06 (dd, J=8.9 and 2.2 Hz, 1H), 8.02 (d, J=8.1 Hz, 1H), 7.72 (d, J=1.3 Hz, 1H), 7.57 (dd, J=8.1 and 1.3 Hz, 1H), 7.52 (d, J=8.9 Hz, 1H), 7.41 (s, 1H), 4.11 (s, 3H), 4.05 (s, 3H); HPLC (Method A) $t_R$ 5.01 min (100 area % at 254 nm). Anal. ($C_{19}H_{19}N_5O_3$.2HCl) C, H, N, Cl.

3,5-Bis(3-amidinophenyl)isoxazole dihydrochloride (32) was prepared from nitrile 50i (0.58 g, 2.15 mmol) to give a white solid (0.40 g, 62%): mp 365-367° C.; $^1$H NMR δ 9.60 (br s, 4H), 9.32 (d, J=6.8 Hz, 4H), 8.42 (br s, 2H), 8.27 (d, J=7.7 Hz, 2H), 7.99 (d, J=7.7 Hz, 2H), 7.96 (s, 1H), 7.86 (t, J=7.7 Hz, 1H), 7.85 (t, J=7.7 Hz, 1H); HPLC (Method A) $t_R$ 3.92 min (98.8 area % at 254 nm). Anal. ($C_{17}H_{15}N_5O$.2HCl.2$H_2$O) C, H, N, Cl.

3,5-Bis[3-(N-isopropyl)amidinophenyl]isoxazole dihydrochloride (33) was prepared from nitrile 50i (0.58 g, 2.15 mmol) to give a white solid (0.33 g, 42%): mp 260° C. dec; $^1$H NMR δ 9.83 (br s, 2H), 9.65 (br s, 2H), 9.29 (d, J=4.1 Hz, 2H), 8.29 (br s, 2H), 8.24 (d, J=7.7 Hz, 2H), 7.98 (s, 1H), 7.86 (m, 4H), 4.09 (m, 2H), 1.31 (d, J=6.6 Hz, 12H); MS m/z 390.5 (MH$^+$ of free base); HPLC (Method A) $t_R$ 5.83 min (100 area % at 254 nm). Anal. ($C_{23}H_{27}N_5O$.2HCl.1.5$H_2$O.0.2EtOH) C, H, N, Cl.

3,5-Bis[3-(2-imidazolinyl)phenyl]isoxazole dihydrochloride (34) was prepared from nitrile 50i (0.58 g, 2.15 mmol) to give a white solid (0.37 g, 54%): mp 373-374° C.; $^1$H NMR δ 11.02 (s, 4H), 8.74 (s, 2H), 8.28 (d, J=7.1 Hz, 2H), 8.19 (d, J=7.7 Hz, 2H), 8.01 (s, 1H), 7.91 (m, 2H), 4.06 (s, 8H); HPLC (Method A) $t_R$ 5.00 min (100 area % at 254 nm). Anal. ($C_{21}H_{19}N_5O$.2HCl.0.5$H_2$O) C, H, N, Cl.

5-(5-Amidino-2-nitrophenyl)-3-(3-amidinophenyl)isoxazole dihydrochloride (35) was prepared from nitrile 50j (0.42 g, 1.33 mmol) to give a white solid (0.05 g, 9%): mp 222° C. dec; $^1$H NMR δ 9.83 (s, 2H), 9.60 (s, 2H), 9.55 (s, 2H), 9.30 (s, 2H), 8.48 (s, 1H), 8.40 (s, 1H), 8.39 (d, J=8.2 Hz, 1H), 8.26 (m, 2H), 8.00 (d, J=7.7 Hz, 1H), 7.84 (t, J=7.7 Hz, 1H), 7.82 (s, 1H); MS m/z 351 (MH$^+$ of free base); HPLC (Method A) $t_R$ 4.35 min (100 area % at 254 nm). Anal. ($C_{17}H_{14}N_6O_3$.2HCl.1$H_2$O) C, H, N, Cl.

5-(5-Amidino-2-chlorophenyl)-3-(3-amidinophenyl)isoxazole dihydrochloride (36) was prepared from nitrile 53q (0.50 g, 1.64 mmol) to give a white solid (0.33 g, 58%): mp 347° C. dec; $^1$H NMR δ 9.67 (s, 2H), 9.62 (s, 2H), 9.38 (s, 2H), 9.32 (s, 2H), 8.48 (d, J=8.8 Hz, 2H), 8.35 (d, J=7.1 Hz, 1H), 7.99 (m, 4H), 7.83 (t, J=7.7 Hz, 1H); HPLC (Method A) $t_R$ 4.68 min (100 area % at 254 nm). Anal. ($C_{17}H_{14}N_5OCl$.2HCl.0.3$H_2$O) C, H, N, Cl.

5-(5-Amidino-2-methoxyphenyl)-3-(3-amidinophenyl)isoxazole dihydrochloride (37) was prepared from nitrile 50k (0.19 g, 0.64 mmol) to give a white solid (0.12 g, 46%): mp 240° C. dec; $^1$H NMR δ 9.66 (s, 2H), 9.47 (s, 2H), 9.34 (s, 2H), 9.18 (s, 2H), 8.47 (m, 2H), 8.34 (d, J=8.2 Hz, 1H), 8.06 (d, J=8.8 Hz, 1H), 8.00 (d, J=7.7 Hz, 1H), 7.81 (t, J=7.7 Hz, 1H), 7.77 (s, 1H), 7.52 (d, J=8.8 Hz, 1H), 4.12 (s, 3H); HPLC (Method A) $t_R$ 4.63 min (100 area % at 254 nm). Anal. ($C_{18}H_{17}N_5O_2$.2HCl.0.7$H_2$O) C, H, N, Cl.

3-(5-Amidino-2-nitrophenyl)-5-(3-amidinophenyl)isoxazole dihydrochloride (38) was prepared by from nitrile 50l (0.24 g, 0.76 mmol) to give a white solid (0.08 g, 25%): mp 220° C. dec; $^1$H NMR δ 9.81 (s, 2H), 9.61 (s, 2H), 9.52 (s, 2H), 9.33 (s, 2H), 8.39 (m, 3H), 8.25 (m, 2H), 8.00 (d, J=8.2 Hz, 1H), 7.87 (t, J=7.7 Hz, 1H), 7.72 (s, 1H); MS m/z 351 (MH$^+$ of free base); HPLC (Method A) $t_R$ 4.11 min (97.59 area % at 254 nm). Anal. ($C_{17}H_{14}N_6O_3$.2HCl.1$H_2$O) C, H, N, Cl.

3-(5-Amidino-2-chlorophenyl)-5-(3-amidinophenyl)isoxazole dihydrochloride (39) was prepared from nitrile 53r (0.60 g, 1.96 mmol) to give a light yellow solid (0.39 g, 48%): mp 239-140° C.; $^1$H NMR δ 9.66 (s, 4H), 9.40 (s, 4H), 8.50 (s, 1H), 8.30 (d, J=8.2 Hz, 1H), 8.26 (d, J=2.2 Hz, 1H), 8.04 (dd, J=8.2 and 2.2 Hz, 1H), 8.00 (m, 2H), 7.84 (dd, J=8.7 and 7.7 Hz, 1H), 7.80 (s, 1H); HPLC (Method A) $t_R$ 4.69 min (100 area % at 254 nm). Anal. ($C_{17}H_{14}N_5O$.2HCl.1.5$H_2$O.0.3EtOH) C, H, N, Cl.

3-(5-Amidino-2-methoxyphenyl)-5-(3-amidinophenyl)isoxazole dihydrochloride (40) was prepared from nitrile 50m (0.34 g, 1.13 mmol) to give a light yellow solid (0.15 g, 33%): mp 210° C. dec; $^1$H NMR δ 9.64 (s, 2H), 9.42 (s, 2H), 9.35 (s, 2H), 9.12 (s, 2H), 8.47 (s, 1H), 8.33 (d, J=2.2 Hz, 1H), 8.30 (d, J=8.8 Hz, 1H), 8.06 (dd, J=8.2 and 2.2 Hz, 1H), 7.98 (d, J=7.7, 2H), 7.83 (t, J=7.7 Hz, 1H), 7.71 (s, 1H), 7.50 (d, J=8.8 Hz, 1H), 4.05 (s, 3H); HPLC (Method A) $t_R$ 4.46 min (100 area % at 254 nm). Anal. ($C_{18}H_{17}N_5O_2$.2HCl.0.6$H_2$O) C, H, N, Cl.

3,5-Bis(5-amidino-2-methoxyphenyl)isoxazole dihydrochloride (41) was prepared from nitrile 53s (0.70 g, 2.11 mmol) to give a light yellow solid (0.34 g, 44%): mp 240° C. dec; $^1$H NMR δ 9.54 (s, 2H), 9.50 (s, 2H), 9.28 (s, 2H), 9.23 (s, 2H), 8.45 (d, J=2.2 Hz, 1H), 8.31 (d, J=2.2 Hz, 1H), 8.09 (dd, J=8.8 and 2.2 Hz, 2H), 7.50 (t, J=8.8 Hz, 2H), 7.43 (s, 1H), 4.11 (s, 3H), 4.03 (s, 3H); HPLC (Method A) $t_R$ 5.19 min (96.04 area % at 254 nm). Anal. ($C_{19}H_{19}N_5O_3$.2.1HCl.2.2$H_2$O) C, H, N, Cl.

3,5-Bis[5-(N-isopropyl)amidino-2-methoxyphenyl]isoxazole dihydrochloride (42) was prepared from nitrile 53s (0.70 g, 2.11 mmol) to give a white solid (0.33 g, 30%): mp 185° C. dec; $^1$H NMR δ 9.70 (m, 2H), 9.57 (d, J=10.9 Hz 2H), 9.18 (d, J=13.2 Hz, 2H), 8.31 (d, J=2.2 Hz, 1H), 8.20 (d, J=2.2 Hz, 1H), 7.95 (dd, J=8.8 and 2.2 Hz, 2H), 7.47 (d, J=8.8 Hz, 2H), 7.44 (s, 1H), 4.11 (m, 2H), 4.09 (s, 3H), 4.02 (s, 3H), 1.29 (m, 12H); HPLC (Method A) $t_R$ 7.07 min (100 area % at 254 nm). Anal. ($C_{25}H_{31}N_5O_3$.2.4HCl.1.6$H_2$O.0.2EtOH) C, H, N, Cl.

3,5-Bis[5-(2-imidazolinyl)-2-methoxyphenyl]isoxazole dihydrochloride (43) was prepared by from nitrile 53s (0.70 g, 2.11 mmol) to give a white solid (0.44 g, 42%): mp 210° C. dec; $^1$H NMR δ 10.95 (s, 2H), 10.91 (s, 2H), 8.67 (d, J=2.2 Hz, 1H), 8.54 (d, J=2.2 Hz, 1H), 8.33 (dd, J=8.8 and 2.2 Hz, 2H), 7.54 (t, J=8.8 Hz, 2H), 7.47 (s, 1H), 4.12 (s, 3H), 4.04 (s, 3H), 4.01 (s, 4H), 4.00 (s, 4H); HPLC (Method A) $t_R$ 6.16 min (100 area % at 254 nm). Anal. ($C_{23}H_{23}N_5O_3$.2.2HCl.2.5$H_2$O.0.1 EtOH) C, H, N, Cl.

4-Cyano-2-methoxybenzaldehyde (44f). A solution of silver nitrate (25.0 g, 147 mmol) in water (75 mL) was added dropwise to a solution of α,β-dibromotoluene 65 (18.22 g, 59.74 mmol) in refluxing EtOH (300 mL). The mixture was maintained at reflux for 30 min, filtered and evaporated to dryness. The residue was diluted with water and extracted into EtOAc to give a white solid (9.55 g, 99%): mp 109-111° C.; $^1$H NMR δ 10.37 (d, J=0.8 Hz, 1H), 7.82 (d, J=7.8 Hz, 1H), 7.80 (d, J=1.0 Hz, 1H), 7.54 (dm, J=7.8 Hz, 1H), 3.99 (s, 3H); HPLC (Method B) $t_R$ 3.56 min (100 area % at 254 nm). Anal. ($C_9H_7N_5O_2$) C, H, N.

General Procedure for Chalcones (46b-f,h-n and 47). A stirred solution of equimolar amounts of a benzaldehyde 44 and an acetophenone 45 in the appropriate solvent (EtOH at 25° C. unless stated otherwise) was treated dropwise with an aqueous solution of NaOH (1.2-1.5 equiv). See Suman, et al., *Indian J. Chem., Section B*, 34B, 8, 743-746 (1995). The product, which precipitated directly or after dilution of the reaction mixture with water, was filtered off and recrystallized if necessary.

1-(3-Bromophenyl)-3-(4-bromophenyl)-2-propen-1-one (46b) was prepared from aldehyde 44a and ketone 45b to give a white solid (61.2 g, 88%): mp 142-143° C.; $^1$H NMR δ 8.36 (m, 1H), 8.17 (d, J=7.9 Hz, 1H), 8.02 (d, J=15.7 Hz, 1H), 7.91 (d, J=8.6 Hz, 2H), 7.88 (m, 1H), 7.76 (d, J=15.6 Hz, 1H), 7.69 (d, J=8.4 Hz, 2H), 7.55 (t, J=7.8 Hz, 1H); HPLC (Method B) $t_R$ 9.34 min (100 area % at 265 nm). Anal. ($C_{15}H_{10}Br_2O$) C, H, Br.

1-(5-Bromo-2-nitrophenyl)-3-(4-bromophenyl)-2-propen-1-one (46c) was prepared from aldehyde 44a and ketone 45c to give a cream colored solid, (37.1, 82%): mp 169-190° C.; $^1$H NMR δ 8.16 (dm, J=8.2 Hz, 1H), 8.03 (dd, J=8.4 and 2.1 Hz, 1H), 8.01 (s, 1H), 7.74 (d, J=8.5 Hz, 2H), 7.65 (d, J=8.7 Hz, 2H), 7.45 (d, J=16.3 Hz, 1H), 7.34 (d, J=16.3 Hz, 1H); HPLC (Method B) $t_R$ 8.56 min (100 area % at 290 nm). Anal. ($C_{15}H_9Br_2NO_3$) C, H, N, Br.

1-(5-Bromo-2-methoxyphenyl)-3-(4-bromophenyl)-2-propen-1-one (46d) was prepared from aldehyde 44a and ketone 45d to give a yellow solid (14.1 g, 89%) mp 118-120° C.; $^1$H NMR δ 7.71 (m, 3H), 7.64 (d, J=8.1 Hz, 2H), 7.61 (d, J=1.8 Hz, 1H), 7.51 (d, J=15.8 Hz, 1H), 7.42 (d, J=16.0 Hz, 1H), 7.18 (d, J=8.4 Hz, 1H), 3.86 (s, 3H); HPLC (Method B) $t_R$ 9.16 min (100 area % at 290 nm). Anal. ($C_{16}H_{12}Br_2O_2$) C, H, Br.

1-(4-Bromophenyl)-3-(3-bromophenyl)-2-propen-1-one (46e) was prepared in $CH_3CN$ from aldehyde 44a and ketone 45a to give a yellow solid (14.5 g, 79%): mp 113-115° C.; $^1$H NMR ($CDCl_3$) δ 7.88 (d, J=8.3 Hz, 2H), 7.79 (dd, J=1.3 and 1.3 Hz, 1H), 7.72 (d, J=15.5 Hz, 1H), 7.65 (d, J=8.3 Hz, 2H), 7.54 (dd, J=7.7 and 1.3 Hz, 2H), 7.46 (d, J=15.5 Hz, 1H), 7.29 (dd, J=7.7 and 7.7 Hz, 1H); HPLC (Method B) $t_R$ 9.25 min (100 area % at 290 nm). Anal. ($C_{15}H_{10}Br_2O$) C, H, Br.

3-(5-Bromo-2-methoxyphenyl)-1-(4-bromophenyl)-2-propen-1-one (46f) was prepared in $CH_3CN$ from aldehyde 44d and ketone 45a to give a yellow solid (21.2 g, 54%): mp 116-118° C.; $^1$H NMR δ 8.27 (d, J=2.2 Hz, 1H), 8.12 (d, J=8.8 Hz, 2H), 7.98 (s, 2H), 7.79 (d, J=8.8 Hz, 2H), 7.54 (dd, J=8.8 and 2.2 Hz, 1H), 7.10 (d, J=8.8 Hz, 1H), 3.90 (s, 3H); HPLC (Method B) $t_R$ 9.50 min (100 area % at 290 nm). Anal. ($C_{16}H_{12}Br_2O_2$) C, H, Br.

3-(5-Bromo-2-nitrophenyl)-1-(3-bromophenyl)-2-propen-1-one (46h) was prepared in $CH_3CN$ from aldehyde 44c and ketone 45a to give a yellow solid (30.4 g, 60%): mp 155-156° C.; $^1$H NMR δ 8.49 (s, 1H), 8.37 (s, 1H), 8.20 (d, J=8.2 Hz, 1H), 8.02 (m, 3H), 7.92 (d, J=7.7 Hz, 2H), 7.57 (t, J=7.7 Hz, 1H); HPLC (Method B) $t_R$ 8.88 min (100 area % at 254 nm). Anal. ($C_{15}H_9Br_2NO_2$) C, 30H, N, Br.

3-(5-Bromo-2-methoxyphenyl)-1-(3-bromophenyl)-2-propen-1-one (46i) was prepared in $CH_3CN$ from aldehyde 44d and ketone 45a to give a yellow solid (20.0 g, 51%): mp 122-124° C.; $^1$H NMR ($CDCl_3$) δ7.95 (s, 1H), 7.85 (d, J=15.9 Hz, 1H), 7.74 (br s, 1H), 7.53 (m, 2H), 7.27 (m, 3H), 6.64 (d, J=8.8 Hz, 1H), 3.72 (s, 3H); HPLC (Method B) $t_R$ 9.46 min (100 area % at 254 nm). Anal. ($C_{16}H_{12}Br_2O_2$) C, H, Br.

1-(5-Bromo-2-nitrophenyl)-3-(3-bromophenyl)-2-propen-1-one (46j) was prepared from aldehyde 44b and ketone 45c in $CH_3CN$ to give a brown solid (19.5 g, 64%): mp 141-143° C.; $^1$H NMR δ 8.17 (d, J=8.2 Hz, 1H), 8.03 (m, 3H), 7.80 (d, J=8.2 Hz, 1H), 7.64 (d, J=8.8 Hz, 1H), 7.41 (m, 3H); HPLC (Method B) $t_R$ 8.56 min (98.62 area % at 254 nm). Anal. ($C_{15}H_9Br_2NO_3$) C, H, N, Br.

1-(5-Bromo-2-methoxyphenyl)-3-(3-bromophenyl)-2-propen-1-one (46k) was prepared at 0° C. from aldehyde 44b and ketone 45d to give a yellow solid (37.2 g, 94%): mp 109-111° C.; $^1$H NMR δ 8.01 (s, 1H), 7.78 (d, J=7.7 Hz, 1H), 7.72 (dd, J=7.7 Hz and 2.2 Hz, 1H), 7.63 (m, 2H), 7.47 (d, J=6.6 Hz, 2H), 7.40 (t, J=7.7 Hz, 1H), 7.19 (s, J=8.8 Hz, 1H), 3.86 (s, 3H); HPLC (Method B) $t_R$ 9.18 min (100 area % at 254 nm). Anal. ($C_{16}H_{12}Br_2O_2$) C, H, Br.

3-(4-Cyano-2-methoxyphenyl)-1-(4-cyanophenyl)-2-propen-1-one (46m) was prepared from aldehyde 44e and ketone 44e in MeOH at 0° C. to give pale yellow crystals (0.73 g, 49%): mp 188-190° C. (MeOH); $^1$H NMR δ 8.30 (d, J=8.8 Hz, 2H), 8.22 (d, J=8.2 Hz, 1H), 8.08 (d, J=8.5 Hz, 2H), 8.07 (d, J=15.4 Hz, 1H), 8.01 (d, J=15.4 Hz, 1H), 7.64, (d, J=1.4 Hz, 1H), 7.53 (dd, J=8.0 and 1.4 Hz, 1H), 3.96 (s, 3H); HPLC (Method B) $t_R$ 7.20 min (96.0 area % at 290 nm). Anal. ($C_{18}H_{12}N_2O_2.0.5H_2O$) C, H, N.

3-(4-Cyano-2-methoxyphenyl)-1-(3-cyanophenyl)-2-propen-1-one (46n) was prepared in MeOH at 0° C. from aldehyde 44f and ketone 45f to give a white solid (2.97 g, 83%): mp 215-128° C.; $^1$H NMR δ 8.96 (s, 1H), 8.40 (d, J=8.1 Hz, 1H), 8.25 (d, J=8.0 Hz, 1H), 8.09 (m, 3H), 7.80 (t, J=7.9 Hz, 1H), 7.63 (2, 1H), 7.54 (d, J=8.2 Hz, 1H), 3.97 (s, 3H). Anal. ($C_{18}H_{12}N_2O_2.0.3H_2O$) C, H, N.

3-(5-Bromo-2-methoxyphenyl)-1,5-bis(3-bromophenyl)pentane-1,5-dione (47) was prepared from aldehyde 44d and ketone 45b. An oil precipitated after the reaction mixture was cooled to 0° C., and the solvent was decanted. Column chromatography [hexanes/EtOAc (9:1)] gave a solid (10.2 g, 36%): mp 91-93° C. (EtOH, ether); $^1$H NMR δ 8.10 (s, 2H), 7.95 (d, J=7.7 Hz, 2H), 7.84 (d, J=7.7 Hz, 2H), 7.50 (m, 3H), 7.31 (d, J=7.7 Hz, 1H), 6.87 (d, J=7.7 Hz, 1H), 4.17 (s, 3H), 3.40 (m, 4H); HPLC (Method B) $t_R$ 10.71 min (100 area % at 230 nm). Anal. ($C_{24}H_{19}Br_3O_3$) C, H, Br.

General Procedure for 2,3-dibromo-1,3-diphenylpropan-1-ones (48 b-n). A solution of bromine (ca. 1.1-1.3 equiv) in $CHCl_3$ was added dropwise to a solution or suspension of a chalcone 46 in $CHCl_3$ at 0° C. The mixture was stirred at room temperature until the reaction was complete. Unless stated otherwise, the solvent was evaporated and the product was recrystallized from an appropriate solvent.

2,3-Dibromo-1-(3-bromophenyl)-3-(4-bromophenyl)propan-1-one (48b) was prepared, after washing with ether, as a white solid (69.5 g, 81%): mp 158° C.; $^1$H NMR δ 8.53 (m, 1H), 8.27 (d, J=8.0 Hz, 1H), 7.99 (dm, J=7.9 Hz, 1H), 7.84 (d, J=8.5 Hz, 2H), 7.67 (d, J=8.5 Hz, 2H), 7.62 (t, J=7.9 Hz, 1H), 6.78 (d, J=11.3 Hz, 1H), 5.84 (d, J=11.2 Hz, 1H); HPLC (Method B) $t_R$ 10.32 min (100 area % at 254 nm). Anal. ($C_{15}H_{10}Br_2O$) C, H, Br.

2,3-Dibromo-1-(5-bromo-2-nitrophenyl)-3-(4-bromophenyl)propan-1-one (48c) was prepared as white crystals (15.8 g, 88%): mp 200-201° C. (EtOH); $^1$H NMR δ 8.61 (d, J=2.1 Hz, 1H), 8.17 (dd, J=8.6 and 2.0 Hz, 1H), 8.06 (d, J=8.6 Hz, 1H), 7.76 (d, J=8.5 Hz, 2H), 7.66 (d, J=8.6 Hz, 2H), 6.74 (d, J=11.3 Hz, 1H), 5.78 (d, J=11.2 Hz, 1H).

2,3-Dibromo-1-(5-bromo-2-methoxyphenyl)-3-(4-bromophenyl)propan-1-one (48d) was prepared, after washing with ether, as a white solid (14.8 g, 75%): mp 158-159° C.; $^1$H NMR δ 7.91 (d, J=1.6 Hz, 1H), 7.86 (d, J=8.4 Hz, 1H), 7.69 (d, J=8.4 Hz, 2H), 7.63 (d, J=8.5 Hz, 2H), 7.27 (d, J=8.7 Hz, 1H), 6.32 (d, J=11.3 Hz, 1H), 5.77 (d, J=11.3 Hz, 1H), 3.97 (s, 3H); HPLC (Method B) $t_R$ 10.38 min (100 area % at 230 nm). Anal. ($C_{16}H_{12}Br_2O_2$) C, H, Br.

2,3-Dibromo-1-(4-bromophenyl)-3-(3-bromophenyl)propan-1-one (48e) was prepared as a white solid (20.4 g, 98%): mp 150-152° C.; $^1$H NMR (CDCl$_3$) δ 7.95 (d, J=8.2 Hz, 2H), 7.70 (d, J=8.2 Hz, 2H), 7.67 (dd, J=1.6 and 1.6 Hz, 1H), 7.52 (dd, J=7.7 and 1.6 Hz, 1H), 7.44 (dd, J=7.7 and 1.6 Hz, 1H), 7.30 (dd, J=7.7 and 7.7 Hz, 1H), 5.66 (d, J=11.3 Hz, 1H), 5.54 (d, J=11.3 Hz, 1H); HPLC (Method B) $t_R$ 10.16 min (100 area % at 265 nm). Anal. ($C_{15}H_{10}Br_4O$) C, H, Br.

2,3-Dibromo-3-(5-bromo-2-methoxyphenyl)-1-(4-bromophenyl)propan-1-one (48f) was prepared as a white solid (28.0 g, 95%): mp 182-184° C. dec; $^1$H NMR δ 8.24 (d, J=2.2 Hz, 1H), 8.22 (d, J=8.8 Hz, 2H), 7.89 (d, J=8.8 Hz, 2H), 7.56 (dd, J=8.8 and 2.2 Hz, 1H), 7.08 (d, J=8.8 Hz, 1H), 6.77 (d, J=11.5 Hz, 1H), 6.04 (d, J=11.5 Hz, 1H), 3.92 (s, 3H); HPLC (Method B) $t_R$ 10.04 min (100 area % at 265 nm). Anal. ($C_{16}H_{12}Br_4O_2$) C, H, Br.

2,3-Dibromo-1,3-bis(3-bromophenyl)propan-1-one (48g) was prepared as a white solid (8.81 g, 98%): mp 159-160° C.; $^1$H NMR δ 8.51 (s, 1H), 8.27 (d, J=7.7 Hz, 1H), 8.17 (s, 1H), 7.99 (d, J=8.2 Hz, 1H), 7.84 (d, J=8.4, 1H), 7.61 (m, 2H), 7.43 (7, J=7.7 Hz, 1H), 6.77 (d, J=11.5 Hz, 1H), 5.83 (d, J=11.5 Hz, 1H); HPLC (Method B) $t_R$ 10.18 min (100 area % at 254 nm). Anal. ($C_{15}H_{10}Br_4O$) C, H, Br.

2,3-Dibromo-3-(5-bromo-2-nitrophenyl)-1-(3-bromophenyl)-propan-1-one (48h) was prepared as a white solid (12.9 g, 93%): mp 187-188° C.; $^1$H NMR δ 8.70 (s, 1H), 8.47 (s, 1H), 8.26 (d, J=7.7 Hz, 1H), 8.00 (m, 3H), 7.64 (t, J=7.7 Hz, 1H), 6.85 (d, J=11.0 Hz, 1H), 6.07 (d, J=11.0 Hz, 1H); HPLC (Method B) $t_R$ 9.95 min (100 area % at 254 nm). Anal. ($C_{15}H_9Br_4NO_3$) C, H, N, Br.

2,3-Dibromo-3-(5-bromo-2-methoxyphenyl)-1-(3-bromophenyl)propan-1-one (48i) was prepared as a white solid. Two recrystallizations from CHCl$_3$/EtOH (1:5) gave pure product (4.52 g, 16%): mp 135-137° C.; $^1$H NMR δ 8.48 (s, 1H), 8.24 (brs, 1H), 7.99 (d, J=7.7 Hz, 1H), 7.59 (m, 2H), 7.08 (d, J=8.8 Hz, 1H), 6.79 (d, J=11.0 Hz, 1H), 6.05 (d, J=11.0 Hz, 1H), 3.92 (s, 1H); HPLC (Method B) $t_R$ 10.30 min (100 area % at 254 nm).

2,3-Dibromo-1-(5-bromo-2-nitrophenyl)-3-(3-bromophenyl)propan-1-one (48j) was prepared as a white solid (25.1 g, 95%): mp 153-155° C.; $^1$H NMR δ 8.61 (s, 1H), 8.09 (m, 3H), 7.78 (dd, J=8.2 and 2.2 Hz, 1H), 7.57 (d, J=7.7 Hz, 1H), 7.40 (dd, J=8.2 and 7.7 Hz), 6.76 (d, J=11.0 Hz, 1H), 5.80 (d, J=11.0 Hz, 1H). Anal. ($C_{15}H_9Br_4NO_3$) C, H, N, Br.

2,3-Dibromo-1-(5-bromo-2-methoxyphenyl)-3-(3-bromophenyl)propan-1-one (48k) was prepared as a white solid (51.5 g, 100%): mp 124-126° C.; $^1$H NMR δ 8.01 (s, 1H), 7.92 (s, 1H), 7.84 (d, J=8.8 Hz, 1H), 7.73 (d, J=7.7 Hz, 1H), 7.59 (d, J=8.2 Hz, 1H), 7.40 (dd, J=8.2 and 7.7 Hz, 1H), 7.26 (d, J=8.8 Hz, 1H), 6.35 (d, J=11.5 Hz, 1H), 5.77 (d, J=11.5 Hz, 1H), 3.96 (s, 3H); HPLC (Method B) $t_R$ 10.27 min (100 area % at 254 nm). Anal. ($C_{16}H_{12}Br_4O_2$) C, H, Br.

2,3-Dibromo-1,3-bis(4-cyanophenyl)propan-1-one (48l) was prepared as a cream colored solid (5.75 g, 84%): mp 192-193° C. (EtOH, CHCl$_3$); $^1$H NMR δ 8.45 (d, J=8.7 Hz, 2H), 8.17 (d, J=8.7 Hz, 2H), 8.08 (d, J=8.5 Hz, 2H), 7.97 (d, J=8.5 Hz, 2H), 6.84 (d, J=11.3 Hz, 1H), 5.95 (d, J=11.3 Hz, 1H); HPLC (Method B) $t_R$ 7.88 min (100 area % at 254 nm). Anal. ($C_{17}H_{10}Br_2N_2O$) C, H, N, Br.

2,3-Dibromo-3-(4-cyano-2-methoxyphenyl)-1-(4-cyanophenyl)propan-1-one (48m) was prepared, after column chromatography (CHCl$_3$) as white crystals (3.20 g, 54%): mp 163-165° C. (EtOH); $^1$H NMR δ 8.43 (d, J=8.5 Hz, 2H), 8.18 (m, 3H), 7.63 (d, J=7.0 Hz, 2H), 6.84 (d, J=11.3 Hz, 1H), 6.06 (d, J=11.4 Hz, 1H), 4.00 (d, 3H); HPLC (Method B) $t_R$ 7.88 min (94.2 area % at 254 nm).

2,3-Dibromo-3-(4-cyano-2-methoxyphenyl)-1-(3-cyanophenyl)propan-1-one (48n) was prepared, after washing in ether, as a white solid (4.54 g, 98%): mp 72-75° C.; $^1$H NMR δ 8.85 (s, 1H), 8.52 (d, J=8.1 Hz, 1H), 8.27 (d, J=7.8 Hz, 1H), 8.18 (d, J=8.3 Hz, 1H), 7.89 (t, J=7.9 Hz, 1H), 7.65 (m, 2H), 6.83 (d, J=11.5 Hz, 1H), 6.06 (d, J=11.4 Hz, 1H), 4.00 (s, 3H).

General Procedure for Diphenylisoxazoles (49b-d,f-k and 50a,b,d). A mixture of a ketone 48 in EtOH (at reflux temperature unless stated otherwise) was treated with aqueous solutions of hydroxylamine hydrochloride (1.2 to 2 equiv) and sodium hydroxide (4 to 5 equiv). The mixture was immediately cooled to ambient temperature and was stirred until the reaction was complete. The crude product was filtered off and purified if necessary by column chromatography and/or recrystallization.

3-(3-Bromophenyl)-5-(4-bromophenyl)isoxazole (49b) was prepared as white crystals (9.65 g, 54%); mp 169° C.; $^1$H NMR δ 8.10 (t, J=1.9 Hz, 1H), 7.93 (dm, J=8.7 Hz, 1H), 7.85 (d, J=8.9 Hz, 2H), 7.79 (d, J=8.8 Hz, 2H), 7.76 (s, 1H), 7.75 (dm, J=8.7 Hz, 1H), 7.53 (t, J=7.9 Hz, 1H); HPLC (Method B) $t_R$ 9.95 min (100 area % at 265 nm). Anal. ($C_{15}H_9Br_2NO$) C, H, N, Br.

3-(5-Bromo-2-nitrophenyl)-5-(4-bromophenyl)isoxazole (49c) was prepared at 0-25° C. as a white solid (1.95 g, 53%): mp 184-185° C. (EtOH); $^1$H NMR δ 8.12 (d, J=1.6 Hz, 1H), 8.11 (d, J=8.8 Hz, 1H), 8.05 (dd, J=8.8 and 1.6 Hz, 1H), 7.87 (d, J=8.8 Hz, 2H), 7.81 (d, J=8.8 Hz, 2H), 7.54 (s, 1H); HPLC (Method B) $t_R$ 9.24 min (100 area % at 265 nm). Anal. ($C_{15}H_8Br_2N_2O_3$) C, H, N, Br.

3-(5-Bromo-2-methoxyphenyl)-5-(4-bromophenyl)isoxazole (49d) was prepared as a white solid (3.55 g, 33%): mp 127-159° C.; $^1$H NMR δ 7.90 (m, 3H), 7.77 (d, J=8.6 Hz, 2H), 7.69 (dm, J=9.0 Hz, 1H), 7.50 (s, 1H), 7.21 (d, J=8.2 Hz, 1H), 3.92 (s, 3H); HPLC (Method B) $t_R$ 8.89 min (100 area % at 265 nm). Anal. ($C_{16}H_{11}Br_2N_2O_2$) C, H, N, Br.

5-(5-Bromo-2-methoxyphenyl)-3-(4-bromophenyl)isoxazole (49f) was prepared at 25° C. as a white solid (9.20 g, 48%): mp 153-154° C.; $^1$H NMR δ 7.97 (d, J=2.2 Hz, 1H), 7.93 (d, J=8.8 Hz, 2H), 7.75 (d, J=8.8 Hz, 2H), 7.69 (dd, J=8.8 and 2.2 Hz, 1H), 7.50 (s, 1H), 7.24 (d, J=8.8 Hz, 1H), 4.00 (s, 3H); HPLC (Method B) $t_R$ 10.25 min (100 area % at 254 nm). Anal. ($C_{16}H_{11}Br_2NO_2$) C, H, N, Br.

3,5-Bis(3-bromophenyl)isoxazole (49g) was prepared as a white solid (2.71 g, 44%): mp 155-156° C.; $^1$H NMR δ 8.11 (d, J=7.1 Hz, 2H), 7.93 (m, 2H), 7.86 (s, 1H), 7.75 (d, J=8.2 Hz, 2H), 7.56 (m, 2H); HPLC (Method B) $t_R$ 9.81 min (100 area % at 265 nm). Anal. ($C_{15}H_9Br_2NO$) C, H, N, Br.

5-(5-bromo-2-nitrophenyl)-3-(3-bromophenyl)isoxazole (49h) was prepared as a light brown solid (7.34 g, 33%): mp 179-180° C.; $^1$H NMR δ 8.24 (s, 1H), 8.09 (m, 3H), 7.95 (d, J=7.7 Hz, 1H), 7.77 (d, J=8.8 Hz, 1H), 7.76 (s, 1H), 7.54 (t, J=7.7 Hz, 2H); HPLC (Method B) $t_R$ 9.23 min (100 area % at 265 nm). Anal. ($C_{15}H_8Br_2N_2O_3$) C, H, N, Br.

5-(5-Bromo-2-methoxyphenyl)-3-(3-bromophenyl)isoxazole (49i) was prepared as a white solid (2.01 g, 60%): mp 156° C.; $^1$H NMR δ 8.18 (s, 1H), 8.00 (d, J=8.8 Hz, 1H), 7.99 (s, 1H), 7.73 (m, 2H), 7.57 (s, 1H), 7.51 (t, J=8.2 Hz, 1H) 7.25 (d, J=8.8 Hz, 1H), 4.01 (s, 3H); HPLC (Method B) $t_R$ 10.09 min (100 area % at 265 nm). Anal. ($C_{16}H_{11}Br_2NO_2$) C, H, N, Br.

3-(5-Bromo-2-nitrophenyl)-5-(3-bromophenyl)isoxazole (49j) was prepared as a yellow solid (1.01 g, 5.4%): mp 195-197° C.; $^1$H NMR δ 8.13 (m, 2H), 8.08 (m, 2H), 7.93 (d, J=7.7 Hz, 1H), 7.77 (d, J=7.7 Hz, 1H), 7.61 (s, 1H), 7.55 (t, J=0.7.7 Hz, 1H); HPLC (Method B) $t_R$ 9.25 min (96.9 area % at 265 nm). Anal. ($C_{15}H_8Br_2N_2O_3$) C, H, N, Br.

3-(5-Bromo-2-methoxyphenyl)-5-(3-bromophenyl)isoxazole (49k) was prepared as a white solid (5.71 g, 35%): mp 149-150° C.; $^1$H NMR δ 8.19 (s, 1H), 7.96 (d, J=7.7 Hz, 1H), 7.91 (s, 1H), 7.72 (m, 2H), 7.59 (s, 1H), 7.53 (t, J=8.8 Hz, 1H), 7.21 (d, J=8.8 Hz, 1H), 3.93 (s, 1H); HPLC (Method B) $t_R$ 9.93 min (100 area % at 265 nm). Anal. ($C_{16}H_{11}Br_2NO_2$) C, H, N, Br.

1,3-Bis(4-cyanophenyl)isoxazole (50a) was prepared from ketone 48l at 25° C. as a white solid (0.15 g, 56%), mp 247° C. (lit. 248-250°), see Dann. O., et al., *Liebigs Ann. Chem.*, 160-194 (1975). $^1$H NMR δ 8.09 (m, 8H), 7.96 (s, 1H); HPLC (Method B) $t_R$ 6.98 min (100 area % at 265 nm). Anal. ($C_{17}H_9N_3O$) C, H, N.

The compound also was prepared by the general method for compounds 53 below from phenylacetylene 51a and chlorooxime 52a as a white solid (3.60 g, 54%) whose NMR spectrum matches that above.

5-(4-Cyano-2-methoxyphenyl)-3-(4-cyanophenyl)isoxazole (50b) was prepared from ketone 48m in MeOH at 0-5° C. Column chromatography (CHCl$_3$) afforded white crystals (0.57 g, 20%): mp 254-255° C. (acetone); $^1$H NMR δ 8.20 (d, J=8.5 Hz, 2H), 8.08 (d, J=8.1 Hz, 1H), 8.04 (d, J=8.7 Hz, 2H), 7.79 (d, J=1.1 Hz, 1H), 7.73 (s, 1H), 7.61 (dd, J=8.1 and 1.2 Hz, 1H), 4.08 (s, 3H); HPLC (Method B) $t_R$ 7.78 min (95.5 area % at 265 nm). Anal. ($C_{18}H_{11}N_5O_2$) C, H, N.

The compound also was prepared from phenylacetylene 51g and chlorooxime 52a by the general method for compounds 53 below as a white solid (4.86 g, 65%): mp 247-250° C.; HPLC (Method A) $t_R$ 7.75 min (94.7 area % at 265 nm).

5-(4-Cyano-2-methoxyphenyl)-1-(3-cyanophenyl)isoxazole (50d) was prepared from ketone 48n in MeOH at 0° C. as a yellow solid (1.16 g, 58%): mp 242-244° C. (EtOH); $^1$H NMR δ 8.50 (s, 1H), 8.34 (dm, J=7.9 Hz, 1H), 8.08 (d, J=8.1 Hz, 1H), 8.02 (d, J=7.9 Hz, 1H), 7.77 (m, 3H), 7.61 (dd, J=8.2 and 1.4 Hz, 1H), 4.09 (s, 3H). Anal. ($C_{18}H_{11}N_3O_2$) C, H, N.

General Procedure for Isoxazole Dinitriles (50c,f-j,l,m and 53j). A dibromoisoxazole 49 was reacted with an excess of CuCN in refluxing DMF until the reaction was complete. See Friedman, L., et al., *J. Org. Chem.*, 26, 2522-2524 (1961). The reaction mixture, after successive treatments with ethylenediamine and sodium cyanide solutions, was extracted into an appropriate solvent. The product was purified by column chromatography, then recrystallized if needed.

5-(4-Cyanophenyl)-3-(3-cyanophenyl)isoxazole (50c) was prepared by from bromoisoxazole 49b to give yellow crystals (4.72 g, 69%): mp 218° C. (EtOH/toluene); $^1$H NMR δ 8.38 (m, 1H) 8.26 (dm, J=7.9 Hz, 1H), 8.08 (s, 4H), 8.04 (dm, J=7.9 Hz, 1H), 7.92 (s, 1H), 7.80 (t, J=7.8 Hz, 1H); HPLC (Method B) $t_R$ 6.99 min (100 area % at 265 nm). Anal. ($C_{17}H_9N_3O$) C, H, N.

3-(5-cyano-2-nitrophenyl)-5-(4-cyanophenyl)isoxazole (50e) was prepared from bromoisoxazole 49c using Zn(CN)$_2$ (1.0 equiv) and Pd(PPh$_3$)$_4$ (8 mol %), see Tschaen, D. M., et al., *Synth. Commun.*, 24(6), 887-890 (1994), instead of CuCN, to give a white solid (1.38 g, 37%): mp>260° C.; $^1$H NMR δ 8.49, (m, 1H), 8.35 (m, 2H), 8.10 (m, 4H), 7.77 (s, 1H); HPLC (Method B) $t_R$ 6.73 min (100 area % at 265 nm). Anal. ($C_{17}H_8N_4O_3.0.25H_2O$) C, H, N.

3-(5-Cyano-2-methoxyphenyl)-5-(4-cyanophenyl)isoxazole (50f) was prepared from bromoisoxazole 49d to give white crystals (1.06 g, 42%): mp 243-244° C. (EtOH); $^1$H NMR δ 8.20 (m, 1H), 8.16 (d, J=8.2 Hz, 2H), 8.06 (d, J=8.0 Hz, 2H), 8.02 (m, 1H), 7.71 (s, 1H), 7.43 (d, J=8.4 Hz, 1H), 4.02 (s, 3H); HPLC (Method B) $t_R$ 6.99 min (100 area % at 265 nm). Anal. ($C_{18}H_{11}N_3O_2$) C, H, N.

3-(4-Cyanophenyl)-5-(3-cyanophenyl)isoxazole (50g) was prepared from bromoisoxazole 49e to give white crystals (1.40 g, 33%): mp 188-190° C. (EtOH/CHCl$_3$); $^1$H NMR δ 8.42 (brs, 1H), 8.24 (d, J=7.7 Hz, 1H), 8.09 (m, 4H), 8.03 (d, J=7.7 Hz, 1H), 7.92 (s, 1H), 7.82 (dd, J=7.7 and 7.7 Hz, 1H); HPLC (Method B) $t_R$ 7.16 min (100 area % at 254 nm). Anal. ($C_{17}H_9N_3O$) C, H, N.

5-(5-Cyano-2-methoxyphenyl)-3-(4-cyanophenyl)isoxazole (50h) was prepared from bromoisoxazole 49f to give white crystals (1.00 g, 29%): mp 251-253° C. (CHCl$_3$); $^1$H NMR δ 8.31 (br s, 1H), 8.18 (d, J=8.2 Hz, 2H), 8.03 (d, J=8.2 Hz, 2H), 8.01 (d, J=8.8 Hz, 1H), 7.64 (s, 1H), 7.45 (d, J=8.8 Hz, 1H), 4.10 (s, 3H); HPLC (Method B) $t_R$ 7.40 min (100 area % at 254 nm). Anal. ($C_{18}H_{11}N_3O_2$) C, H, N.

3,5-Bis(3-cyanophenyl)isoxazole (50i) was prepared from bromoisoxazole 49g to give white crystals (1.94 g, 43%): mp 214-215° C. (hexane/CHCl$_2$); $^1$H NMR δ 8.38 (s, 1H), 8.34 (s, 1H), 8.22 (m, 2H), 8.02 (d, J=7.7 Hz, 2H), 7.91 (s, 1H), 7.80 (m, 2H); HPLC (Method B) $t_R$ 6.96 min (100 area % at 265 nm). Anal. ($C_{17}H_9N_3O$) C, H, N.

5-(5-Cyano-2-nitrophenyl)-3-(3-cyanophenyl)isoxazole (50j) was prepared from bromoisoxazole 49h to give light yellow crystals (0.53 g, 21%): mp 184-185° C. (CHCl$_3$); $^1$H NMR δ 8.58 (s, 1H), 8.41 (s, 1H), 8.36 (m, 2H), 8.27 (d, J=7.7 Hz, 1H), 8.05 (d, J=7.7 Hz, 1H), 7.83 (s, 1H), 7.80 (t, J=7.7 Hz, 1H); HPLC (Method B) $t_R$ 6.78 min (96.29 area % at 265 nm). Anal. ($C_{17}H_8N_4O_3$) C, H, N.

5-(5-Cyano-2-methoxyphenyl)3-(3-cyanophenyl)isoxazole (50k). A solution of tert-butyllithium (1.7 M solution in hexane, 6 mL, 10 mmol) was added dropwise to a stirred solution of bromoisoxazole 49i (1.00 g, 2.44 mmol) in dry THF (10 mL) maintained at −85° C. under Ar at such a rate that the reaction temperature did not exceed −75° C. The reaction mixture was maintained for 5 h. A solution of p-toluenesulfonyl cyanide (1.8 g, 10 mmol) in dry THF (10 mL) at −85° C. was added to the reaction mixture. The mixture was warmed to 25° C. and after 15 min was quenched with sat. aqueous NH$_4$OH (7 mL). After 15 min the mixture was poured into 1 M NaOH (100 mL). The mixture was extracted with EtOAc. Column chromatography (CHCl$_3$) followed by recrystallization from hexanes (1:1) afforded light yellow crystals (0.25 g, 34%): mp 235-238° C.; $^1$H NMR δ 8.50 (s, 1H), 8.34 (m, 2H), 8.03 (m, 2H), 7.77 (t, J=7.7 Hz, 1H), 7.71 (s, 1H), 7.47 (d, J=8.8 Hz, 1H), 4.11 (s, 3H); HPLC (Method B) $t_R$ 7.29 min (100 area % at 265 nm). Anal. ($C_{18}H_{11}N_3O_2$) C, H, N.

The compound also was prepared by the general method for compounds 53 below, from phenylacetylene 51g and chlorooxime 52e as a light yellow solid (1.05 g, 42%); mp 235-237° C.; HPLC (Method B) $t_R$ 7.31 min (98.1 area % at 254 nm).

3-(5-Cyano-2-nitrophenyl)-5-(3-cyanophenyl)isoxazole (50l) was prepared from bromoisoxazole 49j as light yellow crystals (0.18 g, 24%): mp 225-227° C. (CHCl$_3$); $^1$H NMR δ 8.48 (s, 1H), 8.45 (s, 1H), 8.35 (m, 2H), 8.25 (d, J=7.7 Hz, 1H), 8.05 (d, J=7.7 Hz, 1H), 7.82 (t, J=7.7 Hz, 1H), 7.70 (s, 1H); HPLC (Method B) $t_R$ 6.67 min (100 area % at 265 nm). Anal. ($C_{17}H_8N_4O_3$) C, H, N.

3-(5-Cyano-2-methoxyphenyl)-5-(3-cyanophenyl)isoxazole (50m) was prepared from bromoisoxazole 49k as light yellow crystals (1.41 g, 43%): mp 241-243° C. (CH$_2$Cl$_2$); $^1$H NMR δ 8.49 (s, 1H), 8.26 (m, 2H), 8.00 (br s, 2H), 7.78 (br s, 1H), 7.68 (br s, 1H), 7.42 (s, 1H); HPLC (Method B) $t_R$ 7.36 min (97.8 area % at 265 nm). Anal. ($C_{18}H_{11}N_3O_2$) C, H, N.

3-(2-Chloro-5-cyanophenyl)-5-(4-cyanophenyl)isoxazole (53j) was prepared by the general method for nitriles 50 above from bromoisoxazole 53i (1.90 g, 5.28 mmol). The crude product was purified by column chromatography (CHCl$_3$). Purified fractions were evaporated. The residue was suspended in ether and filtered off to give a pale yellow solid (0.44 g, 27%); mp 257-259° C.; $^1$H NMR δ 8.29 (d, J=2.1 Hz, 1H), 8.17 (d, J=8.4 Hz, 2H), 8.08 (m, 3H), 7.95 (d, J=8.4 Hz, 1H), 7.80 (s, 1H); HPLC (Method B) t$_R$ 7.55 min (92.3 area % at 265 nm). Anal. (C$_{17}$H$_8$ClN$_3$O.0.2H$_2$O) C, H, N.

General Procedure for Cyanophenylacetylenes (51 b-d,f-g).

In Method C, a solution of a silyl acetylene 61 in CH$_3$CN maintained at 0° C. was treated with an aqueous solution of a catalytic amount (0.05 to 0.1 equiv) of cesium carbonate. Products were isolated as precipitates filtered from the reaction mixtures or by extraction from concentrated reaction mixtures followed by column chromatography.

In Method D, a mixture of a protected acetylene 62 and a catalytic amount (0.1 equiv) of sodium hydride (60% dispersion in mineral oil) in toluene was heated at reflux as some of the solvent was distilled off. See Bleicher. L. S., et al., *J. Org. Chem.*, 63, 1109-1118 (1998). The reaction mixture was filtered and evaporated. Products were isolated by column chromatography as needed.

4-Ethynyl-3-nitrobenzonitrile (51 b) was prepared by Method C from 61 b. After 45 min, the reaction mixture was diluted with water to give a white granular solid (1.50 g, 95%): mp 131° C.; $^1$H NMR δ 8.70 (d, J=1.6 Hz, 1H), 8.23 (dd, J=8.2 and 1.6 Hz, 1H), 7.99 (d, J=8.2 Hz, 1H), 5.13, (s, 1H); HPLC (Method B) t$_R$ 4.34 min (100 area % at 254 nm). Anal. (C$_9$H$_4$N$_2$O$_3$) C, H, N.

3-Chloro-4-ethynylbenzonitrile (51c) was prepared by Method D from 62b to give a pale yellow solid (2.96 g, 97%): mp 138-140° C. (hexanes); $^1$H NMR δ 8.21 (d, J=1.5 Hz, 1H), 7.86 (dd, J=8.3 and 1.5 Hz, 1H), 7.81 (d, J=8.3 Hz, 1H), 4.99 (s, 1H); HPLC (Method B) t$_R$ 5.55 min (100 area % at 254 nm). Anal. (C$_9$H$_4$ClN) C, H, N, Cl.

By Method C (at 25° C.) from 61c a white solid (1.82 g, 98.6%) was obtained, identical in physical properties to that above.

4-Ethynyl-3-methoxybenzonitrile (51 d) was prepared by Method D from 62c to give, after column chromatography [hexanes/EtOAc (4:1)] white needles (9.62 g, 67%): mp 105-106° C. (hexanes); $^1$H NMR δ 7.59 (d, J=7.8 Hz, 1H), 7.57 (d, J=1.4 Hz, 1H), 7.42 (dd, J=7.8 and 1.4 Hz, 1H), 4.61 (s, 1H), 3.89 (s, 3H); HPLC (Method B) t$_R$ 4.58 min (100 area % at 254 nm). Anal. (C$_{10}$H$_7$NO) C, H, N.

4-Chloro-3-ethynyl-benzonitrile (51f) was prepared by Method C from 61e. After 5 d, reaction mixture was concentrated. Column chromatography [hexanes/EtOAc (9:1)] afforded a solid (1.07 g, 62%): mp 122-124° C.; $^1$H NMR δ 8.18 (d, J=1.6 Hz, 1H), 7.91 (dd, J=8.2 and 1.6 Hz, 1H), 7.80 (d, J=8.2 Hz, 1H), 4.83, (s, 1H); HPLC (Method B) t$_R$ 5.41 min (100 area % at 254 nm). Anal. (C$_9$H$_4$ClN) C, H, N, Cl.

By Method D from 62e (10 g, 45.5 mmol) a white solid (6.20 g, 84%) was obtained, identical in physical properties to that above.

3-Ethynyl-4-methoxybenzonitrile (51g) was prepared by Method D from 62f. Column chromatography [hexanes/EtOAc (4:1)] afforded yellow solid (15.7 g, 72%): mp 115-116° C. (hexane/EtOAc); $^1$H NMR δ 7.92 (d, J=2.1 Hz, 1H), 7.87 (dd, J=8.7 and 2.1 Hz, 1H), 7.25 (d, J=8.7 Hz, 1H), 4.46 (s, 1H), 3.92 (s, 3H); HPLC (method B) t$_R$ 4.29 min (100 area % at 254 nm). Anal. (C$_{10}$H$_7$NO) C, H, N.

The compound also was prepared by Method C from 61g. After 3 d the reaction mixture was concentrated, and the residue was extracted in EtOAc. Column chromatography [hexanes/EtOAc (7:3)] gave a solid (3.52 g, 64%): mp 103-105° C.; NMR and HPLC data identical to that above.

General Procedure for Benzaldehyde Chlorooximes (52a-d, f-h). N-Chlorosuccinimide (1.1 equiv) was added to a stirred solution of an aldoxime 75 in DMF at 0° C. See Liu. K.-C. et al., *J. Org. Chem.*, 45, 3916-3918 (1980). The mixture was stirred overnight at 25° C. The mixture poured into ice water and extracted into ether or EtOAc. The recovered material was used immediately in the next step without further purification.

4-Cyanobenzaldehye chlorooxime (52a) was prepared from oxime 75a as a cream colored solid (3.47 g, 96%): mp 146-148° C.; $^1$H NMR δ 12.89 (s, 1H), 7.96 (s, 4H); HPLC (Method B) t$_R$ 3.25 min (100 area % at 254 nm). Anal. (C$_8$H$_5$ClN$_2$O) C, H, N, Cl.

4-Cyano-2-nitrobenzaldehye chlorooxime (52b) was prepared as an oily residue (2.96 g, 105% crude): $^1$H NMR δ 13.09 (s, 1H), 8.66 (d, J=1.6 Hz, 1H), 8.31 (dd, J=8.1 and 1.6 Hz, 1H), 8.04 (d, J=8.2 Hz, 1H); HPLC (Method B) t$_R$ 3.68 min (100 area % at 265 nm).

2-Chloro-4-cyanobenzaldehye chlorooxime (52c) was prepared as an oily residue (3.11 g, 115% crude): $^1$H NMR δ 12.85 (s, 1H), 8.25 (d, J=1.6 Hz, 1H), 7.96 (dd, J=8.1 and 1.6 Hz, 1H), 7.82 (d, J=8.1 Hz, 1H); HPLC (Method B) t$_R$ 4.73 min (100 area % at 265 nm).

4-Cyano-2-methoxybenzaldehyde chlorooxime (52d) was prepared as a white solid (2.62 g, 99%): mp>150° C. (dec.); $^1$H NMR δ 12.51 (s, 1H), 7.66 (d, J=1.3 Hz, 1H), 7.57 (d, J=7.7 Hz, 1H), 7.49 (dd, J=8.1 and 1.6 Hz, 1H), 3.89 (s, 3H); HPLC (Method B) t$_R$ 4.27 min (100 area % at 265 nm). Anal. (C$_9$H$_7$ClN$_2$O$_2$) C, H, N.

5-Bromo-2-chlorobenzaldehye chlorooxime (52f) was prepared as white crystals (0.87 g, 69%): mp>80-83° C. (dec.); $^1$H NMR δ 8.21 (d, J=2.2 Hz, 1H), 7.82 (dd, J=8.7 and 2.4 Hz, 1H), 7.64 (d, J=8.8 Hz, 1H); HPLC (Method B) t$_R$ 6.53 min (100 area % at 230 nm).

2-Chloro-5-cyanobenzaldehye chlorooxime (52g) was prepared as a white solid (3.69 g, 100%): $^1$H NMR δ 11.08 (s, 1H), 8.19 (d, J=1.6 Hz, 1H), 8.03 (dd, J=8.8 and 1.6 Hz, 1H), 7.85 (d, J=8.8 Hz, 1H).

5-Cyano-2-methoxybenzaldehyde chlorooxime (52h) was prepared as a white solid (3.52 g, 71%): $^1$H NMR δ 12.46 (s, 1H), 7.98 (dd, J=8.8 and 1.6 Hz, 1H), 7.89 (d, J=1.6 Hz, 1H), 7.33 (d, J=8.8, 1H), 3.92 (s, 3H); HPLC (Method B) t$_R$ 3.88 min (89.3 area % at 265 nm).

General Procedure for Isoxazole Nitriles (53a-g,k-s). Bis (tributyltin) oxide (0.5 equiv) was added to a mixture of a benzaldehyde chlorooxime 52 (1 equiv) and a phenylacetylene 51 (minimum 1.2 equiv) in CH$_2$Cl$_2$ (or other solvent, if stated). See Moriya, O. et al., *J. Chem. Soc., Perkin Trans.*, 1, 413-417 (1994); Moriya. O. et al., *J. Chem. Soc., Chem. Commun.*, 17-18 (1991). Products were isolated as precipitates filtered from reaction mixtures or by column chromatography and were recrystallized as necessary from appropriate solvents.

3-(4-cyanophenyl)-5-(4-cyano-2-nitrophenyl)isoxazole (53a) was prepared from phenylacetylene 51b and chlorooxime 52a as an off-white solid (1.69 g, 67%); mp 280-281° C.; $^1$H NMR δ 8.78 (d, J=1.5 Hz, 1H), 8.44 (dd, J=8.1 and 1.5 Hz, 1H), 8.20 (d, J=8.1 Hz, 1H), 8.15 (d, J=8.2 Hz, 2H), 8.07 (d, J=8.1 Hz, 2H), 7.88 (s, 1H); HPLC (Method B) t$_R$ 6.87 min (97.4 area % at 254 nm). Anal. (C$_{17}$H$_8$N$_4$O$_3$) C, H, N.

3-(4-cyanophenyl)-5-(2-chloro-4-cyanophenyl)isoxazole (53b) was prepared from phenylacetylene 51c and chlorooxime 52a as a white solid (2.10 g, 71%): mp 260-262° C.; $^1$H NMR δ 8.36 (d, J=1.6 Hz, 1H), 8.22 36 (d, J=8.6 Hz, 2H), 8.18 (d, J=8.2 Hz, 1H), 8.06 (d, J=8.6 Hz, 2H), 8.06 (d, J=8.2 Hz, 1H), 7.98 (s, 1H); HPLC (Method B) $t_R$ 7.84 min (96.1 area % at 265 nm). Anal. ($C_{17}H_8ClN_3O$) C, H, N.

3-(4-cyano-2-nitrophenyl)-5-(4-cyanophenyl)isoxazole (53c) was prepared from phenylacetylene 51a and chlorooxime 52b to give, after column chromatography ($CH_2Cl_2$), a cream colored solid (2.26 g, 57%): mp 264-265° C. ($CH_3CN$); $^1H$ NMR δ 8.77 (d, J=1.5 Hz, 1H), 8.41 (dd, J=8.1 and 1.6 Hz, 1H), 8.11 (m, 5H), 7.74 (s, 1H); HPLC (Method B) $t_R$ 6.81 min (96.1 area % at 265 nm). Anal. ($C_{17}H_8N_4O_3$) C, H, N.

3-(2-Chloro-4-cyanophenyl)-5-(4-cyanophenyl)isoxazole (53d) was prepared from phenylacetylene 51a and chlorooxime 52c to give, after column chromatography ($CH_2Cl_2$) and recrystallization, a white solid (2.15 g, 56%): mp 247-248° C.; $^1H$ NMR δ 8.35 (d, J=1.5 Hz, 1H), 8.17 (d, J=8.5 Hz, 2H), 8.07 (d, J=8.7 Hz, 2H), 8.03 (dd, J=8.1 and 1.5 Hz, 1H), 7.97 (d, J=8.0 Hz, 1H), 7.81 (s, 1H); HPLC (Method B) $t_R$ 7.66 min (98.8 area % at 265 nm). Anal. ($C_{17}H_8ClN_3O$) C, H, N.

3-(4-Cyano-2-methoxyphenyl)-5-(4-cyanophenyl)isoxazole (53e) was prepared from phenylacetylene 51a and chlorooxime 52d to give, after column chromatography ($CH_2Cl_2$) white crystals (2.99 g, 80%): mp 243-244° C.; $^1H$ NMR δ 8.17 (d, J=8.8 Hz, 2H), 8.05 (d, J=8.8 Hz, 2H), 7.99 (d, J=8.0 Hz, 1H), 7.76 (d, J=1.4 Hz, 1H), 7.73 (s, 1H), 7.57 (dd, J=8.0 and 1.5 Hz, 1H), 4.00 (s, 3H); HPLC (Method B) $t_R$ 7.48 min (100 area % at 265 nm). Anal. ($C_{18}H_{11}N_3O_2$) C, H, N.

3-5-Bis(4-cyano-2-methoxyphenyl)isoxazole (53f) was prepared from phenylacetylene 51d and chlorooxime 52d (5.28 g, 25.1 mmol). The precipitated product was recrystallized from $CHCl_3$ using a Soxhlet extractor to give a white solid (6.27 g, 76%); mp 347-348° C.; $^1H$ NMR δ 8.09 (d, J=8.1 Hz, 1H), 7.98 (d, J=8.0 Hz, 1H), 7.79 (d, J=1.4 Hz, 1H), 7.76 (d, J=1.4 Hz, 1H), 7.62 (dd, J=8.1 and 1.4 Hz, 1H), 7.56 (dd, J=8.0 and 1.4 Hz, 1H), 7.43 (s, 1H), 4.05 (s, 3H), 3.98 (s, 3H). Anal. ($C_{19}H_{13}N_3O_3$) C, H, N.

3-(3-cyanophenyl)-5-(4-cyano-2-nitroxyphenyl)isoxazole (53g) was prepared from phenylacetylene 51b and chlorooxime 52e in benzene as a yellow solid (0.15 g, 83%): mp 198-199° C. (EtOH); $^1H$ NMR δ 8.78 (d, J=1.5 Hz, 1H), 8.43 (m, 2H), 8.29 (dm, J=8.5 Hz, 1H), 8.19 (d, J=8.1 Hz, 1H), 8.06 (dm, J=7.9 Hz, 1H), 7.86 (s, 1H), 7.80 (t, J=7.8 Hz, 1H); HPLC (Method B) $t_R$ 6.95 min (100 area % at 230 nm). Anal. ($C_{17}H_8N_4O_3 \cdot 0.2H_2O$) C, H, N.

3-(3-cyanophenyl)-5-(2-chloro-4-cyanophenyl)isoxazole (53h). Triethylamine (1.25 g, 12.4 mmol) was added to a mixture of phenylacetylene 51c (1.00 g, 6.19 mmol) and chlorooxime 52e (2.00 g, 11.06 mmol) in $CHCl_3$ under a $N_2$ atmosphere. See Thomsen. I., et al., *Acta Chem. Scand.* (*B*), 319-313 (1988). The reaction mixture was stirred at reflux. Following aqueous work-up of the reaction mixture, the product was purified by column chromatography ($CHCl_3$) to give a yellow solid (1.01 g, 54%): mp 146-148° C.; $^1H$ NMR δ 8.52 (s, 1H), 8.34 (m, 2H), 8.17 (d, J=8.1 Hz, 1H), 8.04 (m, 2H), 8.00 (s, 1H), 7.76 (t, J=7.9 Hz, 1H); HPLC (Method B) $t_R$ 7.94 min (100 area % at 265 nm). Anal. ($C_{17}H_8ClN_3O$) C, H, N.

3-(5-bromo-2-chlorophenyl)-5-(4-cyanophenyl)isoxazole (53i) was prepared analogously to 53h from phenylacetylene 51a and chlorooxime 52e as a yellow solid (1.78 g, 58%): mp 198-199° C. (EtOH); $^1H$ NMR δ 8.16 (d, J=8.8 Hz, 2H), 8.07 (d, J=8.6 Hz, 2H), 7.97 (d, J=2.3 Hz, 1H), 7.80 (dd, J=8.6 and 2.4 Hz, 1H), 7.78 (s, 1H), 7.66 (d, J=8.5 Hz, 1H); HPLC (Method B) $t_R$ 9.05 min (100 area % at 265 nm). Anal. ($C_{16}H_8BrClN_2O$) C, H, N, Br, Cl.

3-(4-Cyanophenyl)-5-(2-chloro-5-cyanophenyl)isoxazole (53k) was prepared from phenylacetylene 51f and chlorooxime 52a as a white solid (1.46 g, 32%); mp 207-209° C.; $^1H$ NMR δ 8.46 (d, J=1.6 Hz, 1H), 8.19 (d, J=8.2 Hz, 2H), 8.07 (dd, J=8.8 and 1.6 Hz, 1H), 8.06 (d, J=8.2 Hz, 2H), 7.95 (d, J=8.8 Hz, 1H), 7.90 (s, 1H); HPLC (Method B) $t_R$ 7.69 min (98.0 area % at 254 nm). Anal. ($C_{17}H_8ClN_3O$) C, H, N, Cl.

3-(4-Cyano-2-nitrophenyl)-5-(3-cyanophenyl)isoxazole (531) was prepared from phenylacetylene 51e and chlorooxime 52b as a white solid (3.10 g, 69%); mp 235-238° C.; $^1H$ NMR δ 8.77 (d, J=1.1 Hz, 1H), 8.47 (dd, J=1.6 and 1.6 Hz, 1H), 8.41 (dd, J=7.7 and 1.1 Hz, 1H), 8.26 (ddd, J=8.2, 1.6 and 1.6 Hz, 1H), 8.09 (d, J=8.2 Hz, 1H), 8.04 (ddd, J=7.7, 1.6 and 1.6 Hz, 1H), 7.81 (dd, J=7.7 and 7.7 Hz, 1H), 7.68 (s, 1H); HPLC (Method B) $t_R$ 6.84 min (96.6 area % at 254 nm). Anal. ($C_{17}H_8N_4O_3$) C, H, N.

3-(2-Chloro-4-cyanophenyl)-5-(3-cyanophenyl)isoxazole (53m) was prepared from phenylacetylene 51e and chlorooxime 52c as a white solid (1.16 g, 27%); mp 221-223° C.; $^1H$ NMR δ 8.51 (br s, 1H), 8.33 (br s, 1H), 8.29 (d, J=8.2 Hz, 1H), 8.03 (d, J=8.2 Hz, 1H), 8.01 (s, 1H), 7.97 (d, J=7.7 Hz, 1H), 7.81 (d, J=7.7 Hz, 1H), 7.77 (s, 1H); HPLC (Method B) $t_R$ 7.65 min (98.0 area % at 254 nm). Anal. ($C_{17}H_8ClN_3O$) C, H, N, Cl.

3-(4-Cyano-2-methoxyphenyl)-5-(3-cyanophenyl)isoxazole (53n) was prepared from phenylacetylene 51e and chlorooxime 52d as a white solid (2.66 g, 88%); mp 202-204° C.; $^1H$ NMR δ 8.46 (br s, 1H), 8.25 (d, J=7.7 Hz, 1H), 7.97 (d, J=7.7 Hz, 2H), 7.76 (dd, J=7.7 and 7.7 Hz, 1H), 7.70 (br s, 1H), 7.66 (br s, 1H), 7.54 (d, J=7.7 Hz, 1H), 3.97 (s, 3H); HPLC (Method B) $t_R$ 7.48 min (100 area % at 254 nm). Anal. ($C_{18}H_{11}N_3O_2$) C, H, N.

3-(4-Cyano-2-nitrophenyl)-5-(5-cyano-2-methoxyphenyl)isoxazole (53o) was prepared from phenylacetylene 51 g and chlorooxime 52b as a white solid (1.44 g, 47%); mp 264-266° C.; $^1H$ NMR δ 8.75 (d, J=1.1 Hz, 1H), 8.38 (dd, J=8.2 and 1.1 Hz, 1H), 8.35 (d, J=2.2 Hz, 1H), 8.15 (d, J=8.2 Hz, 1H), 8.04 (dd, J=8.8 and 2.2 Hz, 1H), 7.47 (d, J=8.8 Hz, 1H), 7.46 (br s, 1H), 4.07 (s, 3H); HPLC (Method B) $t_R$ 7.00 min (98.4 area % at 254 nm). Anal. ($C_{18}H_{10}N_4O_4$) C, H, N.

3-(4-Cyano-2-methoxyphenyl)-5-(5-cyano-2-methoxyphenyl)isoxazole (53p) was prepared from phenylacetylene 51g and chlorooxime 52d as a white solid (1.65 g, 76%); mp 271-273° C.; $^1H$ NMR δ 8.29 (br s, 1H), 7.99 (d, J=7.7 Hz, 1H), 7.96 (d, J=8.8 Hz, 1H), 7.71 (br s, 1H), 7.55 (d, J=7.7 Hz, 1H), 7.43 (d, J=8.8 Hz, 1H), 7.34 (br s, 1H), 4.06 (s, 3H), 3.96 (s, 3H); HPLC (Method B) $t_R$ 7.58 min (100 area % at 254 nm). Anal. ($C_{19}H_{13}N_3O_3$) C, H, N.

3-(3-Cyanophenyl)-5-(2-chloro-5-cyanophenyl)isoxazole (53q) was prepared from phenylacetylene 51f and chlorooxime 52e in benzene. Column chromatography ($CHCl_3$) afforded a yellow solid (1.22 g, 74%): mp 201-203° C.; $^1H$ NMR δ 8.50 (s, 1H), 8.46 (d, J=1.6 Hz, 1H), 8.33 (d, J=7.7 Hz, 1H), 8.05 (m, 2H), 7.96 (d, J=8.2 Hz, 1H), 7.93 (s, 1H), 7.78 (t, J=7.7 Hz, 1H); HPLC (Method B) $t_R$ 7.76 min (100 area % at 254 nm). Anal. ($C_{17}H_8ClN_3O$) C, H, N, Cl.

3-(2-Chloro-5-cyanophenyl)-5-(3-cyanophenyl)isoxazole (53r) was prepared from phenylacetylene 51a and chlorooxime 52g in benzene. Column chromatography ($CHCl_3$) afforded a yellow solid (2.10 g, 49%): mp 124-125° C.; $^1H$ NMR δ 8.50 (s, 1H), 8.28 (d, J=7.7 Hz, 1H), 8.27 (d, J=1.6 Hz, 1H), 8.07 (dd, J=8.2 and 1.6 Hz, 1H), 8.03 (d, J=8.2 Hz, 1H), 7.94 (d, J=8.2 Hz, 1H), 7.80 (t, J=7.7 Hz, 1H), 7.75 (s, 1H); HPLC (Method B) $t_R$ 7.55 min (98.5 area % at 254 nm). Anal. ($C_{17}H_8ClN_3O$) C, H, N, Cl.

3,5-Bis(5-cyano-2-methoxyphenyl)isoxazole (53s) was prepared from phenylacetylene 51g and chlorooxime 52h in benzene. Column chromatography ($CHCl_3$) afforded a yellow solid (4.30 g, 79%): mp 268-270° C.; $^1H$ NMR δ 8.31 (d, J=1.6 Hz, 1H), 8.18 (d, J=1.6 Hz, 1H), 8.02 (dd, J=8.8 and 1.6 Hz, 2H), 7.45 (d, J=8.8 Hz, 1H), 7.42 (d, J=8.8 Hz, 1H), 7.34 (s, 1H), 4.07 (s, 3H) 4.00 (s, 3H); HPLC (Method B) $t_R$ 7.27 min (100 area % at 254 nm). Anal. ($C_{19}H_{13}N_3O_3$) C, H, N.

3,5-Bis[4-(N-hydroxy)amidino-2-methoxyphenyl]isoxazole (54). Potassium tert-butoxide (11.2 g, 100 mmol) was added to a solution of hydroxylamine hydrochloride (7.01 g, 101 mmol) in dry DMSO 60 mL). Dinitrile 53f (3.32 g, 10.0 mmol) was added. The mixture was stirred under Ar for 12 d, with more DMSO (60 mL) added after 6 d. The reaction mixture was filtered, and the filtrate was poured into ice water to give a white precipitated solid (3.14 g, 79%): mp 203-204° C.; $^1$H NMR δ 9.87 (brs, 1H), 9.82 (brs, 1H), 7.89 (d, J=8.1 Hz, 1H), 7.79 (d, J=8.1 Hz, 1H), 7.51 (d, J=1.3 Hz, 1H), 7.47 (m, 2H), 7.42 (dd, J=8.1 and 1.5 Hz, 1H), 7.27 (s, 1H), 6.00 (br s, 2H), 5.98 (br s, 2H), 4.02 (s, 3H), 3.95 (s, 3H); HPLC (Method A) $t_R$ 6.99 min (100 area % at 265 nm). Anal. ($C_{19}H_{19}N_5O_6$.0.6$H_2$O) C, H, N.

3,5-Bis[4-(N-acetoxy)amidino-2-methoxyphenyl]isoxazole (55). Acetic anhydride (5 mL) was added to a suspension of diamidoxime (54 (1.00 g, 2.51 mmol) in glacial acetic acid (25 mL). The mixture was stirred overnight, then poured over ice to give a white solid (1.14 g, 94%): mp 238° C. (dec.); $^1$H NMR δ 7.97 (d, J=8.1 Hz, 1H), 7.87 (d, J=8.2 Hz, 1H), 7.51 (m, 3H), 7.46 (d, J=8.1 Hz, 1H), 7.33 (s, 1H), 6.98 (br s, 4H), 4.05 (s, 3H), 3.98 (s, 3H), 2.17 (s, 6H); HPLC (Method B) $t_R$ 4.08 min (96.0 area % at 265 nm). Anal. ($C_{23}H_{23}N_5O_7$) C, H, N.

4-Chloro-3-iodobenzaldoxime (59). A solution of aldehyde 58 (15.0 g, 56.3 mmol) and hydroxylamine hydrochloride (4.86 g, 69.9 mmol) in pyridine (30 mL) and dry EtOH (30 mL) was stirred overnight under Ar. The reaction mixture was concentrated to half-volume and poured into ice water to afford a white solid (12.1 g, 76%): mp 97-99° C.; $^1$H NMR δ 11.52 (s, 1H), 8.15 (d, J=1.6 Hz, 1H), 7.66 (dd, J=8.2 and 1.6 Hz, 1H), 7.59 (d, J=8.2, 1H). Anal. ($C_7H_5$ClINO) C, H, N, Cl, I.

4-Bromo-3-chlorobenzonitrile (60c). Aniline 56 (5.19 g, 26.4 mmol) was added to conc. HCl maintained below 0° C. A solution of sodium nitrite (3.67 g, 53.2 mmol) in water (10 mL) was added dropwise such that the temperature of the reaction mixture did not exceed 5° C. The mixture was maintained for 1 h, then was added to a solution of CuCl (6.55 g, 66.2 mmol) in conc. HCl (20 mL). Toluene (200 mL) was added, and the biphasic mixture was stirred at 60-80° C. for 1 h. Layers were separated, and the aqueous layer was extracted into toluene to afford a white solid (4.67 g, 82%); mp 80-81° C. (hexane); $^1$H NMR δ 9.55 (d, J=1.8 Hz, 1H), 8.03 (d, J=8.4 Hz, 1H), 7.78 (d, J=8.4 and 1.9 Hz, 1H); HPLC (Method B) $t_R$ 3.96 min (100 area % at 265 nm). Anal. ($C_7H_3$BrClN) C, H, N, Br, Cl.

3-methoxy-4-O-trifluoromethylsulfonylbenzonitrile (60d). Triethylamine (15.7 g, 155 mmol) was added to a stirred solution of 4-hydroxy-3-methoxybenzonitrile (20.0 g, 134 mmol) in dry $CH_2Cl_2$ maintained below 0° C. Triflic anhydride (47.4 g, 168 mmol) was added dropwise over 45 min such that the temperature of the reaction mixture did not exceed 5° C. The reaction mixture was maintained for 1 h, poured into ice water, and extracted into EtOAc. Column chromatography [hexane/EtOAc (9:1)], afforded colorless crystals (33.4 g, 89%): mp 51-53° C. (hexanes/EtOAC); $^1$H NMR δ 7.92 (d, J=1.9 Hz, 1H), 7.73 (d, J=8.4 Hz, 1H), 7.56 (dd, J=8.4 and 1.9 Hz, 1H), 3.97 (s, 3H); HPLC (Method B) $t_R$ 6.89 min (100 area % at 230 nm). Anal. ($C_9H_6F_3NO_4S$) C, H, N, F, S.

4-Chloro-3-iodobenzonitrile (60f). A mixture of aldoxime 59 (5.65 g, 20.0 mmol) in acetic anhydride (10 mL) was refluxed for 4 h. The reaction mixture was poured into ice-water and stirred for 1 h. The product was filtered off as a light yellow solid (4.79 g, 91%): mp 91-93° C.; $^1$H NMR δ 8.49 (d, J=2.2 Hz, 1H), 7.90 (dd, J=8.2 and 2.2 Hz, 1H), 7.79 (d, J=8.2 Hz, 1H); HPLC (Method B) $t_R$ 6.24 min (91.75 area % at 254 nm). Anal. ($C_7H_3$ClIN) C, H, N, Cl, I.

General Procedure for Silyl Acetylenes (61 b,e,f). CuI (2 mol %) was added to a stirred mixture of an aryl halide 60, (trimethylsilyl)acetylene (min. 1.3 equiv), and $PdCl_2(PPh_3)_2$ (2 mol %) in triethylamine. See Roesch, K. R., et al., J. Org. Chem., 66, 412-420 (2001). The mixture was heated at 60° C. until the reaction was complete (ca. 3 h). Salts were filtered off and washed with EtOAc. Combined filtrates were evaporated under reduced pressure, and the residue was purified by column chromatography eluting with hexane/EtOAc. The recovered material was recrystallized as necessary.

3-nitro-4-[2-(trimethylsilyl)ethynyl]benzonitrile (61 b) was prepared from aryl bromide 60b as an off-white solid (1.61 g, 66%): mp 81-82° C. (toluene/hexane); $^1$H NMR δ 8.69 (d, J=1.6 Hz, 1H), 8.20 (dd, J=8.0 and 1.6 Hz, 1H), 7.94 (d, J=8.2 Hz, 1H), 0.27 (s, 9H); HPLC (Method B) $t_R$ 8.39 min (100 area % at 254 nm). Anal. ($C_{12}H_{12}N_2O_2Si$) C, H, N.

3-chloro-4[(2-(trimethylsilyl)ethynyl]benzonitrile (61c). A mixture of aryl bromide 60c, (3.96 g, 18.2 mmol), (trimethylsilyl)acetylene (1.80 g, 18.23 mmol), $PPh_3$ (0.24 g, 0.91 mol), Pd ($PPh_3$)$_4$ (0.11 g, 0.09 mmol), and CuI (0.17 g, 0.91 mmol) in piperidine was stirred at 90° C. for 1 h. The reaction mixture was poured into water and extracted into EtOAc. Column chromatography [hexanes/EtOAc (40:1)] gave a white solid (3.24 g, 37%); mp 82-83° C.; $^1$H NMR δ 8.27 (d, J=1.9 Hz, 1H), 8.02 (d, J=8.4 Hz, 1H), 7.78 (dd, J=8.3 and 1.9 Hz, 1H), 0.27 (s, 9H); HPLC (Method B) $t_R$ 9.41 min (100 area % at 265 nm). Anal. ($C_{12}H_{12}$ClNSi) C, H, N, Cl.

4-chloro-3-[2-(trimethylsilyl)ethynyl]benzonitrile (61e) was prepared from aryl iodide 60f to give a white solid (3.11 g, 88%): mp 72-73° C. (hexanes); $^1$H NMR δ 8.12 (d, J=1.6 Hz, 1H), 7.90 (dd, J=8.2 and 1.6 Hz, 1H), 7.80 (d, J=8.2 Hz, 1H), 0.27 (s, 9H); HPLC (Method B) $t_R$ 9.35 min (100 area % at 254 nm). Anal. ($C_{12}H_{12}$ClNSi) C, H, N, Cl.

4-methoxy-3-[(trimethylsilyl)ethynyl]benzonitrile (61f) was prepared from aryl bromide 60g to give a white solid (8.67 g, 80%): mp 63-64° C. (hexanes; $^1$H NMR δ 7.87 (d, J=2.2 Hz, 1H), 7.86 (dd, J=9.7 and 2.2 Hz, 1H), 7.24 (d, J=9.7 Hz, 1H), 3.91 (s, 3H), 0.27 (s, 9H); HPLC (Method B) $t_R$ 8.31 min (98.12 area % at 254 nm). Anal. ($C_{13}H_{15}$NOSi) C, H, N.

3-Chloro-4-(3-hydroxy-3-methylbut-1-ynyl)benzonitrile (62b). 2-Methyl-3-butyn-2-ol (2.5 equiv) was added to a mixture of an aryl bromide 60c, $K_2CO_3$ (2.5 equiv), CuI (4 mol %), $PPh_3$ (8 mol %), and 10% Pd/C (2 mol %) in DME and water. See Bleicher, L. S. et al., J. Org. Chem., 63, 1109-1118 (1998). The biphasic mixture was stirred at reflux under Ar overnight, and was then filtered (Celite) and partitioned between water and EtOAc. Column chromatography gave a white solid (4.25 g, 77%): mp 63-65° C. (hexane); $^1$H NMR δ 8.18 (d, J=1.5 Hz, 1H), 7.83 (dd, J=8.1 and 1.6 Hz, 1H), 7.69 (d, J=8.1 Hz, 1H), 5.68 (s, 1H), 1.50 (s, 6H); HPLC (Method B) $t_R$ 5.00 min (100 area % at 265 nm). Anal. ($C_{12}H_{10}$ClNO) C, H, N, Cl.

General Procedure for Butynyl Benzenes (62c-f). Methodology was similar to that employed for 61b, e, f except that 2-methyl-3-butyn-2-ol (2.5 equiv) was used in place of (trimethylsilyl)acetylene.

4-(3-hydroxy-3-methylbut-1-ynyl)-3-methoxy-benzonitrile (62c) was prepared from aryl triflate 60d to give off-white crystals (19.1 g, 86%): mp 68-70° C. (hexanes/EtOAc); $^1$H NMR δ 7.54 (d, J=1.4 Hz, 1H), 7.48 (d, J=8.0 Hz, 1H), 7.40 (dd, J=7.8 and 1.5 Hz, 1H), 5.55 (s, 1H), 3.87 (s, 3H), 1.46 s, 6H); HPLC (Method B) $t_R$ 4.09 min (100 area % at 230 nm). Anal. ($C_{13}H_{13}NO_2 \cdot 0.4H_2O$) C, H.

3-(3-Hydroxy-3-methylbut-1-ynyl)benzonitrile (62d) was prepared from 3-bromobenzonitrile to give a light-brown oil (20.0 g, 100%): $^1$H NMR δ 7.85 (dd, J=1.5 and 1.5 Hz, 1H), 7.84 (ddd, J=7.8, 1.5 and 1.5 Hz, 1H), 7.72 (ddd, J=7.8, 1.5 and 1.5 Hz, 1H), 7.61 (dd, J=7.8, and 7.8 Hz, 1H), 5.57 (s, 1H), 1.47 (s, 6H); HPLC (method B) $t_R$ 3.99 min (100 area % at 254 nm). Anal. ($C_{12}H_{11}NO$) C, H, N.

4-Chloro-3-(3-hydroxy-3-methylbut-1-ynyl)benzonitrile (62e) was prepared from aryl iodide 60f to give off-white crystals (3.40 g, 82%): mp 80-82° C. (hexanes/EtOAc); $^1$H NMR δ 8.03 (dd, J=2.0 and 0.7 Hz, 1H), 7.86 (ddd, J=8.4, 2.0 and 0.7 Hz, 1H), 7.78 (dd, J=8.4 and 0.7 Hz, 1H), 5.63 (s, 1H), 1.49 (s, 6H); HPLC (method B) $t_R$ 4.86 min (100 area % at 254 nm). Anal. ($C_{12}H_{10}ClNO$) C, H, N, Cl.

3-(3-Hydroxy-3-methylbut-1-ynyl)-4-methoxy-benzonitrile (62f) was from 3-bromo-4-methoxybenzonitrile to give off-white crystals (30.5 g, 99%): mp 63-65° C. (hexanes/EtOAc); $^1$H NMR δ 7.82 (dd, J=8.7 and 2.1 Hz, 1H), 7.77 (d, J=2.1 Hz, 1H), 7.22 (d, J=8.7 Hz, 1H), 5.51 (s, 1H), 3.90 (s, 3H), 1.46 (s, 6H); HPLC (method B) $t_R$ 3.83 min (100 area % at 254 nm). Anal. ($C_{13}H_{13}NO_2$) C, H, N.

3-Methoxy-4-dibromomethylbenzonitrile (65). A mixture of 4-methyl-3-methoxybenzonitrile 64 (11.4 g, 77.6 mmol), NBS (34.5 g, 194 mmol), benzoyl peroxide (1.01 g, 4.17 mmol) in $CCl_4$ was refluxed for 3 h. The reaction mixture was diluted with water and extracted with $CH_2Cl_2$. Column chromatography [hexane/EtOAc (19:1)] of the extracts afforded white crystals (18.3 g, 77%): mp 78-79° C.; $^1$H NMR δ 7.88 (d, J=8.0 Hz, 1H), 7.60 (d, J=1.4 Hz, 1H), 7.52 (dd, J=8.0 and 1.5 Hz, 1H), 7.34 (s, 1H), 3.96 (s, 3H); HPLC (Method B) $t_R$ 7.03 min (100 area % at 254 nm). Anal. ($C_9H_7Br_2NO$) C, H, N, Br.

3-nitro-4-[(2-N,N-dimethylamino)ethenyl]benzonitrile (66). N,N-Dimethyl-formamide dimethyl acetal (12.1 g, 101 mmol) was added to a solution of nitrotoluene 63 (16.3 g, 101 mmol) in dry DMF (60 mL). The mixture was refluxed overnight under $N_2$. The reaction mixture was poured into ice water to give a red solid (21.5 g, 99%): mp 122-126° C.; $^1$H NMR δ 8.22 (d, J=1.6 Hz, 1H), 7.84 (d, J=13.2 Hz, 1H), 7.82 (d, J=8.8 Hz, 1H), 7.65 (dd, J=8.8 and 1.6 Hz, 1H), 5.67 (d, J=13.2 Hz, 1H), 2.98 (s, 6H). Anal. ($C_{11}H_{11}N_3O_2$) C, H, N.

2-Chloro-5-bromobenzoic acid methyl ester (72). A solution of benzoic acid 69 (30.0 g, 127 mmol) and $H_2SO_4$ (2 mL) in MeOH (2 L) was stirred at reflux for 3 d. The reaction mixture was concentrated to give white crystals (31.2 g, 98%): mp 43-44° C.; $^1$H NMR δ 7.99 (d, J=2.4 Hz, 1H), 7.80 (dd, J=8.6 and 2.5 Hz, 1H), 7.56 (d, J=8.6 Hz, 1H), 3.87 (s, 3H); HPLC (Method B) $t_R$ 6.34 min (100 area % at 230 nm).

2-Chloro-5-cyanobenzoic acid methyl ester (73). DCC (11.4 g, 55.0 mmol) was added to a solution of benzoic acid 71, (9.08 g, 50.0 mmol), DMAP (0.60 g, 5.00 mmol) and MeOH (5 mL) in $CH_2Cl_2$ (100 mL) at 0° C. After 1 h the solution was warmed to 25° C. The reaction mixture was filtered and evaporated. The residue was purified by column chromatography ($CH_2Cl_2$) to give a light solid (9.21 g, 94%): mp 100-103° C.; $^1$H NMR δ 8.30 (d, J=2.2 Hz, 1H), 8.07 (dd, J=8.2 and 2.2 Hz, 1H), 7.84 (d, J=8.2 Hz, 1H), 3.89 (s, 3H); HPLC (Method B) $t_R$ 4.57 min (100 area % at 254 nm).

4-Cyano-2-nitrobenzaldehyde (74a). $NaIO_4$ (65.0 g, 304 mmol) was added to a solution of intermediate 66 (21.0 g, 96.7 mmol) in THF and water (350 mL each). The mixture was stirred for 2.5 h, filtered, and extracted into EtOAc, and evaporated. Filtration of a suspension of the residue in $CHCl_3$ through a plug of silica gel followed by recrystallization from toluene with activated carbon gave yellow crystals (13.1 g, 77%): mp 109-111° C.; $^1$H NMR δ 10.27 (s, 1H), 8.75 (d, J=1.5 Hz, 1H), 8.40 (dd, J=8.0 and 1.5 Hz, 1H), 8.05 (d, J=8.0 Hz, 1H). Anal. ($C_8H_4N_2O_3$) C, H, N.

2-Chloro 4-cyanobenzaldehyde (74b). A solution of NaOEt was prepared from sodium (2.01 g, 87.4 mmol) and dry EtOH (150 mL). 2-Nitropropane (8 mL, 89 mmol) was added, followed after a few min by 3-chloro-4-bromomethylbenzonitrile (68, 13.5 g, 58.6 mmol). The mixture was stirred overnight, filtered, and evaporated. The residue was partitioned between water and EtOAc to give white solid (8.63 g, 89%). An analytical sample was recrystallized from aq. EtOH to give white needles: mp 117-119° C. (lit. 122-1230), see Schultz, E. M., et al., *J. Med. Chem.*, 19(6), 783-787 (1976); $^1$H NMR δ 10.34 (s, 1H), 8.29 (m, 1H), 8.00 (m, 2H). Anal. ($C_8H_4ClNO$) C, H, N, Cl.

5-Bromo-2-chlorobenzaldehyde (74c). A solution of pyrrolidine (4.00 g, 56.0 mmol) in MTBE (12 mL) was added dropwise over 20 min to a solution of Red-Al® (3.4 M solution in toluene, 16 ml, 54.4 mmol) in MTBE (33 mL) maintained at −20° C. The mixture was stirred for 1 h at 25° C. A solution of potassium tert-butoxide (0.60 g, 5.36 mmol) in THF (3 mL) was added. The resulting solution was added dropwise to a solution of 2-chloro-5-bromobenzoic acid methyl ester (72, 6.80 g, 27.3 mmol) in MTBE (15 mL) at 10° C. After 15 min the mixture was quenched with 2 N HCl (300 mL). Repeated recrystallizations (hexanes) of the recovered material gave a crude solid (3.22 g, 54%, mp 43-46° C.), which was used without further purification in the next step. 2-Chloro-5-cyanobenzaldehyde (74e) was prepared from ester 73 as described above for 74c. See Dann, O., et al., *Liebigs Ann. Chem.*, 3, 438-455 (1986). Column chromatography of crude material (7.60 g, 100%) [hexane/EtOAc (7:3)], followed by recrystallization from hexane/EtOAc (2:1) gave a solid (3.15 g, 41%): mp 191-193° C.; $^1$H NMR δ 10.28 (s, 1H), 8.28 (d, J=2.2 Hz, 1H), 8.17 (dd, J=8.2 and 2.2 Hz, 1H), 7.87 (d, J=8.2 Hz, 1H); HPLC (Method B) $t_R$ 3.70 min (100 area % at 254 nm) Anal. ($C_8H_4ClNO$) C, H, N, Cl.

General Procedure for Oximes (75b-e,g-h). The aldehydes were treated with hydroxylamine hydrochloride (1.1 equiv) in aq. EtOH (for 75b-e) or EtOH/pyridine (for 75g-h). Products were isolated as precipitates filtered from the reaction mixtures (75b-d) or by extraction from concentrated reaction mixtures (75e,g,h). added to a mixture of an aldehyde 44 or 74 in EtOH, resulting in the dissolution of any suspended solids. Unless stated otherwise, the product precipitated from solution and was filtered off after dilution of the reaction mixture with water.

4-Cyano-2-nitrobenzaldoxime (75b) was prepared from aldehyde 74a as a white solid (3.34 g, 90%): mp 162-163° C.; $^1$H NMR δ 12.34 (s, 1H), 8.61 (d, J=1.6 Hz, 1H), 8.43 (s, 1H), 8.19 (dd, J=8.1 and 1.7 Hz, 1H), 8.06 (d, J=8.5 Hz, 1H. Anal. ($C_8H_5N_3O_3$) C, H, N.

2-Chloro-4-cyanobenzaldoxime (75c) was prepared from aldehyde 74b as a white solid (3.32 g, 92%): mp 177-179° C.; $^1$H NMR δ 12.18 (s, 1H), 8.39 (s, 1H), 8.15 (d, J=1.5 Hz, 1H), 7.97 (d, J=8.2 Hz, 1H), 7.83 (dd, J=8.1 and 1.6 Hz, 1H). Anal. ($C_8H_5ClN_2O_2$) C, H.

4-Cyano-2-methoxybenzaldoxime (75d) was prepared from aldehyde 44b as a white solid (19.6 g, 95%): mp 170-171° C.; $^1$H NMR δ 11.73 (s, 1H), 8.29 (s, 1H), 7.81 (d, J=8.0 Hz, 1H), 7.58 (s, 1H), 7.42 (d, J=8.0 Hz, 1H), 3.89 (s, 3H); HPLC (Method B) $t_R$ 3.16 min (100 area % at 265 nm). Anal. ($C_9H_8N_2O_2$) C, H, N.

5-Bromo-2-chlorobenzaldoxime (75e) was prepared from crude aldehyde 74c as a brown solid (1.52 g, 48%): mp 126-128° C.; $^1$H NMR δ 11.93 (br s, 1H), 8.30 (s, 1H), 7.90 (d, J=2.5 Hz, 1H), 7.62 (dd, J=8.6 and 2.5 Hz, 1H), 7.49 (d, J=8.6

Hz, 1H); HPLC (Method B) $t_R$ 5.47 min (99.0 area % at 230 nm). Anal. ($C_7H_5BrClNO.0.05C_2H_5OH$) C, H, N, Br, Cl.

5-Cyano-2-chlorobenzaldoxime (75g) was prepared from aldehyde 74e as a solid (3.10 g, 100%): mp 191-193° C. (EtOH); $^1H$ NMR δ 12.06 (s, 1H), 8.35 (s, 1H), 8.16 (d, J=2.2 Hz, 1H), 7.89 (dd, J=8.2 and 2.2 Hz, 1H), 7.76 (d, J=8.2 Hz, 1H); HPLC (Method B) $t_R$ 3.69 min (95.99 area % at 230 nm). Anal. ($C_8H_5ClN_2O$) C, H, N, Cl.

5-Cyano-2-methoxybenzaldoxime (75h) was prepared from aldehyde 74f as a yellow solid (4.92 g, 90%): mp 142-144° C. (EtOAc/hexane); $^1H$ NMR δ 11.61 (s, 1H), 8.25 (s, 1H), 7.96 (d, J=2.2 Hz, 1H), 7.87 (dd, J=8.8 and 2.2 Hz, 1H), 7.27 (d, J=8.8 Hz, 1H), 3.92 (s, 3H); HPLC (Method B) $t_R$ 2.84 min (95.20 area % at 230 nm). Anal. ($C_9H_8N_2O_2.0.1$ EtOAc) C, H, N, Cl.

Biological Results

In vitro antiprotozoal activities, see Ismail, M. A., et al., *J. Med. Chem.* 46, 4761-4769 (2003), and cytotoxicity were measured following established protocols, see Balz, T., et al., *EMBO J.*, 4, 1273-1277 (1985); Räz. B., et al., *Acta Trop.*, 68:139-147 (1997); and Sperandeo, N. R. et al., *Chem. Biochem.*, 4, 69-73 (2003). The activities of compounds 1-43 against *Trypanosoma brucei brucei* and *Plasmodium falciparum*, as well as their cytotoxicities to VERO cells (e.g., a cell line derived from the kidney of the African green monkey (*Cercopithecus Aethiops*), available from American Type Culture Collection (ATCC), Manassas, Va., United States of America), are shown in Table 1. These values are compared to those of furamidine. Other positive controls employed were melarsoprol (against *T. brucei*), chloroquine, and artemisinin (against *P. falciparum*), and podophyllotoxin (against VERO cells).

Eleven compounds (3, 13, 16-18, 22, 26, 29, 31, 37, 41) displayed activities against *T. brucei brucei* ($IC_{50}$ values of 3.5-9.0 nM), which were comparable to that of furamidine (4.3 nM). Among this group, all were less toxic than furamidine except for 3. Compound 22 displayed the highest activity (3.5 nM). Compound 31 and 18, (activities of 5.7 and 6.5 nM, respectively) displayed therapeutic indices approximately 20 times greater than that of furamidine.

The isoxazoles, as a whole, were more active against *P. falciparum*. Eleven compounds (4, 5, 7, 8, 12, 18-22, 25) displayed antiplasmodial $IC_{50}$ values of less than 8.0 nM, and sixteen compounds (3, 6, 14, 16, 17, 26, 28-32, 36, 37, 40, 41, 43) displayed activities between 8 and 30 nM (compared to 15.5 nM for furamidine). Among the eleven most active compounds, 19 had the lowest $IC_{50}$ value (2.1 nM). Compounds 21 and 18 displayed high antiplasmodial activity (2.6 and 3.5 nM) in addition to low cytoxicity, reflecting therapeutic indices 200 and 120 times greater than that of furamidine, respectively. Compounds 4 and 14 (antiplasmodial activities of 6.6 and 10.6 nM) demonstrated 30- and 45-fold selectivities against *P. falciparum* over *T. brucei brucei*, respectively. Such selectivity can be desirable for drugs used in treating patients with mixed infections.

Thirty-eight of the 43 isoxazoles were less toxic than furamidine ($IC_{50}$ value of 6.4 μM against VERO cells). Seventeen compounds (4, 8, 14, 18, 23, 27, 29, 30, 31, 32, 33, 36, 37, 38, 40, 43) displayed $IC_{50}$ values greater than 100 μM. The least toxic compound was 40 (215 μM).

TABLE 1

Activity of 3,5-Diphenylisoxazoles against *Trypanosoma brucei brucei* and *Plasmodium falciparum* and Cytotoxicities to VERO cells.

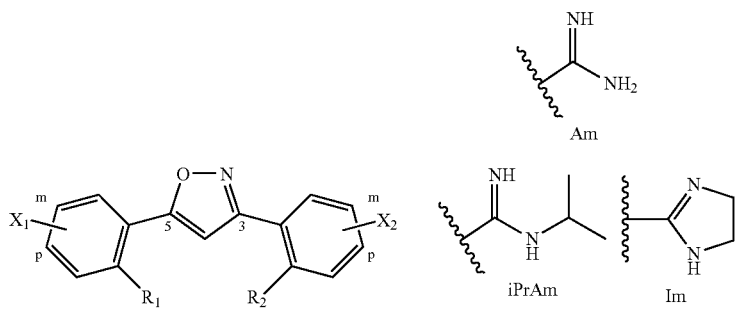

| Cmpd. No. | $X_1$ | $R_1$ | $R_2$ | $X_2$ | *Trypanosoma brucei brucei* | *Plasmodium falciparum* | Cytotoxicity VERO cells |
|---|---|---|---|---|---|---|---|
| 1. | p-Am | H | H | H | 1.7191 | 3.2964 | 19.12 |
| 2. | H | H | H | p-Am | 1.1208 | 3.2964 | 18.46 |
| 3. | p-Am | H | H | p-Am | 0.0051 | 0.0226 | 2.13 |
| 4. | p-iPrAm | H | H | p-iPrAm | 0.1963 | 0.0066 | 175.80 |
| 5. | p-Im | H | H | p-Im | 0.0872 | 0.0041 | 1.81 |
| 6. | p-Am | $NO_2$ | H | p-Am | 0.0139 | 0.0149 | 15.83 |
| 7. | p-Am | Cl | H | p-Am | 0.0155 | 0.0079 | 41.00 |
| 8. | p-Am | OMe | H | p-Am | 0.0106 | 0.0060 | 122.19 |
| 9. | p-Am | H | $NO_2$ | p-Am | 0.0324 | 0.0401 | 22.23 |
| 10. | p-Am | H | Cl | p-Am | 0.0232 | 0.0555 | 5.69 |
| 11. | p-Am | H | OMe | p-Am | 0.0164 | 0.0663 | 92.59 |
| 12. | p-Am | OMe | OMe | p-Am | 0.0130 | 0.0061 | 84.78 |
| 13. | p-Am | H | H | m-Am | 0.0063 | 0.0578 | 24.08 |
| 14. | p-iPrAm | H | H | m-iPrAm | 0.4881 | 0.0106 | 187.33 |
| 15. | p-Im | H | H | m-Im | 1.5544 | 0.0512 | 64.96 |
| 16. | p-Am | $NO_2$ | H | m-Am | 0.0090 | 0.0259 | 48.01 |
| 17. | p-Am | Cl | H | m-Am | 0.0063 | 0.0187 | 82.72 |

TABLE 1-continued

Activity of 3,5-Diphenylisoxazoles against *Trypanosoma brucei brucei*
and *Plasmodium falciparum* and Cytotoxicities to VERO cells.

| Cmpd. No. | $X_1$ | $R_1$ | $R_2$ | $X_2$ | *Trypanosoma brucei brucei* IC$_{50}$ (µM) | *Plasmodium falciparum* IC$_{50}$ (µM) | Cytotoxicity VERO cells IC$_{50}$ (µM) |
|---|---|---|---|---|---|---|---|
| 18. | p-Am | OMe | H | m-Am | 0.0065 | 0.0035 | 176.97 |
| 19. | p-Am | H | NO$_2$ | m-Am | 0.0512 | 0.0021 | 5.07 |
| 20. | p-Am | H | Cl | m-Am | 0.0212 | 0.0071 | 5.67 |
| 21. | p-Am | H | OMe | m-Am | 0.0118 | 0.0026 | 212.92 |
| 22. | m-Am | H | H | p-Am | 0.0035 | 0.0025 | 31.23 |
| 23. | m-iPrAm | H | H | p-iPrAm | 0.3161 | 0.0347 | 185.94 |
| 24. | m-Im | H | H | p-Im | 0.9735 | 0.0770 | 30.23 |
| 25. | m-Am | Cl | H | p-Am | 0.0209 | 0.0035 | 71.39 |
| 26. | m-Am | OMe | H | p-Am | 0.0043 | 0.0116 | 52.79 |
| 27. | m-Am | H | NO$_2$ | p-Am | 0.0194 | 0.0304 | 205.80 |
| 28. | m-Am | H | Cl | p-Am | 0.0116 | 0.0141 | 87.40 |
| 29. | m-Am | H | OMe | p-Am | 0.0059 | 0.0089 | 135.98 |
| 30. | m-Am | OMe | NO$_2$ | p-Am | 0.0342 | 0.0195 | 116.21 |
| 31. | m-Am | OMe | OMe | p-Am | 0.0057 | 0.0297 | 191.19 |
| 32. | m-Am | H | H | m-Am | 0.0290 | 0.0092 | 153.03 |
| 33. | m-iPrAm | H | H | m-iPrAm | 4.9834 | 0.0431 | 180.49 |
| 34. | m-Im | H | H | m-Im | 18.4539 | 0.2272 | 26.18 |
| 35. | m-Am | NO$_2$ | H | m-Am | 1.6283 | 0.3343 | 9.80 |
| 36. | m-Am | Cl | H | m-Am | 0.0251 | 0.0163 | 109.43 |
| 37. | m-Am | OMe | H | m-Am | 0.0074 | 0.0192 | 124.50 |
| 38. | m-Am | H | NO$_2$ | m-Am | 0.0850 | 0.1045 | 176.99 |
| 39. | m-Am | H | Cl | m-Am | 0.0463 | 0.0306 | 55.45 |
| 40. | m-Am | H | OMe | m-Am | 0.0270 | 0.0174 | 214.75 |
| 41. | m-Am | OMe | OMe | m-Am | 0.0042 | 0.0211 | 79.94 |
| 42. | m-iPrAm | OMe | OMe | m-iPrAm | 0.3738 | 0.0932 | 21.74 |
| 43. | m-Im | OMe | OMe | m-Im | 0.0448 | 0.0114 | 164.40 |
| Melarsoprol | | | | | 0.00637 | | |
| Chloroquine | | | | | | 0.1035 | |
| Artemisinin | | | | | | 0.0067 | |
| Podophyllotoxin | | | | | | | 0.0186 |
| Furamidine | | | | | 0.0043 | 0.0155 | 6.40 |

Structure-Activity Relationship

Diamidine 3, the dicationic isoxazole most structurally similar to furamidine, displayed similar IC$_{50}$ values against *T. brucei brucei*, *P. falciparum*, and VERO cells. The effects of structural modifications upon antiprotozoal activity varied with the organism.

Several observations can be made concerning structure-activity relationships regarding antitrypanosomal activity. Comparison of the IC$_{50}$ values of the regioisomeric parent diamidines 3, 13, 22, 32 (5.1, 6.3, 3.5, 29 nM), respectively, show that activity is somewhat enhanced by at least one para-amidino group. In all cases, the substitution of the amidine functions of these compounds with N-isopropylamidines (4, 13, 23, 33) and imidazolines (5, 15, 24, 34), respectively, resulted in decreased activity. The introduction of nitro, chloro, and methoxy substituents generally resulted in little change or in a reduction in activity. The exceptions to this trend were methoxy and dimethoxy analogs 37 and 41, respectively, which were more active than parent compound 32. Of the eleven most potent compounds, three were parent compounds (3, 13, 22) and six were methoxy analogs (41, 26, 31, 29, 18, 37)

Antiplasmodial activity was affected differently by structural variations. Among the four parent compounds (3, 13, 22, 32) IC$_{50}$ values 22.6, 57.8, 2.5, and 9.2 nM were observed, respectively. Thus, the position of the two amidine groups had a somewhat more pronounced effect upon antimalarial activity, with activity enhanced by a meta-amidinophenyl group adjacent to the isoxazole oxygen atom. Of these four compounds, 22 was the most active against both organisms. The activities of the most active parent compounds 22 and 32 were not enhanced by any structural modifications (compounds 23-31, 33-43, respectively.) In contrast, structural derivatives of the less active parent compounds 3 and 13 accounted for nine of the eleven most active compounds. Analogs with substituents on the amidine nitrogen atoms (4, 5) and on the 5-phenyl ring (compounds 6-8, 12) were more active than parent compound 3. The activity of the least active parent compound 13 was enhanced by each of the three substituents on either ring (compounds 16-21).

The eleven most active compounds included parent compound 22, N-isopropylamidine 4, imidazoline 5, nitro analog 13, chloro analogs 7, 20, 25, and methoxy analogs 8, 12, 18, 21. Five of these compounds (4, 5, 7, 8, 12) were structural derivatives of parent structure 3; four compounds (18-21) were structural derivatives of parent structure 13; the others included parent compound 22 and its structural derivatives 25. The most highly active compound was nitro analog 19, which was quite toxic. Methoxy analog 21 also was highly active but had a very high therapeutic index.

Of the seventeen least toxic compounds ($IC_{50}$ values greater than 100 µM) nine compounds had at least one methoxy group. This group includes six methoxy compounds (4, 11, 18, 21, 37, 40) two dimethoxy compounds (12, 31) and methoxy-nitro compound 30. Four N-isopropylamidines (4, 14, 23, 33) also were very nontoxic. Other compounds exhibiting low toxicity were two nitro compounds (27, 38), chloro compound 36 and parent compound 32. Seven of the seventeen least toxic compounds included parent compound 32 and six of its structural analogs, five structural analogs of parent 22, three structural analogs of parent 13, and two structural analogs of parent 3.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:
1. A compound of Formula (I):

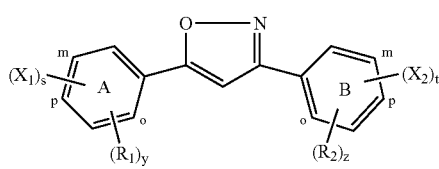

(I)

wherein:
$R_1$ and $R_2$ are each independently selected from the group consisting of H, alkyl, substituted alkyl, halo, nitro, hydroxyl, and alkoxyl;
s and t are each 1;
y and z are each independently an integer from 0 to 3;
$X_1$ and $X_2$ are each:

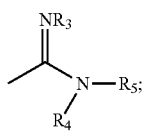

wherein:
each $R_3$ is H, hydroxyl or acyloxyl;
each $R_4$ and $R_5$ is independently selected from the group consisting of H, alkyl, and substituted alkyl; or
$R_3$ and $R_5$ together represent a $C_2$ alkylene;
or a pharmaceutically acceptable salt thereof; and wherein the compound of Formula (I) is a compound selected from the group consisting of:

3,5-Bis[4-(N-isopropyl)amidinophenyl]isoxazole;
3,5-Bis[4-(2-imidazolinyl)phenyl]isoxazole;
5-(4-Amidino-2-nitrophenyl)-3-(4-amidinophenyl)isoxazole;
5-(4-Amidino-2-chlorophenyl)-3-(4-amidinophenyl)isoxazole;
5-(4-Amidino-2-methoxyphenyl)-3-(4-amidinophenyl) isoxazole;
3-(4-Amidino-2-nitrophenyl)-5-(4-amidinophenyl)isoxazole;
3-(4-Amidino-2-chlorophenyl)-5-(4-amidinophenyl)isoxazole;
3-(4-Amidino-2-methoxyphenyl)-5-(4-amidinophenyl) isoxazole;
3,5-Bis(4-amidino-2-methoxyphenyl)isoxazole;
3,5-Bis[4-(N-hydroxy)amidino-2-methoxyphenyl]isoxazole;
3,5-Bis[4-(N-acetoxy)amidino-2-methoxyphenyl]isoxazole;
3,5-Bis[3-(N-isopropyl)amidinophenyl]isoxazole;
3,5-Bis[3-(2-imidazolinyl)phenyl]isoxazole;
5-(5-Amidino-2-nitrophenyl)-3-(3-amidinophenyl)isoxazole;
5-(5-Amidino-2-chlorophenyl)-3-(3-amidinophenyl)isoxazole;
5-(5-Amidino-2-methoxyphenyl)-3-(3-amidinophenyl) isoxazole;
3-(5-Amidino-2-nitrophenyl)-5-(3-amidinophenyl)isoxazole;
3-(5-Amidino-2-chlorophenyl)-5-(3-amidinophenyl)isoxazole;
3-(5-Amidino-2-methoxyphenyl)-5-(3-amidinophenyl) isoxazole;
3,5-Bis(5-amidino-2-methoxyphenyl)isoxazole;
3,5-Bis[5-(N-isopropyl)amidino-2-methoxyphenyl]isoxazole;
3,5-Bis[5-(2-imidazolinyl)-2-methoxyphenyl]isoxazole;
3-[3-(N-Isopropyl)amidinophenyl]-5-[4-(N-isopropyl) amidino-phenyl]-isoxazole;
3-[3-(2-Imidazolinyl)phenyl]-5-[4-(2-imidazolinyl)phenyl]-isoxazole;
5-(4-Amidino-2-nitrophenyl)-3-(3-amidinophenyl)isoxazole;
5-(4-Amidino-2-chlorophenyl)-3-(3-amidinophenyl)isoxazole;
5-(4-Amidino-2-methoxyphenyl)-3-(3-amidinophenyl) isoxazole;
3-(5-Amidino-2-nitrophenyl)-5-(4-amidinophenyl)isoxazole;
3-(5-Amidino-2-chlorophenyl)-5-(4-amidinophenyl)isoxazole;
3-(5-Amidino-2-methoxyphenyl)-5-(4-amidinophenyl) isoxazole;
3-[4-(N-Isopropyl)amidinophenyl]-5-[3-(N-isopropyl) amidino-phenyl]-isoxazole;
3-[4-(2-Imidazolinyl)phenyl]-5-[3-(2-imidazolinyl)phenyl]-isoxazole;
5-(5-Amidino-2-chlorophenyl)-3-(4-amidinophenyl)isoxazole;
5-(5-Amidino-2-methoxyphenyl)-3-(4-amidinophenyl) isoxazole;
3-(4-Amidino-2-nitrophenyl)-5-(3-amidinophenyl)isoxazole;
3-(4-Amidino-2-chlorophenyl)-5-(3-amidinophenyl)isoxazole;
3-(4-Amidino-2-methoxyphenyl)-5-(3-amidinophenyl) isoxazole;

5-(5-Amidino-2-methoxyphenyl)-3-(4-amidino-2-nitrophenyl)isoxazole; and 3-(4-Amidino-2-methoxyphenyl)-5-(5-amidino-2-methoxy-phenyl)-isoxazole, or a pharmaceutically acceptable salt thereof.

2. The compound of claim 1, wherein the compound of Formula (I) is selected from the group consisting of:

3,5-Bis[4-(N-isopropyl)amidinophenyl]isoxazole;

3,5-Bis[4-(2-imidazolinyl)phenyl]isoxazole;

5-(4-Amidino-2-nitrophenyl)-3-(4-amidinophenyl)isoxazole;

5-(4-Amidino-2-chlorophenyl)-3-(4-amidinophenyl)isoxazole;

5-(4-Amidino-2-methoxyphenyl)-3-(4-amidinophenyl)isoxazole;

3-(4-Amidino-2-nitrophenyl)-5-(4-amidinophenyl)isoxazole;

3-(4-Amidino-2-chlorophenyl)-5-(4-amidinophenyl)isoxazole;

3-(4-Amidino-2-methoxyphenyl)-5-(4-amidinophenyl)isoxazole;

3,5-Bis(4-amidino-2-methoxyphenyl)isoxazole;

3,5-Bis[4-(N-hydroxy)amidino-2-methoxyphenyl]isoxazole; and 3,5-Bis[4-(N-acetoxy)amidino-2-methoxyphenyl]isoxazole;

or a pharmaceutically acceptable salt thereof.

3. The compound of claim 1, selected from the group consisting of:

3-[3-(N-Isopropyl)amidinophenyl]-5-[4-(N-isopropyl)amidino-phenyl]-isoxazole;

3-[3-(2-Imidazolinyl)phenyl]-5-[4-(2-imidazolinyl)phenyl]-isoxazole;

5-(4-Amidino-2-nitrophenyl)-3-(3-amidinophenyl)isoxazole;

5-(4-Amidino-2-chlorophenyl)-3-(3-amidinophenyl)isoxazole;

5-(4-Amidino-2-methoxyphenyl)-3-(3-amidinophenyl)isoxazole;

3-(5-Amidino-2-nitrophenyl)-5-(4-amidinophenyl)isoxazole;

3-(5-Amidino-2-chlorophenyl)-5-(4-amidinophenyl)isoxazole; and 3-(5-Amidino-2-methoxyphenyl)-5-(4-amidinophenyl)isoxazole;

or a pharmaceutically acceptable salt thereof.

4. The compound of claim 1, selected from the group consisting of:

3-[4-(N-Isopropyl)amidinophenyl]-5-[3-(N-isopropyl)amidino-phenyl]-isoxazole;

3-[4-(2-Imidazolinyl)phenyl]-5-[3-(2-imidazolinyl)phenyl]-isoxazole;

5-(5-Amidino-2-chlorophenyl)-3-(4-amidinophenyl)isoxazole;

5-(5-Amidino-2-methoxyphenyl)-3-(4-amidinophenyl)isoxazole;

3-(4-Amidino-2-nitrophenyl)-5-(3-amidinophenyl)isoxazole;

3-(4-Amidino-2-chlorophenyl)-5-(3-amidinophenyl)isoxazole;

3-(4-Amidino-2-methoxyphenyl)-5-(3-amidinophenyl)isoxazole;

5-(5-Amidino-2-methoxyphenyl)-3-(4-amidino-2-nitrophenyl)isoxazole; and 3-(4-Amidino-2-methoxyphenyl)-5-(5-amidino-2-methoxy-phenyl)-isoxazole;

or a pharmaceutically acceptable salt thereof.

5. A compound of Formula (Id):

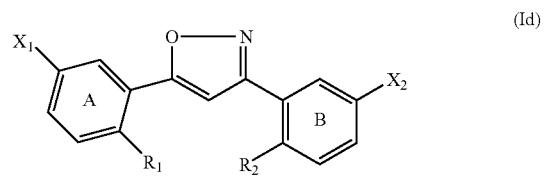

wherein:

$R_1$ and $R_2$ are each independently selected from the group consisting of H, alkyl, substituted alkyl, halo, nitro, hydroxyl, and alkoxyl;

$X_1$ and $X_2$ are each:

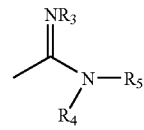

wherein:

each $R_3$ is H;

each $R_4$ and $R_5$ is independently selected from the group consisting of H, alkyl, and substituted alkyl; or $R_3$ and $R_5$ together represent a $C_2$ alkylene;

or a pharmaceutically acceptable salt thereof; wherein the compound of Formula (Id) is selected from the group consisting of:

3,5-Bis[3-(N-isopropyl)amidinophenyl]isoxazole;

3,5-Bis[3-(2-imidazolinyl)phenyl]isoxazole;

5-(5-Amidino-2-nitrophenyl)-3-(3-amidinophenyl)isoxazole;

5-(5-Amidino-2-chlorophenyl)-3-(3-amidinophenyl)isoxazole;

5-(5-Amidino-2-methoxyphenyl)-3-(3-amidinophenyl)isoxazole;

3-(5-Amidino-2-nitrophenyl)-5-(3-amidinophenyl)isoxazole;

3-(5-Amidino-2-chlorophenyl)-5-(3-amidinophenyl)isoxazole;

3-(5-Amidino-2-methoxyphenyl)-5-(3-amidinophenyl)isoxazole;

3,5-Bis(5-amidino-2-methoxyphenyl)isoxazole;

3,5-Bis[5-(N-isopropyl)amidino-2-methoxyphenyl]isoxazole; and 3,5-Bis[5-(2-imidazolinyl)-2-methoxyphenyl]isoxazole;

or a pharmaceutically acceptable salt thereof.

6. The compound of claim 5, wherein the pharmaceutically acceptable salt is a hydrochloride salt.

7. A pharmaceutical formulation comprising:

(a) a compound of claim 5; and (b) a pharmaceutically acceptable carrier.

8. A method for treating a microbial infection in a subject in need of treatment thereof, the method comprising administering to the subject an effective amount of a compound of Formula (I):

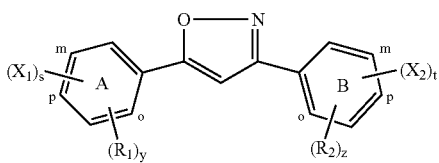

wherein:
R$_1$ and R$_2$ are each independently selected from the group consisting of H, alkyl, substituted alkyl, halo, nitro, hydroxyl, and alkoxyl;
s and t are each 1;
y and z are each independently an integer from 0 to 3;
X$_1$ and X$_2$ are each:

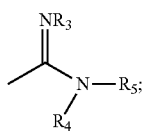

wherein:
each R$_3$ is H, hydroxyl, or acyloxyl;
each R$_4$ and R$_5$ is independently selected from the group consisting of H, alkyl, and substituted alkyl; or
R$_3$ and R$_5$ together represent a C$_2$ alkylene;
or a pharmaceutically acceptable salt thereof; and wherein the compound of Formula (I) is a compound selected from the group consisting of:
3,5-Bis[4-(N-isopropyl)amidinophenyl]isoxazole;
3,5-Bis[4-(2-imidazolinyl)phenyl]isoxazole;
5-(4-Amidino-2-nitrophenyl)-3-(4-amidinophenyl)isoxazole;
5-(4-Amidino-2-chlorophenyl)-3-(4-amidinophenyl)isoxazole;
5-(4-Amidino-2-methoxyphenyl)-3-(4-amidinophenyl)isoxazole;
3-(4-Amidino-2-nitrophenyl)-5-(4-amidinophenyl)isoxazole;
3-(4-Amidino-2-chlorophenyl)-5-(4-amidinophenyl)isoxazole;
3-(4-Amidino-2-methoxyphenyl)-5-(4-amidinophenyl)isoxazole;
3,5-Bis(4-amidino-2-methoxyphenyl)isoxazole;
3,5-Bis[4-(N-hydroxy)amidino-2-methoxyphenyl]isoxazole;
3,5-Bis[4-(N-acetoxy)amidino-2-methoxyphenyl]isoxazole;
3,5-Bis[3-(N-isopropyl)amidinophenyl]isoxazole;
3,5-Bis[3-(2-imidazolinyl)phenyl]isoxazole;
5-(5-Amidino-2-nitrophenyl)-3-(3-amidinophenyl)isoxazole;
5-(5-Amidino-2-chlorophenyl)-3-(3-amidinophenyl)isoxazole;
5-(5-Amidino-2-methoxyphenyl)-3-(3-amidinophenyl)isoxazole;
3-(5-Amidino-2-nitrophenyl)-5-(3-amidinophenyl)isoxazole;
3-(5-Amidino-2-chlorophenyl)-5-(3-amidinophenyl)isoxazole;
3-(5-Amidino-2-methoxyphenyl)-5-(3-amidinophenyl)isoxazole;
3,5-Bis(5-amidino-2-methoxyphenyl)isoxazole;
3,5-Bis[5-(N-isopropyl)amidino-2-methoxyphenyl]isoxazole;
3,5-Bis[5-(2-imidazolinyl)-2-methoxyphenyl]isoxazole;
3-[3-(N-Isopropyl)amidinophenyl]-5-[4-(N-isopropyl)amidino-phenyl]-isoxazole;
3-[3-(2-Imidazolinyl)phenyl]-5-[4-(2-imidazolinyl)phenyl]-isoxazole;
5-(4-Amidino-2-nitrophenyl)-3-(3-amidinophenyl)isoxazole;
5-(4-Amidino-2-chlorophenyl)-3-(3-amidinophenyl)isoxazole;
5-(4-Amidino-2-methoxyphenyl)-3-(3-amidinophenyl)isoxazole;
3-(5-Amidino-2-nitrophenyl)-5-(4-amidinophenyl)isoxazole;
3-(5-Amidino-2-chlorophenyl)-5-(4-amidinophenyl)isoxazole;
3-(5-Amidino-2-methoxyphenyl)-5-(4-amidinophenyl)isoxazole;
3-[4-(N-Isopropyl)amidinophenyl]-5-[3-(N-isopropyl)amidino-phenyl]-isoxazole;
3-[4-(2-Imidazolinyl)phenyl]-5-[3-(2-imidazolinyl)phenyl]-isoxazole;
5-(5-Amidino-2-chlorophenyl)-3-(4-amidinophenyl)isoxazole;
5-(5-Amidino-2-methoxyphenyl)-3-(4-amidinophenyl)isoxazole;
3-(4-Amidino-2-nitrophenyl)-5-(3-amidinophenyl)isoxazole;
3-(4-Amidino-2-chlorophenyl)-5-(3-amidinophenyl)isoxazole;
3-(4-Amidino-2-methoxyphenyl)-5-(3-amidinophenyl)isoxazole;
5-(5-Amidino-2-methoxyphenyl)-3-(4-amidino-2-nitrophenyl)isoxazole; and
3-(4-Amidino-2-methoxyphenyl)-5-(5-amidino-2-methoxy-phenyl)-isoxazole; or a pharmaceutically acceptable salt thereof.

9. The method of claim 8, wherein the compound of Formula (I) is selected from the group consisting of:
3,5-Bis[4-(N-isopropyl)amidinophenyl]isoxazole;
3,5-Bis[4-(2-imidazolinyl)phenyl]isoxazole;
5-(4-Amidino-2-nitrophenyl)-3-(4-amidinophenyl)isoxazole;
5-(4-Amidino-2-chlorophenyl)-3-(4-amidinophenyl)isoxazole;
5-(4-Amidino-2-methoxyphenyl)-3-(4-amidinophenyl)isoxazole;
3-(4-Amidino-2-nitrophenyl)-5-(4-amidinophenyl)isoxazole;
3-(4-Amidino-2-chlorophenyl)-5-(4-amidinophenyl)isoxazole;
3-(4-Amidino-2-methoxyphenyl)-5-(4-amidinophenyl)isoxazole;
3,5-Bis(4-amidino-2-methoxyphenyl)isoxazole;
3,5-Bis[4-(N-hydroxy)amidino-2-methoxyphenyl]isoxazole; and
3,5-Bis[4-(N-acetoxy)amidino-2-methoxyphenyl]isoxazole;
or a pharmaceutically acceptable salt thereof.

10. The method of claim 8, wherein the compound of Formula (I) is selected from the group consisting of:
3-[3-(N-Isopropyl)amidinophenyl]-5-[4-(N-isopropyl)amidino-phenyl]-isoxazole;

3-[3-(2-Imidazolinyl)phenyl]-5-[4-(2-imidazolinyl)phenyl]-isoxazole;
5-(4-Amidino-2-nitrophenyl)-3-(3-amidinophenyl)isoxazole;
5-(4-Amidino-2-chlorophenyl)-3-(3-amidinophenyl)isoxazole;
5-(4-Amidino-2-methoxyphenyl)-3-(3-amidinophenyl)isoxazole;
3-(5-Amidino-2-nitrophenyl)-5-(4-amidinophenyl)isoxazole;
3-(5-Amidino-2-chlorophenyl)-5-(4-amidinophenyl)isoxazole; and
3-(5-Amidino-2-methoxyphenyl)-5-(4-amidinophenyl)isoxazole;
or a pharmaceutically acceptable salt thereof.

11. The method of claim 8, wherein the compound of Formula (I) is selected from the group consisting of:
3-[4-(N-Isopropyl)amidinophenyl]-5-[3-(N-isopropyl)amidino-phenyl]-isoxazole;
3-[4-(2-Imidazolinyl)phenyl]-5-[3-(2-imidazolinyl)phenyl]-isoxazole;
5-(5-Amidino-2-chlorophenyl)-3-(4-amidinophenyl)isoxazole;
5-(5-Amidino-2-methoxyphenyl)-3-(4-amidinophenyl)isoxazole;
3-(4-Amidino-2-nitrophenyl)-5-(3-amidinophenyl)isoxazole;
3-(4-Amidino-2-chlorophenyl)-5-(3-amidinophenyl)isoxazole;
3-(4-Amidino-2-methoxyphenyl)-5-(3-amidinophenyl)isoxazole;
5-(5-Amidino-2-methoxyphenyl)-3-(4-amidino-2-nitrophenyl)-isoxazole; and
3-(4-Amidino-2-methoxyphenyl)-5-(5-amidino-2-methoxy-phenyl)-isoxazole;
or a pharmaceutically acceptable salt thereof.

12. A method for treating a microbial infection in a subject in need of treatment thereof, the method comprising administering to the subject an effective amount of a compound of Formula (Id):

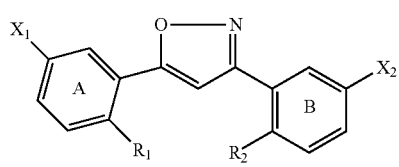

wherein:
R₁ and R₂ are each independently selected from the group consisting of H, alkyl, substituted alkyl, halo, nitro, hydroxyl, and alkoxyl;
X₁ and X₂ are each:

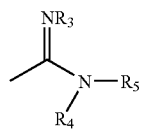

wherein:
each R₃ is H;
each R₄ and R₅ is independently selected from the group consisting of H, alkyl, and substituted alkyl; or
R₃ and R₅ together represent a C₂ alkylene;

or a pharmaceutically acceptable salt thereof; wherein the compound of Formula (Id) is selected from the group consisting of:
3,5-Bis[3-(N-isopropyl)amidinophenyl]isoxazole;
3,5-Bis[3-(2-imidazolinyl)phenyl]isoxazole;
5-(5-Amidino-2-nitrophenyl)-3-(3-amidinophenyl)isoxazole;
5-(5-Amidino-2-chlorophenyl)-3-(3-amidinophenyl)isoxazole;
5-(5-Amidino-2-methoxyphenyl)-3-(3-amidinophenyl)isoxazole;
3-(5-Amidino-2-nitrophenyl)-5-(3-amidinophenyl)isoxazole;
3-(5-Amidino-2-chlorophenyl)-5-(3-amidinophenyl)isoxazole;
3-(5-Amidino-2-methoxyphenyl)-5-(3-amidinophenyl)isoxazole;
3,5-Bis(5-amidino-2-methoxyphenyl)isoxazole;
3,5-Bis[5-(N-isopropyl)amidino-2-methoxyphenyl]isoxazole; and
3,5-Bis[5-(2-imidazolinyl)-2-methoxyphenyl]isoxazole;
or a pharmaceutically acceptable salt thereof.

13. The method of claim 12, wherein the compound of Formula (Id) is administered in the form of a pharmaceutically acceptable salt.

14. The method of claim 13, wherein the pharmaceutically acceptable salt is a hydrochloride salt.

15. The method of claim 12, wherein the microbial infection is selected from the group consisting of a *Trypanosoma* species infection and a *Plasmodium falciparum* infection.

16. The method of claim 15, wherein the *Trypanosoma* species is selected from the group consisting of *Trypanosoma brucei rhodesiense*, *Trypanosoma brucei gambiense*, *Trypanosoma brucei brucei*, and *Trypanosoma cruzi*.

17. A method for preparing a compound of Formula (Id):

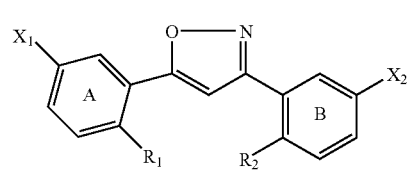

wherein:
R₁ and R₂ are each independently selected from the group consisting of H, alkyl, substituted alkyl, halo, nitro, hydroxyl, and alkoxyl;
X₁ and X₂ are each:

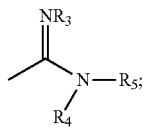

wherein:
each R₃ is H;
each R₄ and R₅ is independently selected from the group consisting of H, alkyl, and substituted alkyl; or
R₃ and R₅ together represent a C₂ alkylene;
or a pharmaceutically acceptable salt thereof; and wherein the compound of Formula (Id) is a compound selected from the group consisting of:
3,5-Bis[3-(N-isopropyl)amidinophenyl]isoxazole;

3,5-Bis[3-(2-imidazolinyl)phenyl]isoxazole;
5-(5-Amidino-2-nitrophenyl)-3-(3-amidinophenyl)isoxazole;
5-(5-Amidino-2-chlorophenyl)-3-(3-amidinophenyl)isoxazole;
5-(5-Amidino-2-methoxyphenyl)-3-(3-amidinophenyl)isoxazole;
3-(5-Amidino-2-nitrophenyl)-5-(3-amidinophenyl)isoxazole;
3-(5-Amidino-2-chlorophenyl)-5-(3-amidinophenyl)isoxazole;
3-(5-Amidino-2-methoxyphenyl)-5-(3-amidinophenyl)isoxazole;
3,5-Bis(5-amidino-2-methoxyphenyl)isoxazole;
3,5-Bis[5-(N-isopropyl)amidino-2-methoxyphenyl]isoxazole; and
3,5-Bis[5-(2-imidazolinyl)-2-methoxyphenyl]isoxazole;
or a pharmaceutically acceptable salt thereof;
the method comprising:
(a) condensing an aryl aldehyde and an aryl ketone in a first polar solvent to form a chalcone;
(b) contacting the chalcone with a halogen to form a dihalochalcone;
(c) contacting the dihalochalcone with hydroxylamine hydrochloride and a base in a first protic solvent to form a diarylisoxazole;
(d) contacting the diarylisoxazole with a strong acid and an alcohol for a period of time, followed by an amine and an alcohol to form a compound of Formula (Id), wherein the compound of Formula (Id) is a diamidine.

18. The method of claim 17, wherein the aryl aldehyde is selected from the group consisting of 3-bromobenzaldehyde and 3-cyanobenzaldehyde.

19. The method of claim 17, wherein the aryl ketone is selected from the group consisting of 3'-bromoacetophenone and 3'-cyanoacetophenone.

20. The method of claim 17, wherein the amine is selected from the group consisting of ammonia, ammonium hydroxide, isopropylamine, and ethylene diamine.

21. The method of claim 17, wherein the halogen is bromine.

22. The method of claim 17, comprising:
(a) contacting the diarylisoxazole in a second aprotic solvent with one of:
(i) cuprous cyanide to form a di-cyanide;
(ii) zinc cyanide and tetrakis(triphenylphosphine)-palladium to form a di-cyanide; and
(iii) an alkyl lithium, followed by tosyl cyanide to form a di-cyanide; and
(b) contacting the di-cyanide with a strong acid and an alcohol, followed by an amine and an alcohol to form a compound of Formula (Id), wherein the compound of Formula (Id) is a diamidine.

23. The method of claim 17 or 22, wherein the strong acid comprises hydrochloric acid.

24. A method for preparing a compound of Formula (Id):

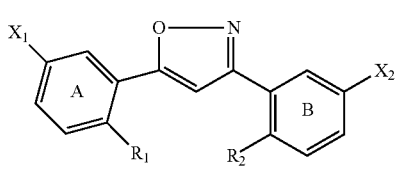

(Id)

wherein:
$R_1$ and $R_2$ are each independently selected from the group consisting of H, alkyl, substituted alkyl, halo, nitro, hydroxyl, and alkoxyl;
$X_1$ and $X_2$ are each:

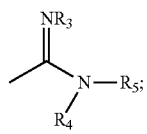

wherein:
each $R_3$ is H;
each $R_4$ and $R_5$ is independently selected from the group consisting of H, alkyl, and substituted alkyl; or
$R_3$ and $R_5$ together represent a $C_2$ alkylene;
or a pharmaceutically acceptable salt thereof; wherein the compound of Formula (Id) is a compound selected from the group consisting of:
3,5-Bis[3-(N-isopropyl)amidinophenyl]isoxazole;
3,5-Bis[3-(2-imidazolinyl)phenyl]isoxazole;
5-(5-Amidino-2-nitrophenyl)-3-(3-amidinophenyl)isoxazole;
5-(5-Amidino-2-chlorophenyl)-3-(3-amidinophenyl)isoxazole;
5-(5-Amidino-2-methoxyphenyl)-3-(3-amidinophenyl)isoxazole;
3-(5-Amidino-2-nitrophenyl)-5-(3-amidinophenyl)isoxazole;
3-(5-Amidino-2-chlorophenyl)-5-(3-amidinophenyl)isoxazole;
3-(5-Amidino-2-methoxyphenyl)-5-(3-amidinophenyl)isoxazole;
3,5-Bis(5-amidino-2-methoxyphenyl)isoxazole;
3,5-Bis[5-(N-isopropyl)amidino-2-methoxyphenyl]isoxazole; and
3,5-Bis[5-(2-imidazolinyl)-2-methoxyphenyl]isoxazole;
or a pharmaceutically acceptable salt thereof;
the method comprising:
(a) contacting a phenylacetylene and a benzaldehyde chlorooxime in a first aprotic solvent in the presence of one of bis(tributyltin)oxide and triethylamine to form a diphenylisoxazole;
(b) contacting the diphenylisoxazole with one of:
(i) a strong acid and an alcohol for a period of time, followed by an amine and an alcohol for a period of time to form a Compound of Formula (Id), wherein the compound of Formula (Id) is a diamidine;
(ii) cuprous cyanide in a second aprotic solvent to form a di-cyanide, followed by a strong acid and an alcohol for a period of time, followed by an amine and an alcohol for a period of time to form a compound of Formula (Id), wherein the compound of Formula (Id) is a diamidine;
(iii) zinc cyanide and tetrakis(triphenylphosphine)-palladium in a second aprotic solvent to form a di-cyanide, followed by a strong acid and an alcohol for a period of time, followed by an amine and an alcohol for a period of time to form a compound of Formula (Id), wherein the compound of Formula (Id) is a diamidine; and
(iv) an alkyl lithium, followed by tosyl cyanide in a second aprotic solvent to form a di-cyanide, followed by a strong acid and an alcohol for a period of time, followed by an amine and an alcohol for a period of time to form a compound of Formula (Id), wherein the compound of Formula (Id) is a diamidine.

25. The method of claim 24, wherein the phenylacetylene is a 3-ethynylbenzonitrile.

26. The method of claim 24, wherein the amine is selected from the group consisting of ammonia, isopropylamine, and ethylene diamine.

27. The method of claim 24, wherein the strong acid is hydrochloric acid.

28. The compound of claim 1, wherein the pharmaceutically acceptable salt is a hydrochloride salt.

29. A pharmaceutical formulation comprising:
(a) a compound of claim 1; and
(b) a pharmaceutically acceptable carrier.

* * * * *